United States Patent
Gauthier et al.

(10) Patent No.: US 12,351,596 B2
(45) Date of Patent: Jul. 8, 2025

(54) TETRASACCHARIDES FOR THE DIAGNOSIS, PREVENTION, AND TREATMENT OF MELIOIDOSIS AND GLANDERS

(71) Applicant: INSTITUT NATIONAL DE LA RECHERCHE SCIENTIFIQUE, Quebec (CA)

(72) Inventors: Charles Gauthier, Laval (CA); Maude Cloutier, Windsor (CA)

(73) Assignee: INSTITUT NATIONAL DE LA RECHERCHE SCIENTIFIQUE, Quebec (CA)

( * ) Notice: Subject to any disclaimer, the term of this patent is extended or adjusted under 35 U.S.C. 154(b) by 743 days.

(21) Appl. No.: 17/595,998

(22) PCT Filed: Apr. 17, 2020

(86) PCT No.: PCT/CA2020/050516
§ 371 (c)(1),
(2) Date: Dec. 1, 2021

(87) PCT Pub. No.: WO2020/243815
PCT Pub. Date: Dec. 10, 2020

(65) Prior Publication Data
US 2022/0227801 A1    Jul. 21, 2022

Related U.S. Application Data

(60) Provisional application No. 62/857,346, filed on Jun. 5, 2019.

(51) Int. Cl.
*C07H 15/08*    (2006.01)
*A61K 39/00*    (2006.01)
(Continued)

(52) U.S. Cl.
CPC ......... *C07H 15/08* (2013.01); *A61K 39/0208* (2013.01); *A61K 39/385* (2013.01);
(Continued)

(58) Field of Classification Search
CPC ......... G01N 33/56911; G01N 2400/50; A61K 39/0208; A61K 39/104; A61K 39/385;
(Continued)

(56) References Cited

U.S. PATENT DOCUMENTS

2012/0251565 A1    10/2012  Torres
2013/0028927 A1*    1/2013  Kozel ............... C07K 16/1214
                                                    435/7.92

FOREIGN PATENT DOCUMENTS

WO    2004006857 A3    1/2004
WO    2006109071 A2    10/2006

OTHER PUBLICATIONS

Cloutier et al., (Nat. Prod. Rep., 2018,35, 1251-1293). (Year: 2018).*

(Continued)

*Primary Examiner* — Jana A Hines
(74) *Attorney, Agent, or Firm* — Lavery, de Billy, L.L.P.; Isabelle Pelletier

(57) ABSTRACT

A tetrasaccharide of formula I and a method of production thereof are provided. Furthermore, a conjugate comprising the tetrasaccharide and a molecule attached to the tetrasaccharide, preferably via its amine group, is also provided. Compositions, preferably immunogenic or vaccine compositions, comprising this tetrasaccharide or this conjugate are also provided. Such tetrasaccharides, conjugates, and compositions can be used for preventing or treating a disease caused by a *Burkholderia* infection in a subject, for inducing the production of anti-*Burkholderia* antibodies in a subject, or for diagnosing a *Burkholderia* infection in a subject.

(Continued)

Preferably, the *Burkholderia* infection is an infection by *Burkholderia pseudomallei* (Bp) or *Burkholderiamallei* (Bm); the disease is melioidosis or glander; and/or the anti-*Burkholderia* antibodies are anti-*Burkholderia pseudomallei*(Bp) antibodies or anti-*Burkholderia mallei* (Bm) antibodies.

16 Claims, 10 Drawing Sheets

(51) Int. Cl.
    *A61K 39/02*     (2006.01)
    *A61K 39/385*     (2006.01)
    *A61K 47/64*     (2017.01)
    *A61P 31/04*     (2006.01)
    *A61P 37/04*     (2006.01)
    *C07H 1/00*     (2006.01)

(52) U.S. Cl.
    CPC ........ *A61K 47/6415* (2017.08); *A61K 47/646* (2017.08); *A61P 31/04* (2018.01); *A61P 37/04* (2018.01); *C07H 1/00* (2013.01); *A61K 2039/6087* (2013.01)

(58) Field of Classification Search
    CPC .. A61K 45/06; A61K 47/6415; A61K 47/646; A61K 2039/6087; A61P 31/04; A61P 37/04; C07H 1/00; C07H 15/08
    See application file for complete search history.

(56) References Cited

OTHER PUBLICATIONS

Kenfack et al., (Nature Communications, vol. 8, Article No. 115 (2017). (Year: 2017).*
Arasappan, A. & Fuchs, P., "Regiospecific 4, 6-functionalization of pyranosides via dimethylboron bromide-mediated cleavage of phthalide orthoesters", Journal of the American Chemical Society 117, p. 177-183 (1995).
AuCoin, D. P. et al., "Polysaccharide specific monoclonal antibodies provide passive protection against intranasal challenge with Burkholderia pseudomallei", PLoS One 7, e35386 (2012).
Baudry, D., Ephritikhine, M. & Felkin, H., "Isomerisation of allyl ethers catalysed by the cationic iridium complex [Ir (cyclo-octa-1, 5-diene)(PMePh 2) 2] PF 6. A highly stereoselective route to trans-propenyl ethers", Journal of the Chemical Society, Chemical Communications, p. 694-695 (1978).
Brett, P. J., Burtnick, M. N. & Woods, D. E., "The wbiA locus is required for the 2-O-acetylation of lipopolysaccharides expressed by Burkholderia pseudomallei and Burkholderia thailandensis", FEMS microbiology letters 218, p. 323-328 (2003).
Bryan, L. E., Wong, S., Woods, D. E., Dance, D. A. & Chaowagul, W., "Passive protection of diabetic rats with antisera specific for the polysaccharide portion of the lipopolysaccharide isolated from Pseudomonas pseudomallei" Canadian Journal of Infectious Diseases and Medical Microbiology 5, p. 170-178 (1994).
Burtnick, M. N., Brett, P. J. & Woods, D. E., "Molecular and physical characterization of Burkholderia mallei O antigens", Journal of bacteriology 184, p. 849-852 (2002).
Cai, X. et al., "Efficient synthesis of a 6-deoxytalose tetrasaccharide related to the antigenic O-polysaccharide produced by Aggregatibacter actinomycetemcomitans serotype c.", Carbohydrate research 345, p. 1230-1234 (2010).
Chantratita, N. et al., "Survey of innate immune responses to Burkholderia pseudomallei in human blood identifies a central role for lipopolysaccharide", PLoS one 8, e81617 (2013).
Cheng, A. C. & Currie, B. J., "Melioidosis: epidemiology, pathophysiology, and management", Clinical microbiology reviews 18, p. 383-416 (2005).
Cloutier, M. et al., "Melioidosis patient serum-reactive synthetic tetrasaccharides bearing the predominant epitopes of Burkholderia pseudomallei and Burkholderia mallei O-antigens", Org. Biomol. Chem., 2019, 17, p. 8878.
Cloutier, M., Muru, K., Ravicoularamin, G. & Gauthier, C., "Polysaccharides from Burkholderia species as targets for vaccine development, immunomodulation and chemical synthesis", Natural product reports 35, p. 1251-1293 (2018).
Currie, B. J., "Melioidosis: Evolving Concepts in Epidemiology, Pathogenesis, and Treatment, in Seminars in respiratory and critical care medicine", vol. 36, No. 1, 111-125 (Thieme Medical Publishers) (2015).
Dance, D., "Melioidosis: the tip of the iceberg?" Clinical Microbiology Reviews, vol. 4, No. 1, p. 52-60 (1991).
Danzig, R. & Berkowsky, P. B., "Why should we be concerned about biological warfare?" J American Medical Association, 278, p. 431-432 (1997).
Ellervik, U., Grundberg, H. & Magnusson, G., "Synthesis of lactam and acetamido analogues of sialyl Lewis X tetrasaccharide and Lewis X trisaccharide", The Journal of organic chemistry 63, p. 9323-9338 (1998).
Frihed, T. G., Pedersen, C. M. & Bols, M., "Synthesis of All Eight Stereoisomeric 6-Deoxy-L-hexopyranosyl Donors—Trends in Using Stereoselective Reductions or Mitsunobu Epimerizations" European Journal of Organic Chemistry, 7924-7939 (2014).
Gauthier, C. et al., "Non-stoichiometric O-acetylation of Shigella flexneri 2a O-specific polysaccharide: synthesis and antigenicity", Organic & b_2013iomolecular chemistry 12, p. 4218-4232 (2014).
Heiss, C. et al., "Revised structures for the predominant O-polysaccharides expressed by Burkholderia pseudomallei and Burkholderia mallei", Carbohydrate research 381, p. 6-11 (2013).
Heiss, C., Burtnick, M. N., Black, I., Azadi, P. & Brett, P. J., "Detailed structural analysis of the O-polysaccharide expressed by Burkholderia thailandensis E264", Carbohydrate research 363, p. 23-28 (2012).
Ho, M. et al., "Specificity and functional activity of anti-Burkholderia pseudomallei polysaccharide antibodies" Infection and immunity 65, p. 3648-3653 (1997).
Jones, S., Ellis, J., Russell, P., Griffin, K. & Oyston, P., "Passive protection against Burkholderia pseudomallei infection In mice by monoclonal antibodies against capsular polysaccharide, lipopolysaccharide or proteins", Journal of medical microbiology, 51, p. 1055-1062 (2002).
Keluangkhot, V., Pethsouvanh, R. & Strobel, M., "Mélioïdose" Médecine et maladies infectieuses 35, p. 469-475 (2005).
Khan, I. et al., "Glanders in animals: a review on epidemiology, clinical presentation, diagnosis and countermeasures" Transboundary and emerging diseases 60, p. 204-221 (2013).
Knirel, Y. A. et al., "Structure of the polysaccharide chains of Pseudomonas pseudomallei lipopolysaccharides", Carbohydrate research 233, p. 185-193 (1992).
Lian, G., Zhang, X. & Yu, B., "Thioglycosides in carbohydrate research". Carbohydrate research 403, p. 13-22 (2015).
Love, K. R. & Seeberger, P. H., "Solution syntheses of protected type II Lewis blood group oligosaccharides: Study for automated synthesis", The Journal of organic chemistry 70, p. 3168-3177 (2005).
Love, K. R., Andrade, R. B. & Seeberger, P. H., "Linear synthesis of a protected H-type II pentasaccharide using glycosyl phosphate building blocks", The Journal of organic chemistry 66, p. 8165-8176 (2001).
Mukhopadhyay, B. & Field, R. A., "Convergent synthesis of a trisaccharide as its 2-(trimethylsilyl) ethyl glycoside related to the flavonoid triglycoside from Gymnema sylvestre", Carbohydrate research 341, p. 1697-1701 (2006).
Nashed, M. A. & Anderson, L., "Iodine as a reagent for the ready hydrolysis of prop-1-enyl glycosides, or their conversion into oxazolines", Journal of the Chemical Society, Chemical Communications, p. 1274-1276 (1982).

(56) References Cited

OTHER PUBLICATIONS

Neises, B. & Steglich, W., "Simple method for the esterification of carboxylic acids", Angewandte Chemie International Edition in English 17, p. 522-524 (1978).
Nelson, M. et al., "Evaluation of lipopolysaccharide and capsular polysaccharide as subunit vaccines against experimental melioidosis", Journal of medical microbiology 53, p. 1177-1182 (2004).
Ohara, K. et al., "Synthesis and Bioactivity of β-(1-→ 4)-Linked Oligomannoses and Partially Acetylated Derivatives", The Journal of organic chemistry 78, p. 6390-6411 (2013).
Oltvoort, J., Van Boeckel, C., De Koning, J. & Van Boom, J., "Use of the cationic iridium complex 1, 5-cyclooctadiene-bis [methyldiphenylphosphine]-iridium hexafluorophosphate in carbohydrate chemistry: Smooth isomerization of allyl ethers to 1-propenyl ethers", Synthesis 1981, p. 305-308 (1981).
Pearson, G. S., "The threat of deliberate disease in the 21st century", Biological Weapons Proliferation: Reasons for Concern, Courses of Action, 31 (1998).
Perry, M. B., MacLean, L. L., Schollaardt, T., Bryan, L. E. & Ho, M., "Structural characterization of the ipopolysaccharide O antigens of Burkholderia pseudomallei", Infection and Immunity, vol. 63, No. 9, p. 3348-3352 (1995).
Program, F. S. A. 2017 Annual Report of the Federal Select Agent Program. (2017).
Scott, A. E. et al., "Protection against experimental melioidosis following immunisation with a lipopolysaccharide-protein conjugate", Journal of immunology research 2014 (2014).
Suttisunhakul, V.; Wuthiekanun, V.; Brett, P. J.; Khusmith, S.; Day, N. P.; Burtnick, M. N.; Limmathurotsakul, D.; Chantratita, N., "Development of a rapid enzyme-linked immunosorbent assays for detection of antibodies to Burkholderia pseudomallei", J. Clin. Microbiol. 2016, 54, p. 1259-1268.
Tamigney Kenfack, M. et al., "Deciphering minimal antigenic epitopes associated with Burkholderia pseudomallei and Burkholderia mallei lipopolysaccharide O-antigens", Nature communications 8, 115, doi:10.1038/s41467-017-00173-8 (2017).
Tamigney Kenfack, M., Bleriot, Y. & Gauthier, C., "Intramolecular Aglycon Delivery Enables the Synthesis of 6-Deoxy-3-D-manno-heptosides as Fragments of Burkholderia pseudomallei and Burkholderia mallei Capsular Polysaccharide", The Journal of organic chemistry 79, p. 4615-4634 (2014).
Titball, R. W., Burtnick, M. N., Bancroft, G. J. & Brett, P., "Burkholderia pseudomallei and Burkholderia mallei vaccines: Are we close to clinical trials?" Vaccine 25, p. 5981-5989 (2017).
Treviño, S. R. et al., "Monoclonal antibodies passively protect BALB/c mice against Burkholderia mallei aerosol challenge", Infection and immunity 74, p. 1958-1961 (2006).
Wada, T., Ohkubo, A., Mochizuki, A. & Sekine, M., "2-(Azidomethyl) benzoyl as a new protecting group in nucleosides" Tetrahedron Letters 42, p. 1069-1072 (2001).
Wang, C.-C. et al., "Regioselective one-pot protection of carbohydrates", Nature 446, p. 896 (2007).
Zhang, S. et al., "In vitro and in vivo studies on monoclonal antibodies with prominent bactericidal activity against Burkholderia pseudomallei and Burkholderia mallei", Clinical and Vaccine Immunology (2011).

\* cited by examiner terminal residues / predominant intra-chain residues

*B. pseudomallei* (R = Ac)
*B. mallei* (R = H)

TETRASACCHARIDES FOR THE DIAGNOSIS, PREVENTION, AND TREATMENT OF MELIOIDOSIS AND GLANDERS

CROSS-REFERENCE TO RELATED APPLICATIONS

This application is a National Entry Application of PCT application no PCT/CA2020/050516 filed on Apr. 17, 2020 and published in English under PCT Article 21 (2), which itself claims benefit of U.S. provisional application Ser. No. 62/857,346, filed on Jun. 5, 2019. All documents above are incorporated herein in their entirety by reference.

FIELD OF THE INVENTION

The present invention relates to infectious diseases, and more particularly to the diagnosis, prevention and treatment of infectious diseases caused by *Burkholderia* infections, such as melioidosis and glanders.

BACKGROUND OF THE INVENTION

The use of biological agents to deliberately inflict death or diseases on civilians is seen as a serious threat in today's society, as technologies and expertise needed for the production of biological weapons are easily accessible and significantly cheaper than standard weapons.[1,2] The Centers for Disease Control and Prevention (CDC) regulate biological select agents or toxins (BSATs), which are considered to pose the highest threat to public, animal, and/or plant health. *Burkholderia pseudomallei* (Bp) and *Burkholderia mallei* (Bm), the respective etiologic agents of melioidosis and glanders, are found in endemic foci in Southeast Asia and Northern Australia, but have additionally been found sporadically worldwide.[3,4] These facultative intracellular, Gram-negative bacteria (GNB) have been classified as "Tier 1" BSATs[5] as a result of their ability to be effectively aerosolized, their high mortality rates (up to 50%), their laborious diagnosis, their intrinsic resistance to common antibiotics, and the current absence of licensed vaccines against them.[6-8] Moreover, Bm was reportedly used during World Wars I and II whereas the use of Bp as a bioweapon has been explored by the US and former Soviet Union.[9] All these facts highlight the relevance of working on the development of prophylactic measures and diagnostics against melioidosis and glanders infections.[10]

The treatment of melioidosis can currently be performed by the combination of many antibiotics for several weeks. However, not only does the prescribed treatment directly depends on the clinical manifestation of this polymorphic disease, making it particularly complex, but this type of treatment is also frequently unaffordable for developing countries where this disease is endemic.

Various experimental vaccines from attenuated strains of the bacterium or involving antigenic subunits have been developed in recent years, some of which being based on bacterial polysaccharides. Indeed, GNB such as Bp and Bm possess a variety of surface-exposed polysaccharides anchored in their outer membrane,[11] including capsule polysaccharide (CPS) and lipopolysaccharides (LPS), which have both recently been shown to be effective in animal models. LPS are known protective antigens and virulence factors (FIG. 1A). Studies have underlined the potential of using LPS as subunit vaccines owing to their stimulating effect on the adaptive immune system.[12] It was shown that LPS-specific monoclonal antibodies (mAbs) have the ability to passively protect animal models from infection,[13-18] and that immunization of mice with LPS conjugates induce significant protection against lethal challenges of Bp.[19,20]

The need to handle Bp and Bm in safety level 3 laboratories (BSL-3) complicates the preparation of large-scale vaccines against melioidosis and glanders. In addition, the difficulty of purifying surface polysaccharides and the risks of contamination and heterogeneity represent a major obstacle to their development.

The LPS O-antigens (OAgs) of Bp and Bm are of similar composition and consist of a linear heteropolymer whose repeating unit is a disaccharide of the following structure: [→3)-6-deoxy-α-L-talopyranosyl-(1→3)-β-D-glucopyranose-(1→] (FIG. 1B). One atypical characteristic of these OAgs lies in the non-stoichiometric methylation and acetylation pattern of the 6-deoxy-L-talose residue, which slightly varies between species, i.e., seven different patterns of acetylation/methylation are found within the native OAgs. It has been revealed that the predominant inner disaccharide unit of both Bp and Bm is acetylated at O-2. In addition, the terminal residue of Bm is 3-O-methylated and 2-O-acetylated whereas Bp's is also acetylated at O-4.[21-26]

SUMMARY OF THE INVENTION

In accordance with the present invention, there is provided:

1. A tetrasaccharide of formula I:

(I)

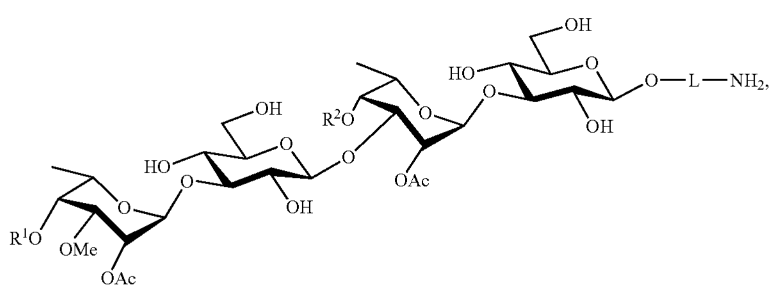

wherein:

Ac represents an acetyl ($CH_3—C(=O)—$) group,
Me represents a methyl group,
$R^1$ represents —H or an acetyl group
$R^2$ represents —H or an acetyl group, and
L represents a $C_2$-$C_6$ alkylene group, or -L- together with the oxygen atom to which it is attached forms 1 to 3 polyethylene glycol repeat units.

2. The tetrasaccharide of claim 1, wherein $R^1$ represents —H.

3. The tetrasaccharide of claim 1, wherein $R^1$ represents an acetyl group.

4. The tetrasaccharide of any one of claims 1 to 3, wherein $R^2$ represents —H.

5. The tetrasaccharide of any one of claims 1 to 4, wherein -L- represents a $C_2$-$C_6$ alkylene group, preferably a $C_5$ alkylene group.

6. A conjugate comprising the tetrasaccharide of any one of claims 1 to 5 and a molecule attached to the tetrasaccharide.

7. The conjugate of claim 6, wherein the molecule is a vaccine carrier molecule.

8. The conjugate of claim 7, wherein the vaccine carrier molecule is a protein carrier.

9. The conjugate of any one of claims 6 to 8, wherein the tetrasaccharide is attached to the molecule via its amine group.

10. The conjugate of claim 9, being of formula (II):

(II)

[Chemical structure: tetrasaccharide with R¹O, OMe, OAc, HO, OH, R²O, OAc, OH, HO, OH substituents and terminal O—L—NH—molecule]

wherein $R^1$, $R^2$, and L are as defined in claims 1 to 5.

11. A composition comprising the tetrasaccharide of any one of claims 1 to 5 or the conjugate of any one of claims 6 to 10.

12. The composition of claim 11, further comprising an excipient.

13. The composition of claim 11 or 12, being an immunogenic composition or a vaccine composition.

14. The composition of claim 13, further comprising a vaccine adjuvant.

15. A method for preventing a disease caused by a *Burkholderia* infection in a subject, the method comprising administering to the subject an effective amount of the tetrasaccharide of any one of claims 1 to 5, the conjugate of any one of claims 6 to 10, or the composition of any one of claims 11 to 14.

16. Use of the tetrasaccharide of any one of claims 1 to 5, the conjugate of any one of claims 6 to 10, or the composition of any one of claims 11 to 14 for preventing a disease caused by a *Burkholderia* infection in a subject 17. Use of the tetrasaccharide of any one of claims 1 to 5, the conjugate of any one of claims 6 to 10, or the composition of any one of claims 11 to 14 for the manufacture of a medicament for preventing a disease caused by a *Burkholderia* infection in a subject.

18. The tetrasaccharide of any one of claims 1 to 5, the conjugate of any one of claims 6 to 10, or the composition of any one of claims 11 to 14 for preventing a disease caused by a *Burkholderia* infection in a subject 19. A method for treating a disease caused by a *Burkholderia* infection in a subject, the method comprising administering to the subject an effective amount of the tetrasaccharide of any one of claims 1 to 5, the conjugate of any one of claims 6 to 10, or the composition of any one of claims 11 to 14.

20. Use of the tetrasaccharide of any one of claims 1 to 5, the conjugate of any one of claims 6 to 10, or the composition of any one of claims 11 to 14 for treating a disease caused by a *Burkholderia* infection in a subject.

21. Use of the tetrasaccharide of any one of claims 1 to 5, the conjugate of any one of claims 6 to 10, or the composition of any one of claims 11 to 14 for the manufacture of a medicament for treating a disease caused by a *Burkholderia* infection in a subject.

22. The tetrasaccharide of any one of claims 1 to 5, the conjugate of any one of claims 6 to 10, or the composition of any one of claims 11 to 14 for treating a disease caused by a *Burkholderia* infection in a subject.

23. A method for inducing the production of anti-*Burkholderia* antibodies in a subject, the method comprising administering to the subject an effective amount of the tetrasaccharide of any one of claims 1 to 5, the conjugate of any one of claims 6 to 10, or the composition of any one of claims 11 to 14.

24. Use of the tetrasaccharide of any one of claims 1 to 5, the conjugate of any one of claims 6 to 10, or the composition of any one of claims 11 to 14 for inducing the production of anti-*Burkholderia* antibodies in a subject.

25. Use of the tetrasaccharide of any one of claims 1 to 5, the conjugate of any one of claims 6 to 10, or the composition of any one of claims 11 to 14 for the manufacture of a medicament for inducing the production of anti-*Burkholderia* antibodies in a subject.

26. The tetrasaccharide of any one of claims 1 to 5, the conjugate of any one of claims 6 to 10, or the composition of any one of claims 11 to 14 for inducing the production of anti-*Burkholderia* antibodies in a subject 27. A method for diagnosing a *Burkholderia* infection in a subject, the method comprising contacting a sample from the subject with the tetrasaccharide of any one of claims 1 to 5; and detecting the presence or absence of complexes between the tetrasaccharide and antibodies present in the sample, wherein the presence of complexes is indicative the subject suffers from a *Burkholderia* infection.

28. A method for diagnosing a disease caused by a *Burkholderia* infection in a subject, the method comprising contacting a sample from the subject with the tetrasaccharide of any one of claims 1 to 5; and detecting the presence or absence of complexes between the tetrasaccharide and antibodies present in the sample, wherein the presence of complexes is indicative the subject suffers from a disease caused by a *Burkholderia* infection.

29. A method for detecting the presence or absence of antibodies specific for a *Burkholderia* bacterium in a sample from a subject, the method comprising contacting the sample with the tetrasaccharide of any one of claims 1 to 5; and detecting the presence or absence of complexes between the tetrasaccharide and antibodies present in the sample.

30. A kit for (i) diagnosing a *Burkholderia* infection or a disease caused by a *Burkholderia* infection in a subject; or (ii) detecting the presence or absence of antibodies specific for a *Burkholderia* bacterium in a sample from a subject, the kit comprising the tetrasaccharide of any one of claims 1 to 5.

31. The tetrasaccharide, use, method or kit of any one of claims 15-22 and 27-30, wherein the *Burkholderia* infection is an infection by *Burkholderia pseudomallei* (Bp) or *Burkholderia mallei* (Bm).

32. The tetrasaccharide, use, method or kit of claim 31, wherein the *Burkholderia* infection is an infection by *Burkholderia pseudomallei* (Bp).

33. The tetrasaccharide, use, method or kit of claim 31, wherein the *Burkholderia* infection is an infection by *Burkholderia mallei* (Bm).

34. The tetrasaccharide, use, method or kit of any one of claims 15-22, 28 and 30, wherein the disease is melioidosis or glander.

35. The tetrasaccharide, use, method or kit of claim 34, wherein the disease is melioidosis.

36. The tetrasaccharide, use, method or kit of claim 34, wherein the disease is glander.

37. The tetrasaccharide, use, or method of any one of claims 23-26, wherein the anti-*Burkholderia* antibodies are anti-*Burkholderia pseudomallei* (Bp) antibodies or anti-*Burkholderia mallei* (Bm) antibodies.

38. The tetrasaccharide, use, or method of claim 37, wherein the anti-*Burkholderia* antibodies are anti-*Burkholderia pseudomallei* (Bp) antibodies.

39. The tetrasaccharide, use, or method of claim 37, wherein the anti-*Burkholderia* antibodies are anti-*Burkholderia mallei* (Bm) antibodies.

40. A method for producing the tetrasaccharide of formula (I):

wherein $R^1$, $R^2$, and L are as defined above, the method comprising the steps of:
i. providing:
   a rhamnoside precursor of saccharides A and C with a methylphenylthio (STol) protecting group on the anomeric carbon, and
   a precursor of saccharide B with an STol protecting group on the anomeric carbon,
   a precursor of saccharide D,
ii. O-2 esterifying the precursor of saccharide B with 2-(azidomethyl)benzoic acid, thereby producing a (2-azidomethyl)benzoyl (AZMB)-protected precursor of saccharide B,
iii. O-2 acetylating and O-3 methylating, and then epimerizing a part of the rhamnoside precursor of saccharides A and C, thereby producing a precursor of saccharide A,
iv. O-2 acetylating the other part of the rhamnoside precursor of saccharides A and C, thereby producing a rhamnoside precursor of saccharide C,
v. glycosylating the rhamnoside precursor of saccharide C and the precursor of saccharide D, thereby producing a disaccharide,
vi. glycosylating the AZMB-protected precursor of saccharide B and the disaccharide, thereby producing a trisaccharide,
vii. glycosylating the precursor of saccharide A and the trisaccharide, thereby producing a tetrasaccharide,
viii. epimerizing saccharide C within the tetrasaccharide to produce the tetrasaccharide of formula (I); and
ix. removing the AZMB protective group.

41. The method of claim 40, wherein the precursor of saccharide B with an STol protecting group on the anomeric carbon is diol 17:

42. The method of claim 40 or 41, wherein the rhamnoside precursor of saccharides A and C with an STol protecting group on the anomeric carbon is alcohol 23:

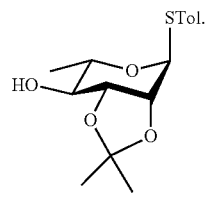

23

43. The method of any one of claims 40 to 42, wherein the precursor of saccharide D is acceptor 16:

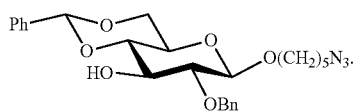

16

44. The method of any one of claims 40 to 43, comprising the steps of:

a) providing diol 17 as the precursor of saccharide B with an STol protecting group on the anomeric carbon, alcohol 23 as the rhamnoside precursor of saccharides A and C with an STol protecting group on the anomeric carbon, and acceptor 16 as the precursor of saccharide D:

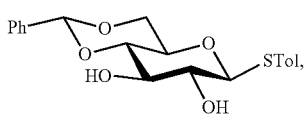

17

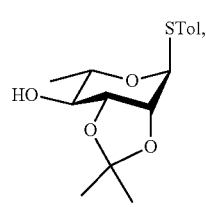

23 and

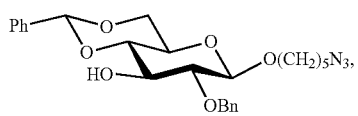

16 b) introducing a para-methoxybenzyl (PMB) group in O-3 on diol 17 through the formation of a stannylene acetal, thereby forming an alcohol, and esterifying the alcohol with 2-(azidomethyl)benzoic acid (AZMBOH), thereby producing donor 18:

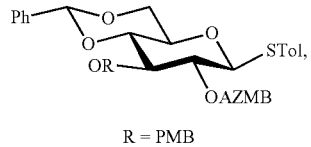

18

R = PMB c) levulinoylating alcohol 23 under the action of dicyclohexylcarbodiimide (DCC) and catalytic 4-dimethylaminopyridine (DMAP), and then cleaving isopropylidene in acidic media, thereby producing diol 24:

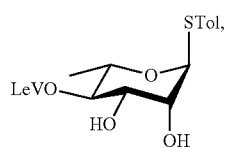

24 d) selectively alkylating a part of diol 24 at the O-3 position using tin acetal and then acetylating the remaining hydroxyl group, thereby producing donor 25:

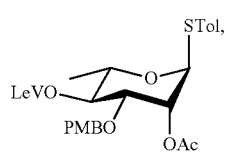

25 e) selectively alkylating the other part of diol 24 at the O-3 position using tin acetal and then acetylating the remaining hydroxyl group, thereby producing thiorhamnoside 29:

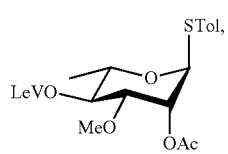

29 f) delevulinoylating thiorhamnoside 29, thereby producing intermediate 32:

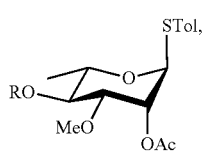

32

R = H g) carrying Pfitzner-Moffatt oxidation of intermediate 32, followed by reduction of the resulting crude ketone with $NaBH_4$, thereby producing thiotaloside 33:

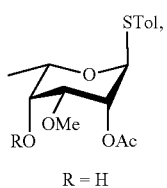

h) acetylating the remaining hydroxyl group of thiotaloside 33 using Ac$_2$O and catalytic DMAP, thereby producing thiotaloside 34 or protecting the remaining hydroxyl group of thiotaloside 33 with a chloroacetyl group, thereby producing thiotaloside 35:

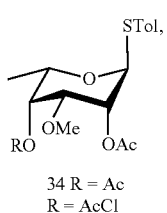

i) glycosylating donor 25 with acceptor 16 thereby producing disaccharide 26:

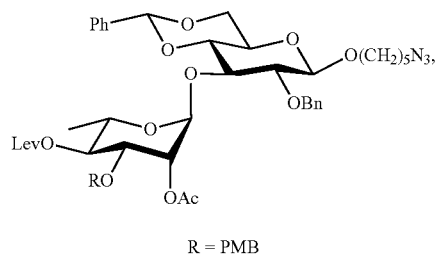

j) carrying PMB deprotection of disaccharide 26, thereby producing disaccharide acceptor 12:

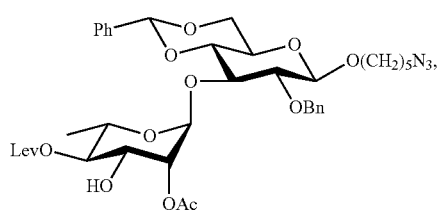

k) glycosylating disaccharide acceptor 12 with donor 18, thereby producing trisaccharide 27:

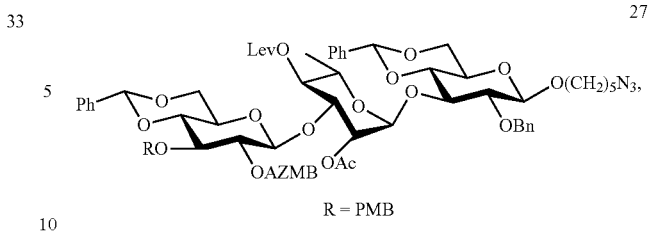

l) carrying 2,3-dichloro-5,6-dicyano-1,4-benzoquinone (DDQ)-mediated dealkylation of trisaccharide 27, thereby producing trisaccharide 28:

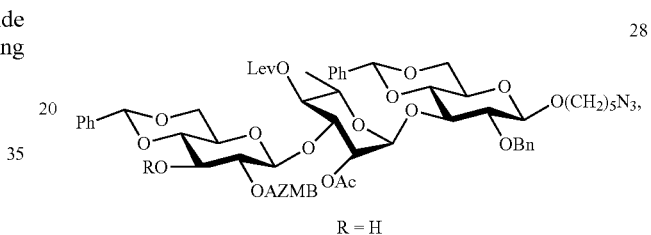

m) glycosylating trisaccharide acceptor 28 with thiotaloside 34 or thiotaloside 35, under previously mentioned conditions, thereby producing tetrasaccharide 36 or tetrasaccharide 37, respectively:

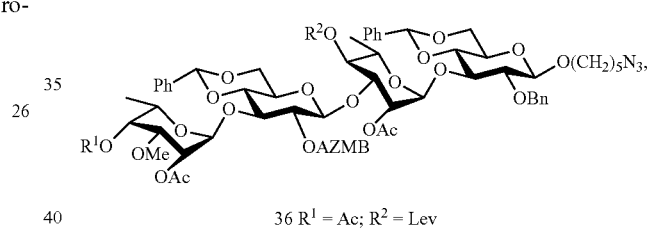

n) delevulinoylating tetrasaccharide 36 or tetrasaccharide 37, thereby producing tetrasaccharide 38 or tetrasaccharide 39, respectively:

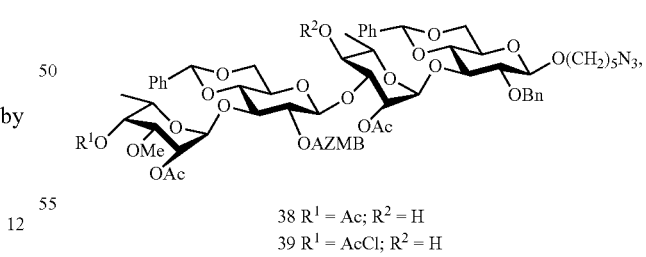

o) oxidating tetrasaccharide 38 using either Dess-Martin periodinane reagent or Pfitzner-Moffatt conditions, then reducing the resulting ketone into its talose configuration using NaBH4, thereby producing tetrasaccharide 40 or oxidating tetrasaccharide 39 using either Dess-Martin periodinane reagent or Pfitzner-Moffatt conditions, then reducing the resulting ketone into its talose configuration using NaBH₄, and then cleaving the chloroacetyl group, thereby producing tetrasaccharide 31:

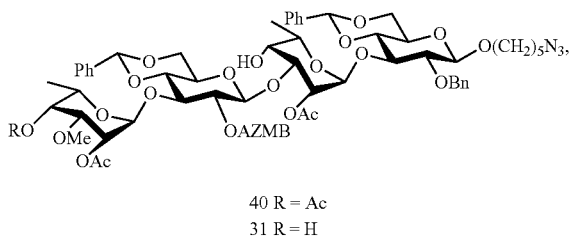

40 R = Ac
31 R = H and
p) deprotecting tetrasaccharide 40 or tetrasaccharide 31, thereby producing tetrasaccharide 8 or tetrasaccharide 9, respectively:

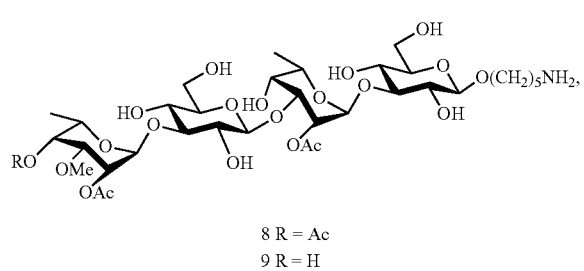

8 R = Ac
9 R = H wherein, in all of the above formulas,
Ph represents a phenyl group,
STol represents a methylphenylthio group,
AZMB represents an (2-azidomethyl)benzoyl group,
PMB represents a para-methoxybenzyl group,
Lev represents a levulinoyl group,
Ac represents an acetyl group,
Me represents a methyl group, and
AcCl represents a chloroacetyl group.

45. The method of claim 44, wherein the glycosylation in one or more, preferably all, of glycosylating steps i), k), and m) is N-Iodosuccinimide (NIS)/silver triflate (AgOTf)-promoted glycosylation.

46. The method of claim 44 or 45, wherein the deprotecting step p) comprises hydrogenolysing tetrasaccharide 40 or 31, thereby reducing the azides into amines and cleaving the Bn and benzylidene groups, thus producing tetrasaccharide 8 or 9.

47. The method of claim 44 or 45, wherein the deprotecting step p) comprises reducing the azides of tetrasaccharide 40 or 31 into amines, preferably using Staudinger reaction, and then hydrogenolysing the Bn and benzylidene groups, thus producing tetrasaccharide 8 or 9.

BRIEF DESCRIPTION OF THE DRAWINGS

In the appended drawings.

FIG. 2 (A) Structures of previously synthesized di- and trisaccharides (1-7) and (B) target synthetic tetrasaccharides 8 and 9 related to Bp and Bm LPS OAgs, respectively.

Figure 1A:
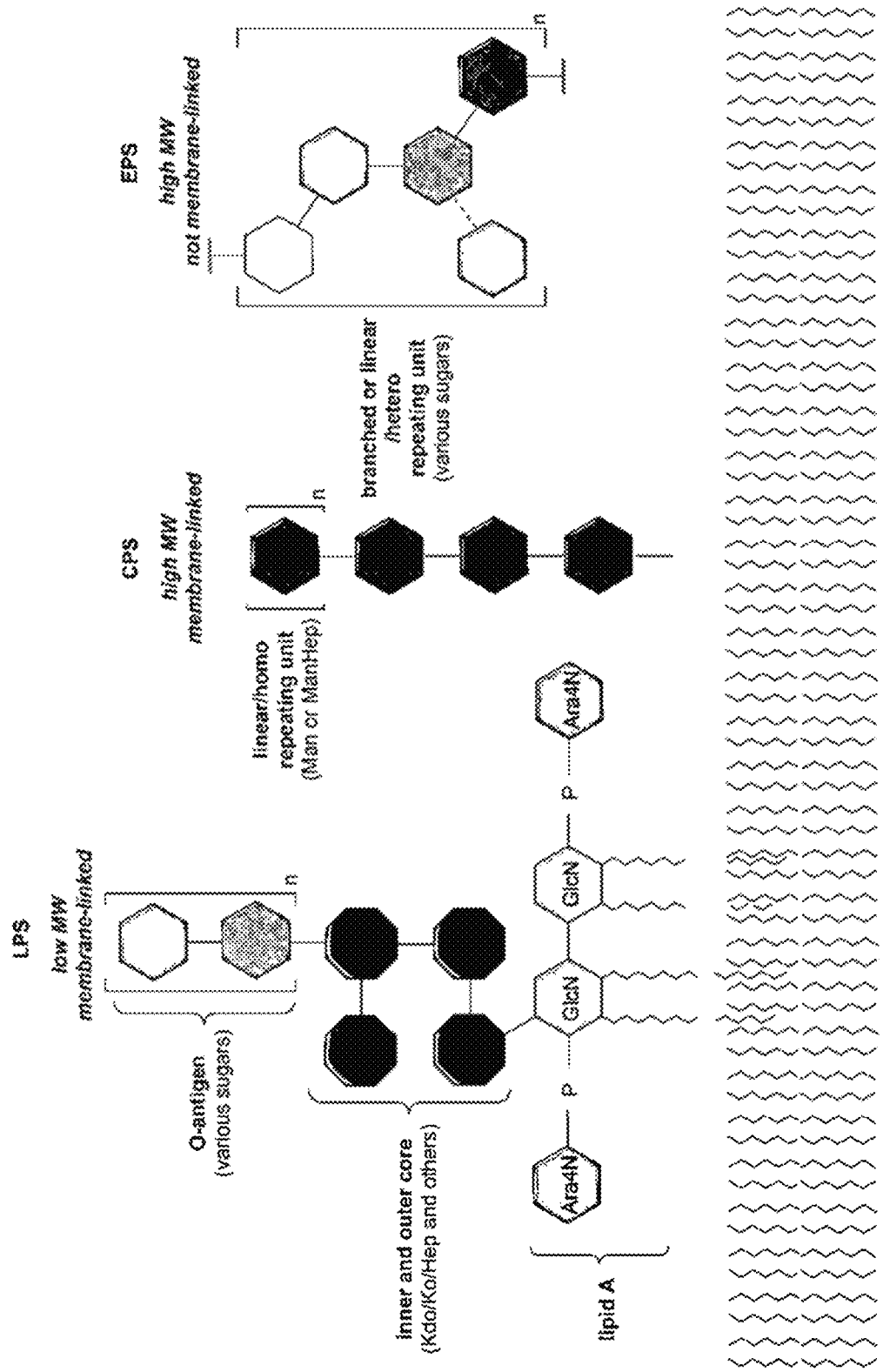
FIG. 1 (A) Schematic view of the main surface polysaccharides produced by *Burkholderia* spp. LPS: lipopolysaccharide; CPS: capsular polysaccharide; EPS: exopolysaccharide; Ara4N: 4-amino-4-deoxy-L-arabinose; GlcN: 2-amino-2-deoxy-D-glucose; Kdo: 3-deoxy-D-manno-oct-2-ulosonic acid; Ko: D-glycero-D-talo-oct-2-ulosonic acid; Man: D-mannose; ManHep: 6-deoxy-D-manno-heptose; Hep: heptose. and (B) Structures of *B. pseudomallei* and *B. mallei* LPS O-antigens showing the predominant terminal and intra-chain epitopes.
Figure 3:
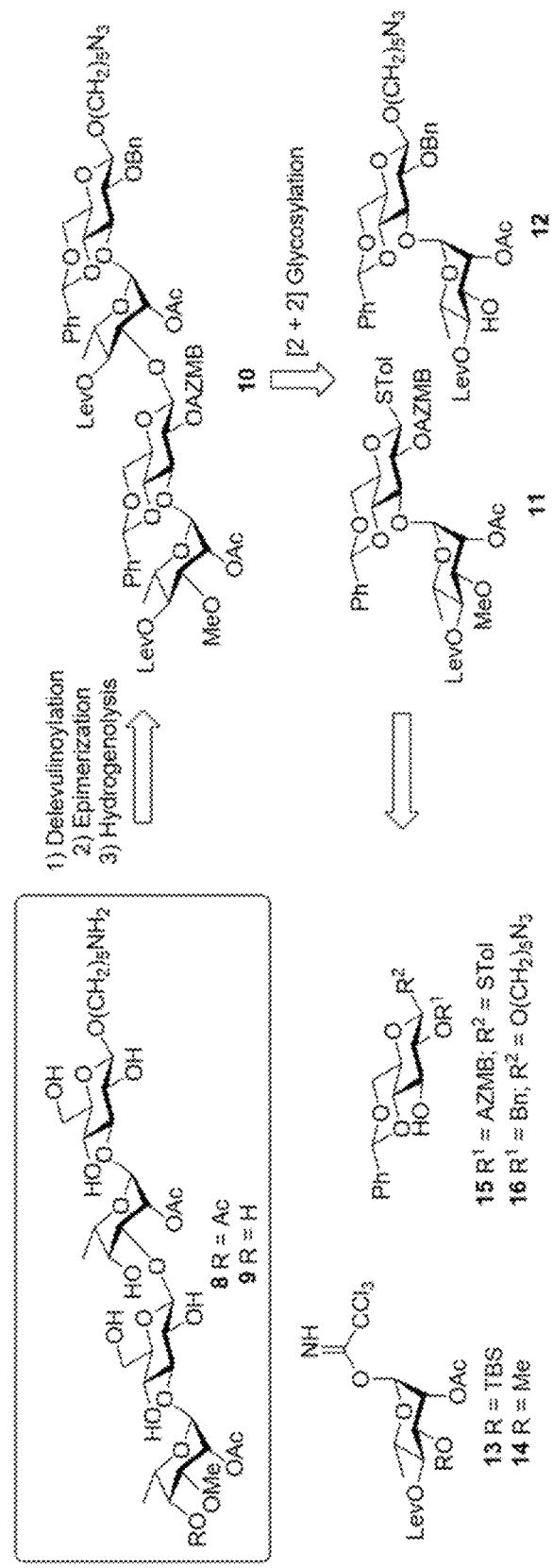
FIG. 3 Retrosynthesis analysis of target tetrasaccharides 8 and 9.

The presence of acetyl groups in the tetrasaccharide of formula (I) posed a substantial challenge in the development of the synthetic route, which had to be designed so that their migration or cleavage would be avoided. Thus, the present method must provide for the appropriate introduction of both the O-acetyl and O-methyl groups. This was complicated by the fact that the glycosylation required to attach the different saccharides into the desired tetrasaccharide made the acetyl unavailable as temporary protecting group.

Furthermore, the tetrasaccharide of formula (I) contains 6-deoxy-L-talose motifs (see the first and third groups from the left in formula (I), labelled saccharides "A" and "C" below). However, 6-deoxy-L-talose derivatives are not commercially available and thus other starting material should be used. Rhamnose derivatives have been selected for this purpose. Since rhamnose is an epimer of 6-deoxy-L-talose, the synthesis must include an epimerization step during which the rhamnose motifs are inverted into 6-deoxy-L-talose motifs.

However, such epimerization is liable to prevent the glycosylation required to attach the different saccharides into the desired tetrasaccharide. As such, it is conventionally preferred to carry out the rhamnose inversion after the required glycosylations. However, as shown in Example 1 below this approach did not work here. Another approach was thus necessary.

An approach based on methylphenylthio (STol) chemistry and the use of an azidomethylbenzoyl (AZMB) protecting group was developed.

In embodiments, this method for producing the tetrasaccharide of formula (I):

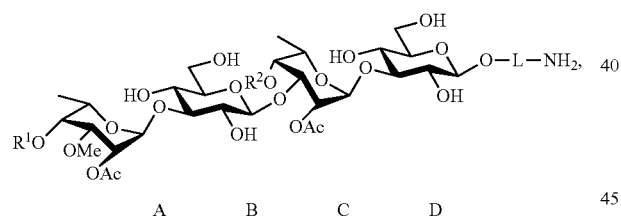

(I)

wherein $R^1$, $R^2$, and L are as defined above, comprises the steps of:
i. providing:
   a rhamnoside precursor of saccharides A and C with a methylphenylthio (STol) protecting group on the anomeric carbon, and
   a precursor of saccharide B with an STol protecting group on the anomeric carbon,
   a precursor of saccharide D,
ii. O-2 esterifying the precursor of saccharide B with 2-(azidomethyl)benzoic acid, thereby producing a (2-azidomethyl)benzoyl (AZMB)-protected precursor of saccharide B,
iii. O-2 acetylating and O-3 methylating, and then epimerizing a part of the rhamnoside precursor of saccharides A and C, thereby producing a precursor of saccharide A,
iv. O-2 acetylating the other part of the rhamnoside precursor of saccharides A and C, thereby producing a rhamnoside precursor of saccharide C, v. glycosylating the rhamnoside precursor of saccharide C and the precursor of saccharide D, thereby producing a disaccharide,
vi. glycosylating the AZMB-protected precursor of saccharide B and the disaccharide, thereby producing a trisaccharide,
vii. glycosylating the precursor of saccharide A and the trisaccharide, thereby producing a tetrasaccharide,
viii. epimerizing saccharide C within the tetrasaccharide to produce the tetrasaccharide of formula (I); and
ix. removing the AZMB protective group.

In embodiments, this method comprises the steps of:
a) providing diol 17 as the precursor of saccharide B with an STol protecting group on the anomeric carbon, alcohol 23 as the rhamnoside precursor of saccharides A and C with an STol protecting group on the anomeric carbon), and acceptor 16 as the precursor of saccharide D:

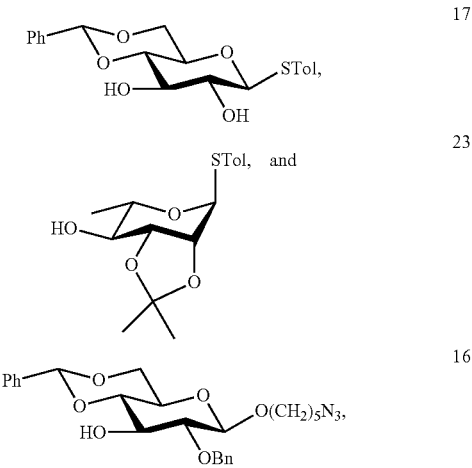

b) introducing a para-methoxybenzyl (PMB) group in O-3 on diol 17 through the formation of a stannylene acetal, thereby forming an alcohol, and esterifying the alcohol with 2-(azidomethyl)benzoic acid (AZMBOH), thereby producing donor 18:

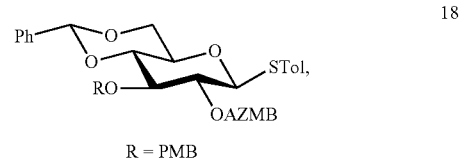

R = PMB c) levulinoylating alcohol 23 under the action of dicyclohexylcarbodiimide (DCC) and catalytic 4-dimethylaminopyridine (DMAP), and then cleaving isopropylidene in acidic media, thereby producing diol 24:

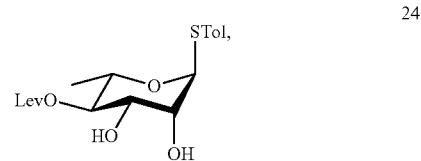

d) selectively alkylating a part of diol 24 at the O-3 position using tin acetal and then acetylating the remaining hydroxyl group, thereby producing donor 25:

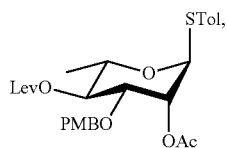

25 e) selectively alkylating the other part of diol 24 at the O-3 position using tin acetal and then acetylating the remaining hydroxyl group, thereby producing thiorhamnoside 29:

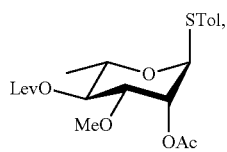

29 f) delevulinoylating thiorhamnoside 29, thereby producing intermediate 32:

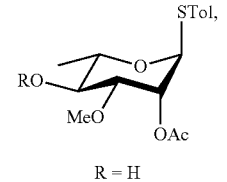

32

R = H g) carrying Pfitzner-Moffatt oxidation of intermediate 32, followed by reduction of the resulting crude ketone with NaBH$_4$, thereby producing thiotaloside 33:

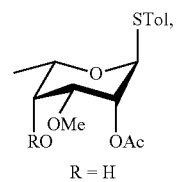

33

R = H h) acetylating the remaining hydroxyl group of thiotaloside 33 using Ac$_2$O and catalytic DMAP, thereby producing thiotaloside 34 or protecting the remaining hydroxyl group of thiotaloside 33 with a chloroacetyl group, thereby producing thiotaloside 35:

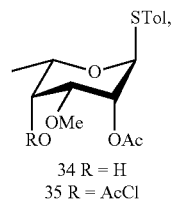

34 R = H
35 R = AcCl i) glycosylating donor 25 with acceptor 16 thereby producing disaccharide 26:

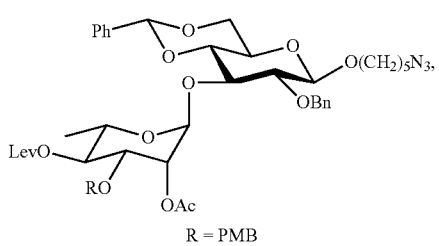

26

R = PMB j) carrying PMB deprotection of disaccharide 26, thereby producing disaccharide acceptor 12:

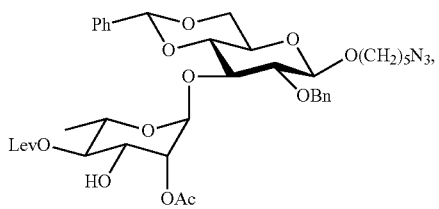

12 k) glycosylating disaccharide acceptor 12 with donor 18, thereby producing trisaccharide 27:

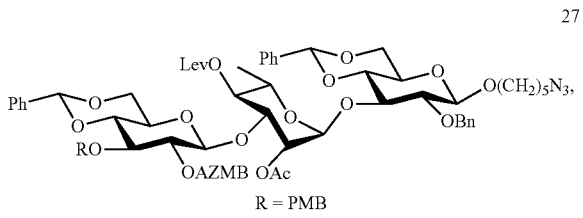

27

R = PMB l) carrying 2,3-dichloro-5,6-dicyano-1,4-benzoquinone (DDQ)-mediated dealkylation of trisaccharide 27, thereby producing trisaccharide 28:

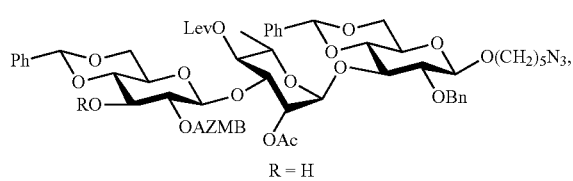

28

R = H m) glycosylating trisaccharide acceptor 28 with thiotaloside 34 or thiotaloside 35, under previously mentioned conditions, thereby producing tetrasaccharide 36 or tetrasaccharide 37, respectively:

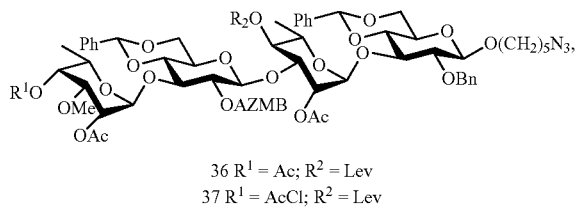

36 R$^1$ = Ac; R$^2$ = Lev
37 R$^1$ = AcCl; R$^2$ = Lev n) delevulinoylating tetrasaccharide 36 or tetrasaccharide 37, thereby producing tetrasaccharide 38 or tetrasaccharide 39, respectively:

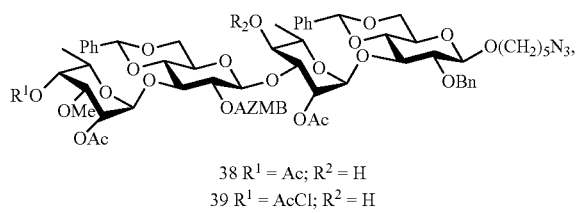

38 R$^1$ = Ac; R$^2$ = H
39 R$^1$ = AcCl; R$^2$ = H o) oxidating tetrasaccharide 38 using either Dess-Martin periodinane reagent or Pfitzner-Moffatt conditions, then reducing the resulting ketone into its talose configuration using NaBH$_4$, thereby producing tetrasaccharide 40
or
oxidating tetrasaccharide 39 using either Dess-Martin periodinane reagent or Pfitzner-Moffatt conditions, then reducing the resulting ketone into its talose configuration using NaBH$_4$, and then cleaving the chloroacetyl group, thereby producing tetrasaccharide 31:

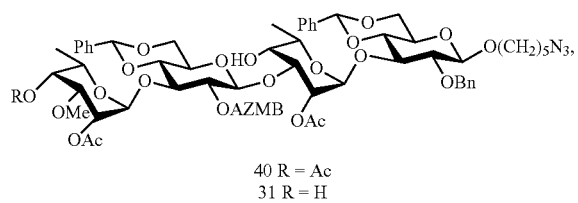

40 R = Ac
31 R = H and p) deprotecting tetrasaccharide 40 or tetrasaccharide 31, thereby producing tetrasaccharide 8 or tetrasaccharide 9, respectively:

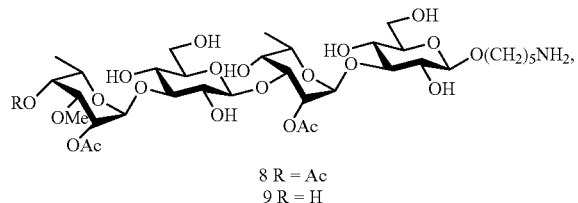

8 R = Ac
9 R = H wherein, in all of the above formulas,
Ph represents a phenyl group,
STol represents a methylphenylthio group,
AZMB represents an (2-azidomethyl)benzoyl group,
PMB represents a para-methoxybenzyl group,
Lev represents a levulinoyl group,
Ac represents an acetyl group,
Me represents a methyl group, and
AcCl represents a chloroacetyl group.

In embodiments, acceptor 16 can be provided by the method described in Tamigney Kenfack, M. et al. Deciphering minimal antigenic epitopes associated with *Burkholderia pseudomallei* and *Burkholderia mallei* lipopolysaccharide O-antigens. *Nature communications* 8, 115, doi: 10.1038/s41467-017-00173-8 (2017).

In embodiments, diol 17 and alcohol 23 can be provided by the method described in Ellervik, U., Grundberg, H. & Magnusson, G. Synthesis of lactam and acetamido analogues of sialyl Lewis X tetrasaccharide and Lewis X trisaccharide. *The Journal of organic chemistry* 63, 9323-9338 (1998).

In embodiments, the glycosylation in one or more, preferably all, of glycosylating steps i), k), and m) is N-Iodosuccinimide (NIS)/silver triflate (AgOTf)-promoted glycosylation.

In embodiments, deprotecting step p) comprises hydrogenolysing tetrasaccharide 40 or 31, thereby reducing the azides into amines and cleaving the Bn and benzylidene groups, thus producing tetrasaccharide 8 or 9.

In alternative embodiments, deprotecting step p) comprises reducing the azides of tetrasaccharide 40 or 31 into amines, preferably using Staudinger reaction, and then hydrogenolysing the Bn and benzylidene groups, thus producing tetrasaccharide 8 or 9.

Conjugates/Vaccines

In another aspect, the present disclosure provides a conjugate (or conjugate vaccine) comprising the tetrasaccharide of formula I described herein, and a molecule attached to the tetrasaccharide. The molecule may be any molecule useful to confer certain properties to the tetrasaccharide, such as a vaccine carrier molecule (protein carrier) that may be useful to increase the immunogenicity of the tetrasaccharide, or a detectable label that may be useful for detecting of anti-*Burkholderia* antibodies.

In embodiments, the conjugate (or conjugate vaccine) comprises the tetrasaccharide of formula I described herein and a vaccine carrier molecule, such as a protein carrier, attached to the tetrasaccharide. The term "protein carrier" as used herein refers to a protein that increases the immunogenicity of an antigen, particularly a weak antigen such as a polysaccharide. Such proteins are well known in the art, and include for example a genetically modified cross-reacting material (CRM) of diphtheria toxin (e.g., CRM$_{197}$), tetanus toxoid (TT), meningococcal outer membrane protein complex (OMPC), diphtheria toxoid (DT), and *H. influenzae* protein D (HiD) (see, e.g., Michael E Pichichero, Hum Vaccin Immunother. 2013 Dec. 1; 9(12): 2505-2523).

In preferred conjugates, the tetrasaccharide of formula I is attached to the abovementioned molecule/carrier protein via its amine group. Therefore, preferred conjugates include a conjugate of formula II:

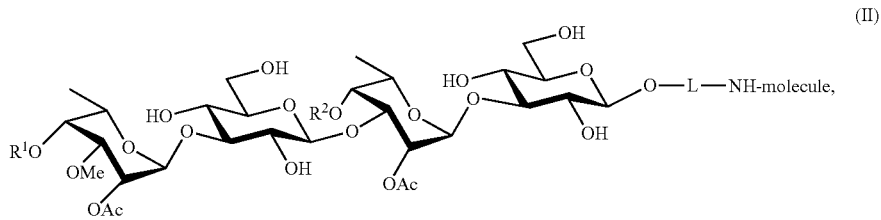

(II)

wherein R¹, R², and L are as defined above.

In another aspect, the present disclosure provides a composition comprising the tetrasaccharide of formula I or conjugate described herein. In an embodiment, the composition further comprises the tetrasaccharide of formula I or conjugate and an excipient, in a further embodiment a pharmaceutically acceptable excipient.

Such compositions may be prepared in a manner well known in the pharmaceutical art by mixing the tetrasaccharide or conjugate having a suitable degree of purity with one or more optional pharmaceutically acceptable excipients (see Remington: *The Science and Practice of Pharmacy*, by Loyd V Allen, Jr, 2012, 22$^{nd}$ edition, Pharmaceutical Press; *Handbook of Pharmaceutical Excipients*, by Rowe et al., 2012, 7$^{th}$ edition, Pharmaceutical Press). The excipient can be suitable for administration of the tetrasaccharide or conjugate by any conventional administration route, for example, for oral, intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration. In an embodiment, the excipient is adapted for administration of the tetrasaccharide or conjugate by the intravenous or subcutaneous route. In an embodiment, the excipient is adapted for administration of the tetrasaccharide or conjugate by the intravenous route. In another embodiment, the excipient is adapted for administration of the tetrasaccharide or conjugate by the subcutaneous route.

An "excipient" as used herein has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art, and the present composition is not limited in these respects. In certain embodiments, the composition described herein include excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive. Examples of commonly used excipient include water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

In an embodiment, the composition is an immunogenic or vaccine composition. In an embodiment, the composition comprising the tetrasaccharide of formula I or conjugate described herein further comprises a vaccine adjuvant. The term "vaccine adjuvant" refers to a substance which, when added to an immunogenic agent such as an antigen (e.g., the tetrasaccharide or conjugate defined herein), non-specifically enhances or potentiates an immune response to the agent in the host upon exposure to the mixture. Suitable vaccine adjuvants are well known in the art and include, for example: (1) mineral salts (aluminum salts such as aluminum phosphate and aluminum hydroxide, calcium phosphate gels), squalene, (2) oil-based adjuvants such as oil emulsions and surfactant based formulations, e.g., incomplete or complete Freud's adjuvant, MF59 (microfluidised detergent stabilised oil-in-water emulsion), QS21 (purified saponin), AS02 [SBAS2] (oil-in-water emulsion+MPL+QS-21), (3) particulate adjuvants, e.g., virosomes (unilamellar liposomal vehicles incorporating influenza haemagglutinin), ASO4 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), complete Freud's adjuvant (comprising inactivated and dried mycobacteria) (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles.

Methods of Diagnosing, Preventing or Treating Diseases Caused by a *Burkholderia* Infection In another aspect, the present disclosure provides a method for preventing a disease caused by a *Burkholderia* infection in a subject, the method comprising administering to the subject an effective amount of the above tetrasaccharide of formula I, conjugate or composition (e.g., vaccine composition) described herein. In another aspect, the present disclosure provides the use of the tetrasaccharide of formula I, conjugate or composition (e.g., vaccine composition) described herein for preventing a disease caused by a Burkholderia infection in a subject. In another aspect, the present disclosure provides the use of the tetrasaccharide of formula I, conjugate or composition (e.g., vaccine composition) described herein for the manufacture of a medicament for preventing a disease caused by a *Burkholderia* infection in a subject. In another aspect, the present disclosure provides the tetrasaccharide of formula I, conjugate or composition (e.g., vaccine composition) described herein for preventing a disease caused by a *Burkholderia* infection in a subject.

The term "preventing" as used herein refers to the administration of the tetrasaccharide, conjugate or composition prior to the *Burkholderia* infection, or prior to the development of the disease (prophylactic administration), for preventing the development of the disease, delaying the development of the disease, and/or reducing the symptoms or severity of the disease.

In another aspect, the present disclosure provides a method for treating a disease caused by a *Burkholderia* infection in a subject, the method comprising administering to the subject an effective amount of the tetrasaccharide of formula I, conjugate or composition (e.g., vaccine composition) described herein. In another aspect, the present disclosure provides the use of the tetrasaccharide of formula I, conjugate or composition (e.g., vaccine composition) described herein for treating a disease caused by a *Burkholderia* infection in a subject. In another aspect, the present disclosure provides the use of the tetrasaccharide of formula I, conjugate or composition (e.g., vaccine composition) described herein for the manufacture of a medicament for treating a disease caused by a *Burkholderia* infection in a subject. In another aspect, the present disclosure provides the tetrasaccharide of formula I, conjugate or composition (e.g., vaccine composition) described herein for treating a disease caused by a *Burkholderia* infection in a subject.

In another aspect, the present disclosure provides a method for inducing the production of anti-*Burkholderia* antibodies in a subject, the method comprising administering to the subject an effective amount of the tetrasaccharide of formula I, conjugate or composition (e.g., vaccine composition) described herein. In another aspect, the present disclosure provides the use of the tetrasaccharide of formula I, conjugate or composition (e.g., vaccine composition) described herein for inducing the production of anti-*Burkholderia* antibodies in a subject. In another aspect, the present disclosure provides the use of the tetrasaccharide of formula I, conjugate or composition (e.g., vaccine composition) described herein for the manufacture of a medicament for inducing the production of anti-*Burkholderia* antibodies in a subject. In another aspect, the present disclosure provides the tetrasaccharide of formula I, conjugate or composition (e.g., vaccine composition) described herein for inducing the production of anti-*Burkholderia* antibodies in a subject.

The term "treating" as used herein refers to the administration of the tetrasaccharide, conjugate or composition after the *Burkholderia* infection, or after the development of the disease (therapeutic administration), for reducing the symptoms or severity of the disease, preventing complications related to the disease, and/or reversing the pathology and/or symptomatology.

In an embodiment, the *Burkholderia* infection is an infection by *Burkholderia pseudomallei* (Bp) or *Burkholderia mallei* (Bm). In an embodiment, the disease is melioidosis or glanders.

Any suitable amount of the tetrasaccharide, conjugate or composition may be administered to a subject. The dosages will depend on many factors including the mode of administration. Typically, the amount of tetrasaccharide, conjugate or composition contained within a single dose will be an amount that effectively prevent the disease without inducing significant toxicity.

For the prevention or treatment of a given disease or condition, the appropriate dosage of the tetrasaccharide, conjugate or composition will depend on the type of disease or condition to be prevented/treated, previous therapy, the patient's clinical history and response to the tetrasaccharide, conjugate or composition, and the discretion of the attending physician. The tetrasaccharide, conjugate or composition is suitably administered to the subject at one time or over a series of treatments. Preferably, it is desirable to determine the dose-response curve in vitro, and then in useful animal models prior to testing in humans.

In another aspect, the present disclosure provides a method for diagnosing a *Burkholderia* infection in a subject, the method comprising contacting a sample from the subject with the tetrasaccharide of formula I described herein; and detecting the presence or absence of complexes between the tetrasaccharide and antibodies present in the sample, wherein the presence of complexes is indicative the subject suffers from a *Burkholderia* infection (and the absence of complexes is indicative the subject does not suffer from a *Burkholderia* infection).

In another aspect, the present disclosure provides a method for diagnosing a disease caused by a *Burkholderia* infection in a subject, the method comprising contacting a sample from the subject with the tetrasaccharide of formula I described herein; and detecting the presence or absence of complexes between the tetrasaccharide and antibodies present in the sample, wherein the presence of complexes is indicative the subject suffers from a disease caused by a *Burkholderia* infection (and the absence of complexes is indicative the subject does not suffer from a disease caused by a *Burkholderia* infection).

In another aspect, the present disclosure provides a method for detecting the presence or absence of antibodies specific for a *Burkholderia* bacterium in a sample from a subject, the method comprising contacting the sample with the tetrasaccharide of formula I described herein; and detecting the presence or absence of complexes between the tetrasaccharide and antibodies present in the sample.

Examples of methods to detect proteins (antibodies) in a sample include, but are not limited to: Western blot, immunoblot, enzyme-linked immunosorbent assay (ELISA), "sandwich" immunoassays, radioimmunoassay (RIA), immunoprecipitation, and surface plasmon resonance (SPR). In an embodiment, the presence or absence of antibodies in the sample is determined by ELISA.

In an embodiment, the tetrasaccharide of formula I is detectably labelled, i.e. comprises a detectable label attached thereto, to facilitate the detection of the tetrasaccharide/antibody complexes. As used herein, the term "detectable label" refers to a moiety emitting a signal (e.g., light) that may be detected using an appropriate detection system. Any suitable detectable label may be used in the method described herein. Detectable labels include, for example, enzyme or enzyme substrates (e.g., horseradish peroxidase (HRP), alkaline phosphatase (AP)), reactive groups, chromophores such as dyes or colored particles, luminescent moieties including bioluminescent, phosphorescent or chemiluminescent moieties, and fluorescent moieties.

In another embodiment, the detection of the tetrasaccharide/antibody complexes is performed using a detectably labelled secondary antibody, e.g., an antibody capable of binding to the antibodies from the sample bound to the tetrasaccharide, for example a detectably labelled anti-IgG antibody.

The sample used in the methods may be any sample susceptible to contain antibodies specific for a *Burkholderia* bacterium in a subject infected by the *Burkholderia* bacterium. In an embodiment, the sample is a blood sample or blood-derived sample, such as a plasma or serum sample. The sample may be a crude sample, or a sample subjected to one or more purification/enrichment steps. The sample may be a fresh sample, or a previously frozen sample.

In another aspect, the present disclosure provides a kit for (i) diagnosing a *Burkholderia* infection or a disease caused by a *Burkholderia* infection in a subject; or (ii) detecting the presence or absence of antibodies specific for a *Burkholderia* bacterium in a sample from a subject, the kit comprising the tetrasaccharide of formula I described herein. The kit may further comprise reagents for detecting the presence or absence of complexes between the tetrasaccharide and antibodies present in the sample, such as a secondary antibody, enzymatic substrates, buffers, etc.

As used herein, the term "subject" is taken to mean warm blooded animals such as mammals, for example, cats, dogs, mice, guinea pigs, horses, bovine cows, sheep and humans. In an embodiment, the subject is a mammal, and more particularly a human.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure, such as Formula 1, with various substituents ($R_1$, $R_2$, etc.) and various radicals (e.g. alkyl) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1

We recently described the synthesis of seven di- and trisaccharides (1-7) mimicking all of the reported substitution patterns of Bp and Bm OAgs (FIG. 2A).[27] Enzyme-linked immunosorbent assay (ELISA), saturation transfer difference (STD)-nuclear magnetic resonance (NMR) and surface plasmon resonance (SPR) assays were jointly used to assess the molecular interactions of the synthetic oligosaccharides against LPS-specific mAbs. These biophysical studies revealed the role of the capping 3-O-methylated-6-deoxy-L-talose residues in the binding process. Moreover, we showed that high-titer antibody responses can be raised in mice injected with a CRM197:Bm-like disaccharide 6 construct and that these responses were cross-reactive with Bm-like LPS. In contrast, a CRM197: Bp-like disaccharide 7 construct was not able to induce a strong antibody response in both BALB/c and C57BL/6 mice suggesting a gap in the mice B cell repertoire against the OAg motif bearing an additional 4-O-acetyl group. We also showed that Thai melioidosis patient serum samples can react with Bp-like disaccharide 7, as well as trisaccharide 2, which indicates that, unlike mice, humans can generate mAb responses against this unique OAg epitope. In fact, the antigenicity tests with the blood of patients with melioidosis showed some recognition of synthetic oligosaccharides, but at significantly lower levels than native LPS.

We now show that longer oligosaccharidic fragments, such as tetrasaccharides 8 and 9 (FIG. 2B), bearing both internal and terminal epitopes of Bp and Bm OAgs are suitable for the development of diagnostics and subunit vaccines against melioidosis and glanders. We herein describe a synthetic approach enabling the preparation of tetrasaccharides related to Bp and Bm LPS OAg featuring the main intrachain and terminal acetylation and methylation patterns. The reactivity profiles of synthetic oligosaccharides 1-9 were assessed against Thai melioidosis patient serum samples highlighting that tetrasaccharides 8 and 9 act as exquisite mimics of the whole Bp and Bm LPS OAgs.

Retrosynthetic Approach

The presence of acetyl groups in target tetrasaccharides 8 and 9 posed a substantial challenge in the development of the synthetic route, which had to be designed so that their migration or cleavage would be avoided. Retrosynthetic analysis of these oligosaccharides, as depicted in FIG. 3, led to the identification of synthons 13, 14,[27] 15, and 16[27] as the most readily accessible functionalized monosaccharides that could enable their assembly. Our synthetic approach would be based on a convergent [2+2] glycosylation strategy in which disaccharides 11 and 12, assembled from building blocks 13-16, would be coupled into fully protected tetrasaccharide 3, the latter being a precursor of both Bp- and Bm-like oligosaccharides 8 and 9, respectively. We planned to introduce O-acetyl and O-methyl groups in synthons 13 and 14 prior to the synthesis of the tetrasaccharides. These building blocks would be designed to preserve orthogonality among the temporary protecting groups and acetates. The acetyl groups at O-2 on rhamnosides 13 and 14 as well as the (2-azidomethyl)benzoyl (AZMB) group of glucoside 15 would act as neighbouring participating group (NPG) to ensure the stereoselective formation of 1,2-trans glycosidic linkages in the target compounds. Moreover, assisted cleavage of the AZMB group, which involves the reduction of the primary azide into the corresponding amine followed by in situ intramolecular cyclization into an isoindolinone, thereby releasing the C2 hydroxyl group,[28-30] would be achieved during the final hydrogenolysis step. The anomeric position of monosaccharides 13 and 14 would be activated with a trichloroacetimidate (TCA) leaving group in an attempt to achieve high-yielding couplings, as previously reported for structurally similar L-rhamnose donors.[31] In contrast, glucoside 15 would be thiolated at the anomeric position to ensure its orthogonal glycosylation with respect to donor 14. The methylphenylthio (STol) group is known to be highly stable under a broad variety of conditions while being readily accessible from peracetylated sugars,[32] and thioglucoside 15 would be converted into other donors in the event that the coupling proves ineffective.

As 6-deoxy-L-talose derivatives are not commercially available, rhamnosides 13 and 14 would be instead employed. We envisioned to conduct both C4 epimerization simultaneously at a later stage of the synthetic route via a two-step oxidation/reduction sequence. To reach Bp-like tetrasaccharide 8, we intended to take advantage of the steric hindrance surrounding the inner 6-deoxy-L-talose residue to acetylate regioselectivity the O-4 position of the non-reducing end residue. Finally, acceptor 16 would be equipped with an azidolinker at C1, which upon reduction would allow the coupling of the fully assembled, unprotected oligosaccharides to activated ELISA plates enabling antigenicity assays with serum samples and/or covalent coupling with carrier proteins.

First Generation Synthesis of Tetrasaccharides—Unsuccessful

Figure 4:
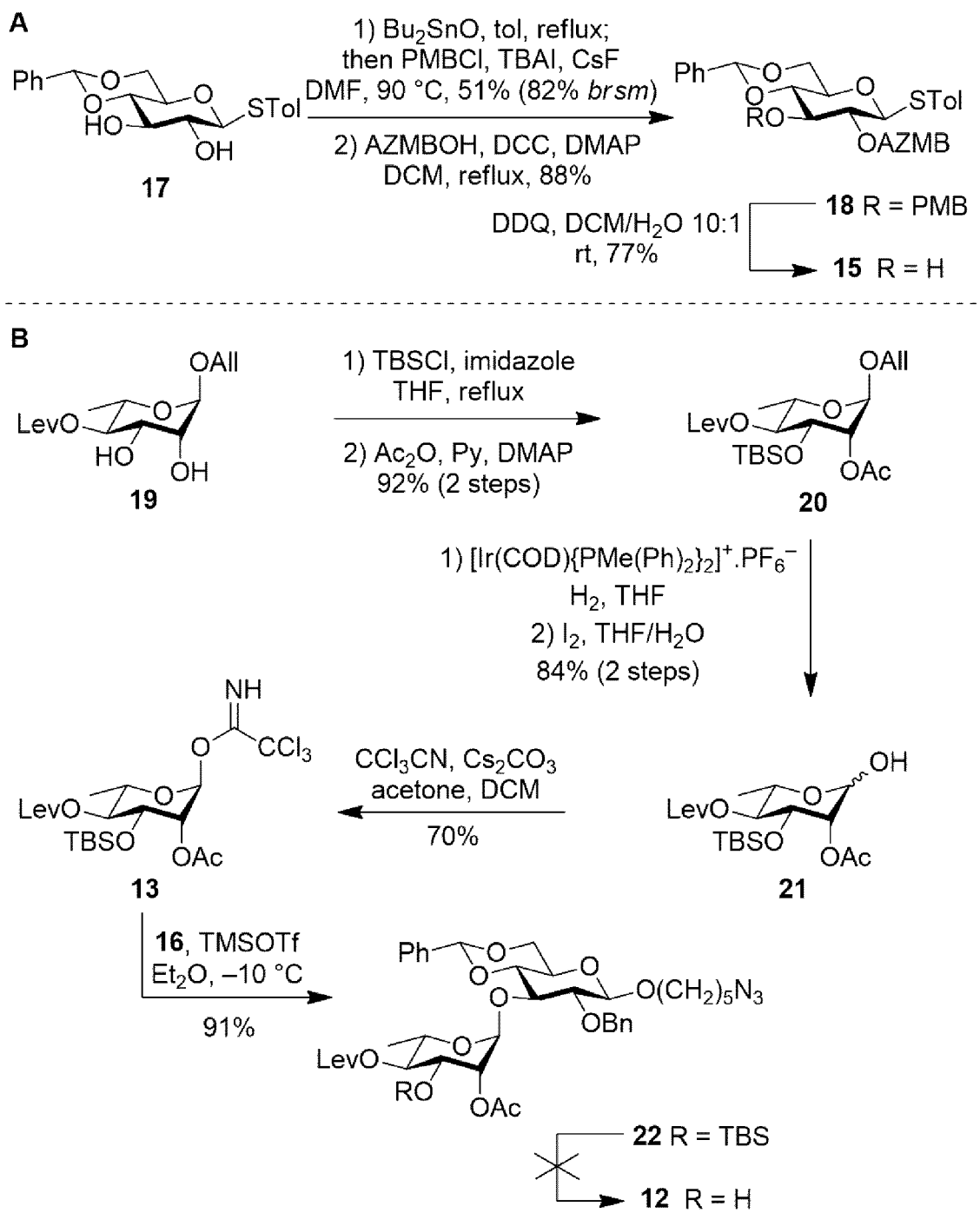
FIG. 4 (A) Synthesis of 2-O-AZMB-containing glucose derivative 15; (B) Failed attempt to synthesize disaccharide 12.

As depicted in FIG. 4, the synthesis of glucoside acceptor 15 was performed in three steps from known diol 17.[33] A para-methoxybenzyl (PMB) group was selectively introduced at O-3 through the formation of a stannylene acetal. This step was followed by esterification of the resulting alcohol[34] with 2-(azidomethyl)benzoic acid (AZMBOH), which was prepared using Steglich conditions.[31,35] This yielded donor 18. The PMB group finally underwent oxidative cleavage using 2,3-dichloro-5,6-dicyano-1,4-benzoquinone (DDQ), furnishing acceptor 15.

Allyl rhamnoside 19[27] was used as starting material for the preparation of TCA 13. Imidazole was used as catalyst for the selective protection of the C3 hydroxyl with a tert-butyldimethylsilyl (TBS) group and the remaining free OH was acetylated under standard conditions, yielding rhamnoside 20 in 92% yield over two steps. Allyl isomerization into the corresponding 1-propenyl ether was accomplished using an iridium-based catalyst[36,37] and was followed by its hydrolysis using iodine[38] in a mixture of THF and water. Resulting hemiacetal 21 was successfully converted into TCA 13 (~9:1α/β mixture) through a standard procedure involving trichloroacetonitrile and cesium carbonate. The latter was coupled with acceptor 16 under the promotion of trimethylsilyl trifluoromethanesulfonate (TMSOTf), providing disaccharide 22 in an excellent 91% yield as the sole α-anomer. In order to lengthen the disaccharide, deprotection of the TBS group was attempted using $Et_3N·3HF$ under microwave radiation, but acetyl cleavage was unfortunately observed. Tetra-n-butylammonium fluoride (TBAF)-mediated cleavage, with and without acetic acid buffer, also led to acetyl deprotection.

Figure 5:
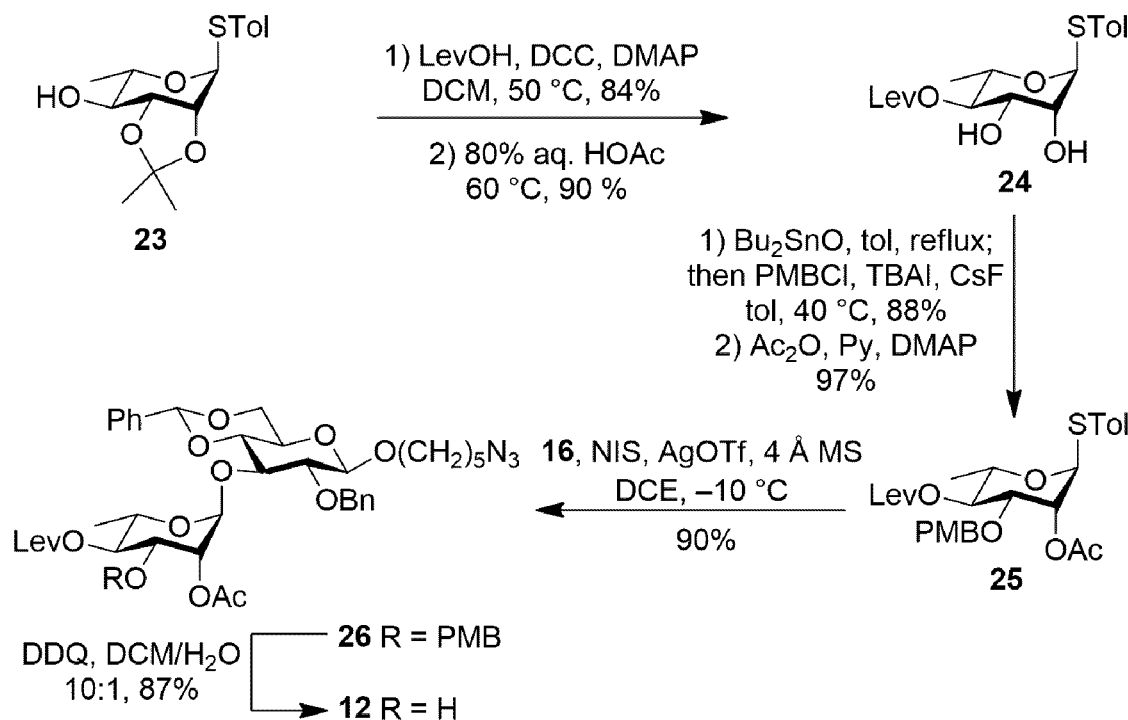
FIG. 5 Synthesis of disaccharide acceptor 12.

To circumvent this problem, thiorhamnoside 25 was prepared, bearing an orthogonal PMB group at O-3 instead of a TBS group (FIG. 5). Alcohol 23[39] was therefore levulinoylated under the action of dicyclohexylcarbodiimide (DCC) and catalytic DMAP, and the isopropylidene was cleaved in acidic media, furnishing diol 24 in excellent yield. Tin acetal chemistry was taken advantage of for the selective alkylation of the O-3 position and the remaining hydroxyl group was acetylated into donor 25. N-Iodosuccinimide (NIS)/silver triflate (AgOTf)-promoted glycosylation of the latter with acceptor 16 at 10° C. in DCE provided disaccharide 26 in 90% yield. Satisfyingly, only the α-anomer was formed, which was then successfully transformed into acceptor 12 following PMB deprotection.

Figure 6:
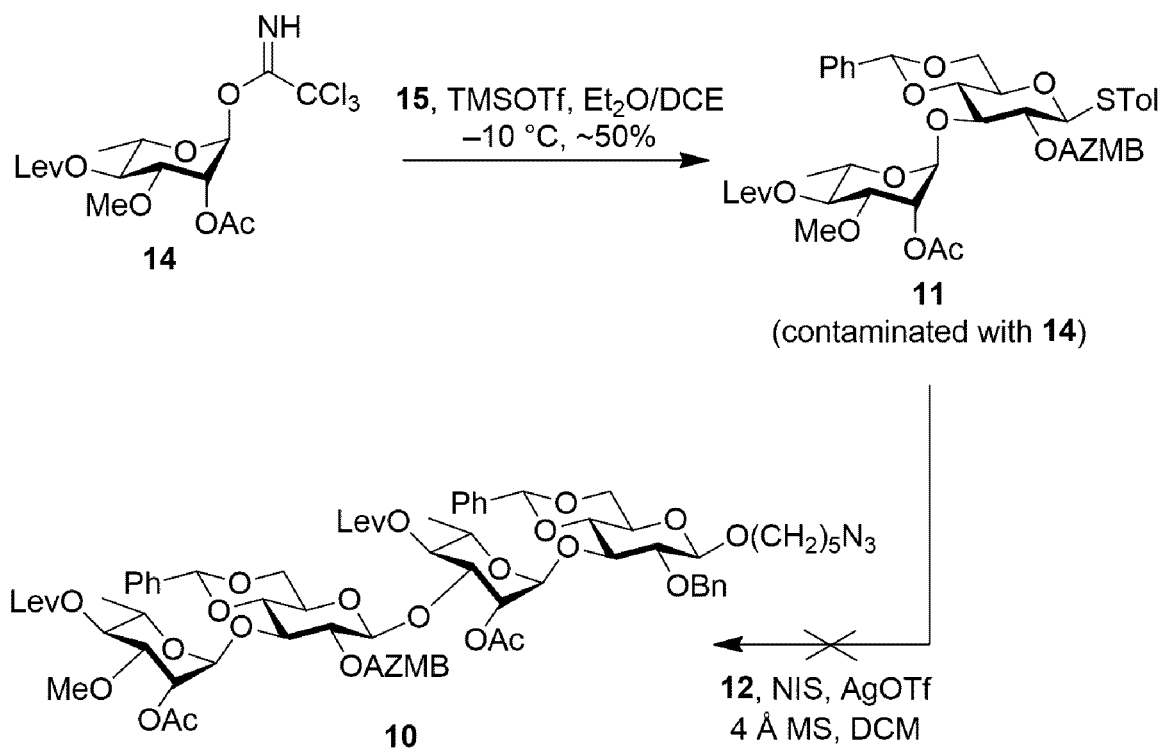
FIG. 6 Attempts to synthesize tetrasaccharide 10 via icking the functional epitope of native polysaccharides without the use of pathogenic bacteria.

Planning on employing a [2+2] glycosylation strategy (FIG. 6), disaccharide 11 was then prepared through TMSOTf-promoted glycosylation of TCA 7[27] and acceptor 15. However, complete conversion could not be achieved and disaccharide 11 was contaminated with donor 14 even upon extensive column chromatography purification. Synthesis of fully protected tetrasaccharide 10 was nonetheless attempted using NIS/AgOTf but proved unsuccessful, as NMR analysis showed no sign of the expected glycosidic bond.

Second Generation Synthesis of Tetrasaccharides—Unsuccessful

Figure 7:
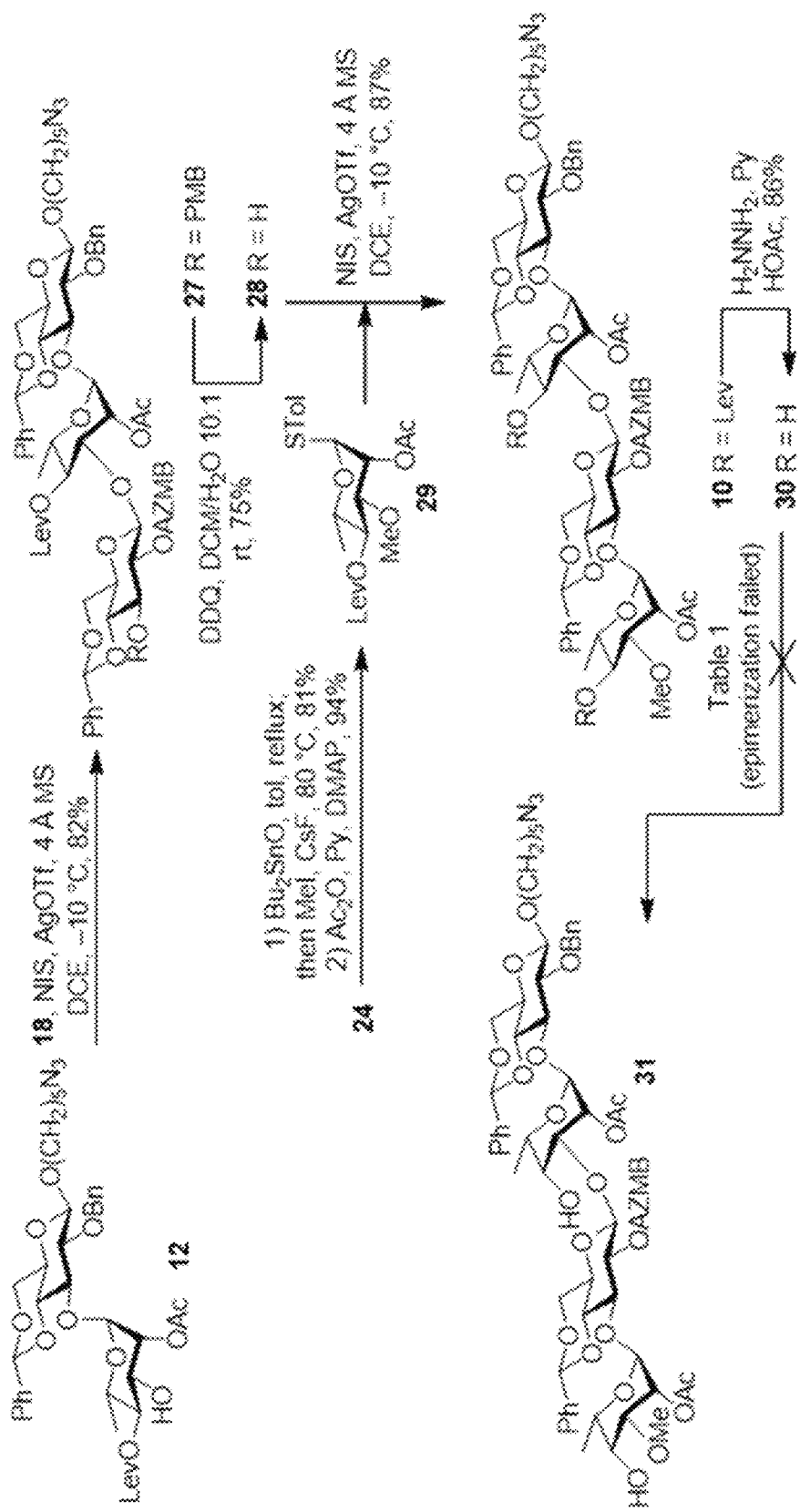

As our previously envisioned methodology appeared ineffective, we chose to focus our attention on an alternative sequential [1+1+1+1] glycosylation pathway (FIG. 7). First, disaccharide acceptor 12 was glycosylated with donor 18 using the aforementioned conditions, yielding trisaccharide 27. The AZMB group appeared to be an efficient NPG, as the β-anomer was exclusively formed. DDQ-mediated dealkylation of trisaccharide 27 enabled its coupling with thiorhamnoside 29, which was prepared from intermediate 24 through a methodology similar as the one used for donor 25. Pleasingly, anomerically pure tetrasaccharide 10 was produced in 87% yield. To achieve the desired 6dTalp configuration, the levulinoyl groups were selectively cleaved under the action of hydrazine and epimerization of both free hydroxyl groups was attempted. Our strategy was based on an oxidation step (Table 1) followed by a stereoselective reduction using $NaBH_4$ in a mixture of MeOH and DCM. Pfitzner-Moffatt oxidation[40] (entry 1) was first tried since we previously showed that this condition was high-yielding for similar substrates,[27] nevertheless complete degradation of the starting material was observed. The same reaction was conducted at −78° C. (entry 2) with the hope of stabilizing the reactive intermediate formed between phenyl dichlorophosphate (PDCP) and DMSO, but without success. Substituting the PDCP reagent with oxalyl chloride also gave no conversion (entry 3). Other oxidation reactions were carried out using DMSO and Ac$_2$O at room temperature (entry 4) or Dess-Martin periodinane at reflux[27] (entry 5), but both failed to provide clean oxidation products.

TABLE 1

Unsuccessful attempts to epimerize tetrasaccharide 23.

| Entry | Oxidation Reagents | Solvent | Temperature (° C.) | Yield (%) |
|---|---|---|---|---|
| 1 | DMSO, PDCP, Et$_3$N | DCM | −10 to rt | nd[a] |
| 2 | DMSO, PDCP, Et$_3$N | DCM | −78 to rt | nd[b] |
| 3 | Oxalyl chloride, DMSO, Et$_3$N | DCM | −78 | nd[b] |
| 4 | DMSO, Ac$_2$O | — | rt | nd[b] |
| 5 | Dess-Martin periodinane | DCE | reflux | nd[b] |

[a]Degradation of starting material.
[b]No reaction.

Third Generation Synthesis of Tetrasaccharides

Figure 8:
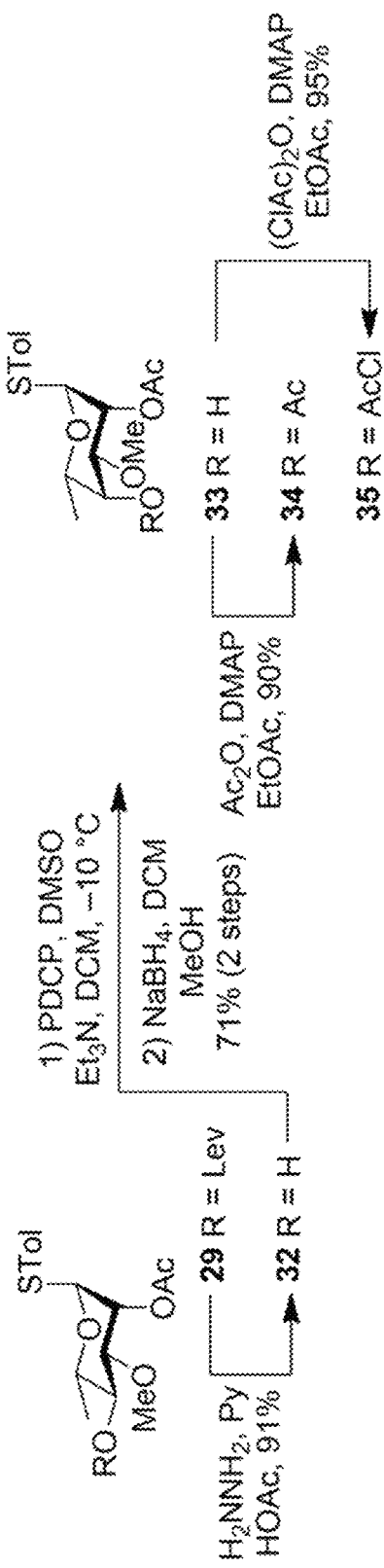

We hypothesized that the simultaneous presence of two hydroxyl groups could lead to macromolecular interactions preventing the oxidation step to occur. Therefore, we envisioned that the introduction of a terminal 6-deoxy-talose residue would restrict these interactions and consequently enable the epimerization of the inner rhamnose unit. As depicted in FIG. 8, derivatives 34 and 35 were prepared from building block 29. Delevulinoylation of the latter was performed using standard conditions. Pfitzner-Moffatt oxidation followed by reduction of the crude ketone with NaBH$_4$ furnished thiotaloside 33 in 65% yield over three steps. Acetylation of the remaining hydroxyl group using Ac$_2$O and catalytic DMAP in refluxing EtOAc led to building block 34, which mimicked Bp LPS OAg terminal residue. As for Bm-like LPS OAg terminal residue, a chloroacetyl group was used as a temporary protecting group, which could be further transformed into an acetyl group following its orthogonal deprotection. This reaction was performed using chloroacetic anhydride and catalytic DMAP in refluxing EtOAc providing building block 35 in an almost quantitative yield.

Figure 9:
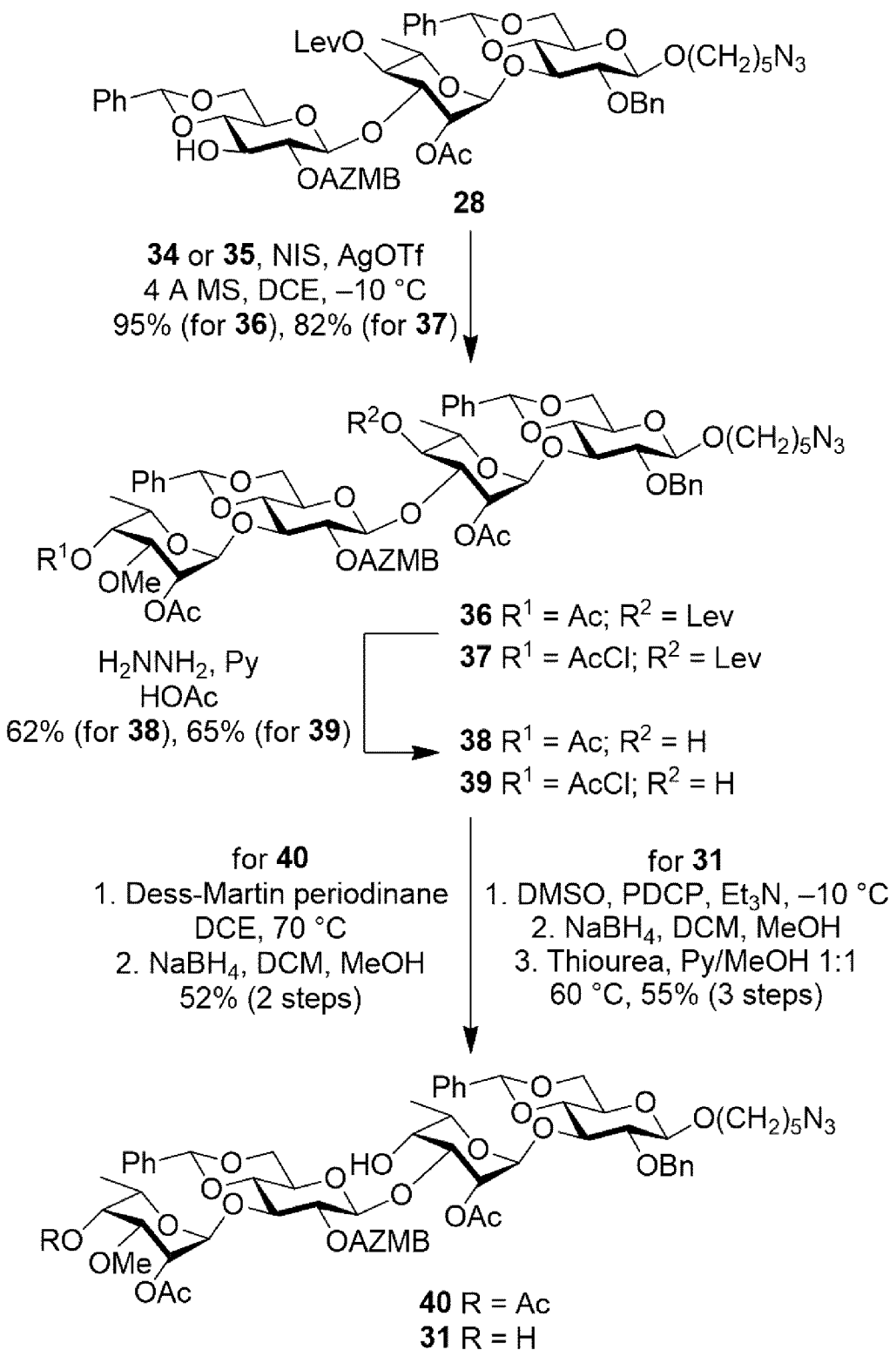

To prepare Bp and Bm LPS OAg-like tetrasaccharides, trisaccharide acceptor 28 was coupled with thiotaloside 34 and 35, respectively, under previously mentioned conditions, affording tetrasaccharides 36 and 37 exclusively as the α-anomers (FIG. 9). Upon delevulinoylation of these latter, either Dess-Martin periodinane reagent or Pfitzner-Moffatt conditions were successfully used for their oxidations. In both cases, the resulting ketone was filtered over silica gel and then reduced with complete stereoselectivity into its talose configuration under the action of NaBH$_4$. This two-step sequence enabled the isolation of tetrasaccharide 40 in a moderate 52% yield due to its partial degradation during the oxidation step. Derivative 31 was ultimately reached in a 55% yield over three steps following chloroacetyl cleavage using thiourea in a mixture of pyridine and methanol.

Global Deprotection of Tetrasaccharides

Figure 10:
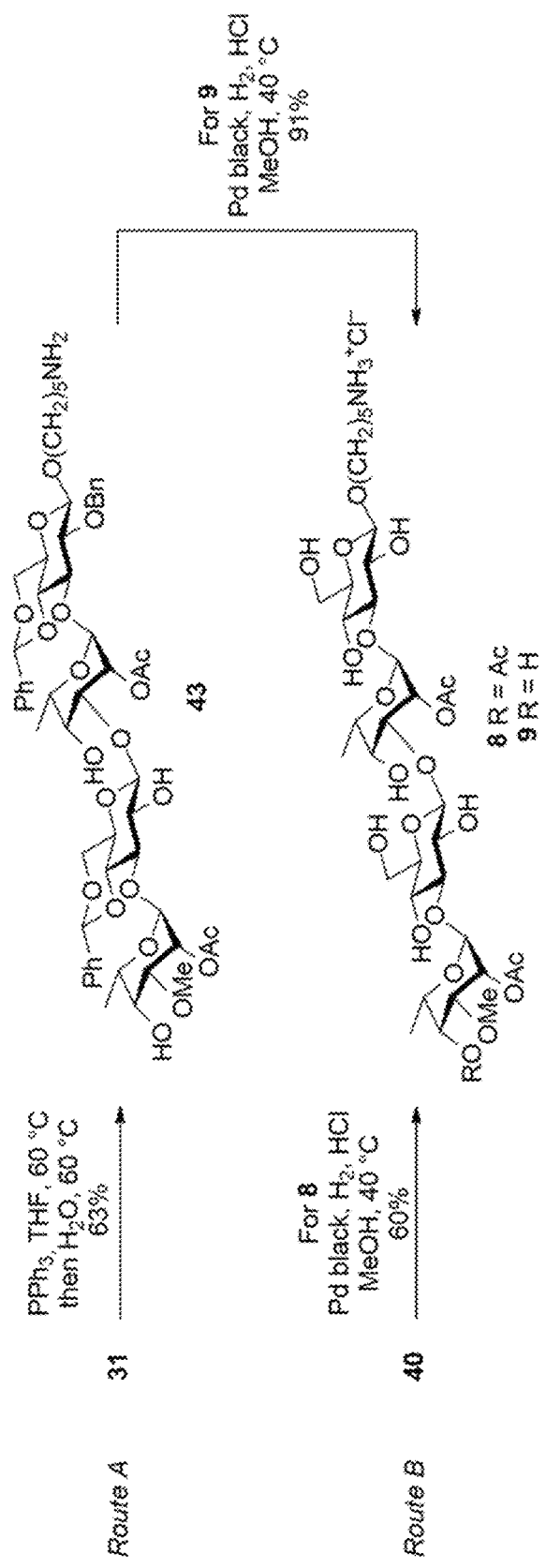
Figure 11:
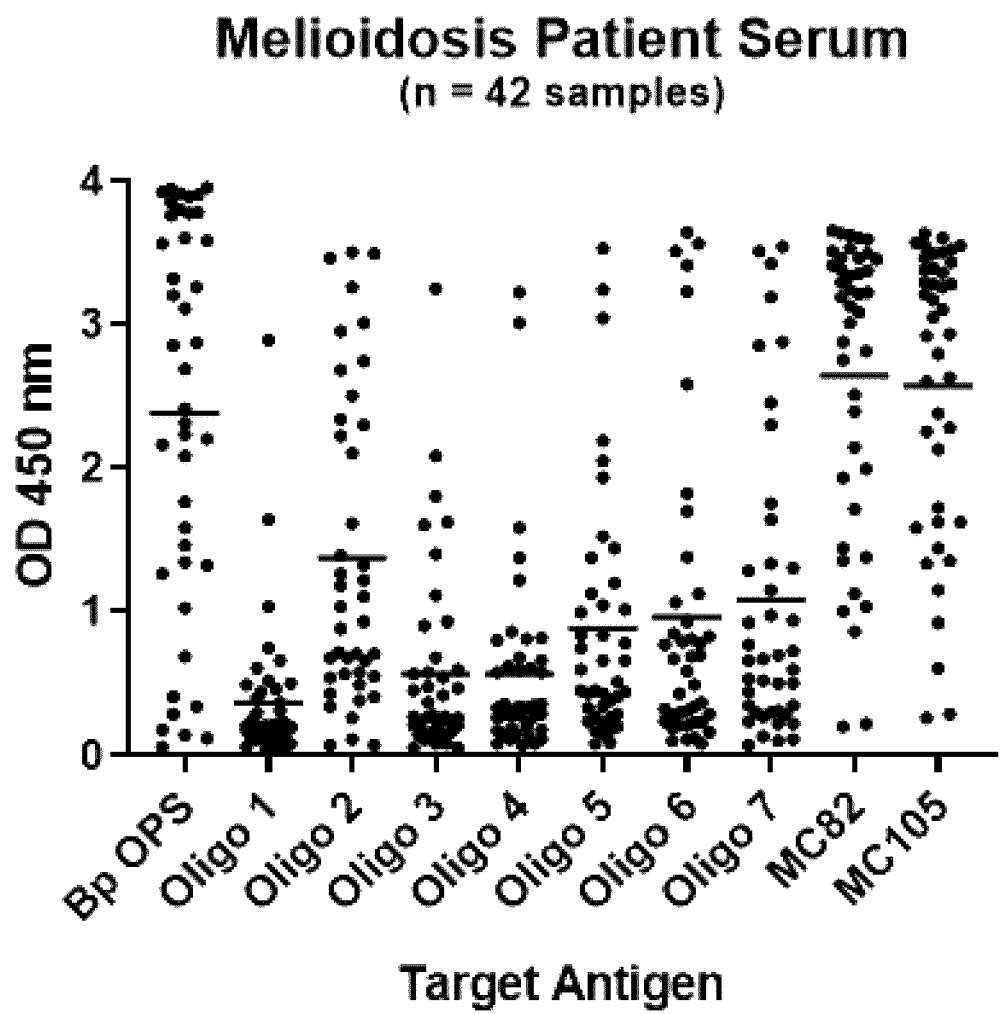

Two alternative pathways were studied for the global deprotection of tetrasaccharides 40 and 31 in order to reach target compounds 8 and 9, respectively. The first pathway (route A) consisted in the selective reduction of both azides followed by hydrogenolysis of the remaining benzyl and benzylidene groups, whereas the second route (route B) only involved the hydrogenolysis step. We therefore investigated a series of conditions for the selective reduction of both azides via the Staudinger reaction, which would result in the assisted cleavage of the AZMB group. We first planned to use trisaccharide 27 as a model compound, as we hypothesized that if difficulties had to arise during the AZMB deprotection, it would be due to the electrophilic acetyl group at the inner talose residue. Intramolecular rearrangement of iminophosphorane intermediates during the Staudinger reduction can indeed occur in compounds containing a neighbouring ester.[43] Preliminary reduction tests were first conducted with trisaccharide 27, but we noticed that the reduction of the azidolinker reduction required harsher conditions than the AZMB group. Our hypothesis was that anchimeric assistance from the carbonyl moiety of the latter prior the hydrolysis step favoured its reduction. Our attention therefore shifted to disaccharide 26 and conditions were optimized for the sole reduction of the azidolinker (Table 2). Triphenylphosphine was first used in a mixture of THF/H$_2$O in the presence of SiO$_2$ (entry 1).[31] After 20 h, the starting material was totally consumed but, as shown by TLC, the intermediates were not fully hydrolysed. Following work-up with aqueous NaHCO$_3$ and purification, target amine 41 was isolated in low yield (21%). We then attempted to conduct the reaction through a two-step procedure, i.e., 1) formation of the iminophosphorane and 2) its hydrolysis, while heating the reaction mixture to 60° C., but a lower yield of amine 41 was obtained (entry 2). Switching the solvent for DMF and avoiding the work-up procedure allowed to improve the yield to 38% (entry 3). Satisfyingly, using the same reaction conditions than in entry 3 while avoiding the work-up provided amine 41 in excellent yield (88%, entry 4). Tris(4-methoxyphenyl)phosphine [P(PMP)$_3$] was also tested without yield improvement (entry 5). The optimized reduction conditions were then applied to trisaccharide 27 bearing both the azidolinker and the AZMB group, yielding alcohol 42 in good yield (76%, entry 6). These conditions finally successfully furnished tetrasaccharide 43 from diol 31 (63%, entry 7), which was then deprotected into target compound 9 through a Pd-catalyzed hydrogenolysis, as shown in FIG. 10.

Alternatively, reduction of the azides into the corresponding amines and cleavage of the permanent protecting groups were carried out via a one-step hydrogenolysis procedure, enabling the conversion of compound 40 into Bp-like tetrasaccharide 8. Noteworthy, the presence of the azidolinker required the addition of HCl (1.0 equiv) in the reaction mixture in order to protonate the amine formed upon its reduction, as primary amines are known to poison transition metal catalysts.[44] Partial protonation of the 2-(aminomethyl) benzoyl group therefore also occurred prior to completion of the intramolecular cyclization, preventing the complete release of the corresponding hydroxyl group. The partial cleavage of the AZMB group not only diminished the isolated yield, but also complicated the purification of the target compound. First, exclusion size chromatography using LH-20 resin was employed to purify the tetrasaccharides from the isoindolinone, which was released following the AZMB cleavage. Then, reverse phase chromatography was required to isolate tetrasaccharide 8 from the derivative still bearing the protonated 2-(aminomethyl)benzoyl group. Despite this, direct hydrogenolysis of compound 40 still enabled the isolation of pure tetrasaccharide 8 in a moderate 60% yield, as shown in FIG. 10.

Reversed-phase flash column chromatography was performed on $C_{18}$ silica gel (fully capped, 25-40 μm). Size exclusion chromatography was performed on GE Healthcare Sephadex LH-20 resin (70 μm). NMR spectra were recorded at 297 K in the indicated solvent (CDCl$_3$, py-d5 or D$_2$O) with a 600 MHz instrument, employing standard softwares given by the manufacturer. $^1$H and 13C NMR spectra were referenced to tetramethylsilane (TMS, $\delta_H$=$\delta_C$=0.00 ppm) as

TABLE 2

Optimization of the Staudinger reaction for azide reduction

| Entry | Reactant | Conditions | Work-up | Product | Yield (%)[a] |
|---|---|---|---|---|---|
| 1 | 26 | PPh$_3$, SiO$_2$, THF/H$_2$O, rt, 20 h | NaHCO$_3$, H$_2$O, DCM | 41 | 21 |
| 2 | 26 | PPh$_3$, THF, 60° C., 2 h, then H$_2$O, 60° C., 4 h | NaHCO$_3$, H$_2$O, DCM | 41 | 13 |
| 3 | 26 | PPh$_3$, DMF, 0° C. to rt, 2 h, then H$_2$O, rt, 26 h | Toluene co-evaporation | 41 | 38 |
| 4 | 26 | PPh$_3$, THF, 60° C., 2 h, then H$_2$O, 60° C., 4 h | Evaporation | 41 | 88 |
| 5 | 26 | P(PMP)$_3$, THF, 60° C., 2 h, then H$_2$O, 60° C., 4 h | Evaporation | 41 | 63 |
| 6 | 27 | PPh$_3$, THF, 60° C., 2 h, then H$_2$O, 60° C., 4 h | Evaporation | 42 | 76 |
| 7 | 31 | PPh$_3$, THF, 60° C., 2 h, then H$_2$O, 60° C., 4 h | Evaporation | 43 | 63 |

[a]Isolated yield.

Experimental Section

General Methods.

All starting materials and reagents were purchased from commercial sources and used as received without further purification. Air and water sensitive reactions were performed in oven-dried glassware under Ar atmosphere. Moisture sensitive reagents were introduced via a dry syringe. Anhydrous solvents were either prepared from commercial solvents and dried over heat-gun activated 4 Å molecular sieves or supplied over molecular sieves and used as received. Powdered 4 Å molecular sieves were activated before use by heating with a heat fun for ~5 min under high vacuum. Reactions were monitored by thin-layer chromatography (TLC) with silica gel 60 F$_{254}$ 0.25 mm pre-coated aluminium foil plates. Compounds were visualized by using UV$_{254}$ and/or orcinol (1 mg·mL$^{-1}$) in 10% aq H$_2$SO$_4$ solution with heating. Normal-phase flash column chromatography was performed on silica gel 60 Å (15-40 μm).

internal reference for spectra in CDCl$_3$ and py-d$_5$, or to internal acetone ($\delta_H$=2.218 ppm; $\delta_C$=30.9 ppm) for spectra in D$_2$O. Assignments were based on $^1$H, 13C, COSY, HSQC and undecoupled HSQC experiments. Interchangeable assignments are marked with an asterisk. High-resolution mass spectra (HRMS) were recorded on an ESI-Q-TOF mass spectrometer. Optical rotations [α]$^{20}$D were measured on an Anton Paar polarimeter.

para-Methylphenyl 2-O-ortho-(azidomethyl)benzoyl-4,6-O-benzylidene-3-O-para-methoxybenzyl-1-thio-β-D-glucopyranoside (18)

Bu$_2$SnO (1902 mg, 7.640 mmol, 1.1 equiv) was added to a solution of diol 17 (2411 mg, 6.946 mmol, 1.0 equiv) in toluene (83 mL). The mixture was refluxed with a Dean-Stark trap for 3 h, after which the solvents were evaporated under reduced pressure. The residue was solubilized in anhydrous DMF (83 mL) and CsF (1076 mg, 7.085 mmol, 1.02 equiv), TBAI (2617 mg, 7.085 mmol, 1.02 equiv), and PMBCl (1.13 mL, 8.34 mmol, 1.2 equiv) were successively added. The mixture was stirred at 90° C. for 16 h and the resulting suspension was cooled at 0° C. and filtered over Celite. The solution was co-evaporated with toluene and the residue was purified by silica gel flash chromatography (Hex/EtOAc 9:1 to 3:7) to give para-methylphenyl 4,6-O-benzylidene-3-O-para-methoxybenzyl-1-thio-δ-D-glucopyranoside (1738 mg, 51%, 82% brsm) as a white amorphous solid. DMAP (144 mg, 1.18 mmol, 1.0 equiv), DCC (486 mg, 2.36 mmol, 2.0 equiv), and AZMBOH (313 mg, 1.77 mmol, 1.5 equiv) were successively added to a solution of the previously prepared alcohol (582 mg, 1.18 mmol, 1.0 equiv) in anhydrous DCM (12 mL). The mixture was refluxed for 4 h under Ar and the resulting suspension was filtered over Celite. The solvent was concentrated under reduced pressure and the residue was purified by silica gel flash chromatography (Hex/EtOAc 9:1 to 2:8), furnishing glucoside 18 (751 mg, 98%) as a white amorphous solid: $R_f$ 0.6 (Hex/EtOAc 7:3); $[\alpha]_D^{20}$+36 (c 0.7, CHCl$_3$); $^1$H NMR (600 MHz, CDCl$_3$) δ (ppm) 7.87-7.86 (m, 1H, CH$_{AZMB}$), 7.61-7.59 (m, 1H, CH$_{Ar}$), 7.56-7.55 (m, 1H, CH$_{Ar}$), 7.50-7.49 (m, 2H, 2×CH$_{Ar}$), 7.41-7.37 (m, 4H, 4×CH$_{Ar}$), 7.35-7.33 (m, 2H, 2×CH$_{STol}$), 7.10-7.09 (m, 2H, 2×CH$_{STol}$), 7.05-7.03 (m, 2H, 2×CH$_{PMB}$), 6.60-6.59 (m, 2H, 2×CH$_{PMB}$), 5.60 (s, 1H, H-7), 5.20 (dd, J=9.9 Hz, J=9.0 Hz, 1H, H-2), 4.81-4.72 (m, 4H, H-1, CH$_{2AZMB}$, CHH$_{PMB}$), 4.57 (d, 1H, J=11.6 Hz, CHH$_{PMB}$), 4.41 (dd, $J_{6a}$-$J_{6b}$=10.5 Hz, $J_{6a-5}$=5.0 Hz, 1H, H-6a), 3.87-3.82 (m, 2H, H-3 and H-6b), 3.77 (t, J=9.3 Hz, 1H, H-4), 3.69 (s, 3H, CH$_{3PMB}$), 3.55 (td, $J_{5-4}$=9.8 Hz, $J_{5-6a}$=5.0 Hz, 1H, H-5), 2.33 (s, 3H, CH$_{3STol}$); $^{13}$C NMR (150 MHz, CDCl$_3$) δ (ppm) 165.0 (COOR$_{AZMB}$), 159.3 (C$_{Ar}$), 138.8 (C$_{Ar}$), 137.8 (C$_{Ar}$), 137.3 (C$_{Ar}$), 133.8 (20, 2×CH$_{STol}$), 133.0 (CH$_{Ar}$), 131.2 (CH$_{AZMB}$), 130.0 (C$_{Ar}$), 129.9, 129.8 (4C, 2×CH$_{STol}$, 2×CH$_{PMB}$), 129.5 (CH$_{Ar}$), 129.2 (C$_{Ar}$), 128.6 (CH$_{Ar}$), 128.4 (3C, 3×CH$_{Ar}$), 128.0 (C$_{Ar}$), 126.1 (2C, 2×CH$_{Ar}$), 113.7 (2C, 2×CH$_{PMB}$), 101.4 (C-7), 87.1 (C-1), 81.7 (C-4), 79.2 (C-3), 74.1 (CH$_{2PMB}$), 72.1 (C-2), 70.7 (C-5), 68.7 (0-6), 55.2 (CH$_{3PMB}$), 53.0 (CH$_{2AZMB}$), 21.3 (CH$_{3STol}$); HRMS (ESI-TOF) m/z [M+Na]$^+$ calcd for C$_{36}$H$_{35}$N$_3$NaO$_7$S 676.2088; found 676.2067.

para-Methyl phenyl 2-O-ortho-(azidomethyl)benzoyl-4,6-O-benzylidene-1-thio-β-D-glucopyranoside (15)

DDQ (378 mg, 1.66 mmol, 2.0 equiv) was added to a solution of glucoside 18 (544 mg, 0.832 mmol, 1.0 equiv) in DCM (18 mL) and H$_2$O (1.7 mL) and the mixture was stirred at rt for 2 h. Saturated NaHCO$_3$(aq) (20 mL) was added to quench the solution, which was then diluted in EtOAc (30 mL) and transferred in a separatory funnel. The organic layer was washed with saturated NaHCO$_3$(aq) (30 mL) and brine (30 mL), dried over anhydrous MgSO$_4$, and concentrated under reduced pressure. The residue was purified by silica gel flash chromatography (Hex/EtOAc 90:10 to 85:15) to give alcohol 15 (343 mg, 77%) as a white amorphous solid: $R_f$ 0.5 (Hex/EtOAc 7:3); $[\alpha]_D^{20}$−26 (c 0.7, CHCl$_3$); $^1$H NMR (600 MHz, CDCl$_3$) δ (ppm) 8.05-8.04 (m, 1H, CH$_{AZMB}$), 7.60-7.58 (m, 1H, CH$_{Ar}$), 7.52-7.51 (m, 1H, CH$_{Ar}$), 7.49-7.47 (m, 2H, 2×CH$_{Ar}$), 7.46-7.43 (m, 1H, CH$_{Ar}$), 7.37-7.36 (m, 5H, 2×CH$_{STol}$, 3×CH$_{Ar}$), 7.12 (m, 2H, 2×CH$_{STol}$), 5.56 (s, 1H, H-7), 5.15 (dd, $J_{2-1}$=9.9 Hz, $J_{2-3}$=8.9 Hz, 1H, H-2), 4.85-4.76 (m, 3H, H-1, CH$_{2AZMB}$), 4.41 (dd, $J_{6a-6b}$=10.5 Hz, $J_{6a-5}$=4.9 Hz, 1H, H-6a), 4.05 (t, J=9.0 Hz, 1H, H-3), 3.82 (t, $J_{6b-6a}$=10.2 Hz, 1H, H-6b), 3.61 (t, J=9.3 Hz, 1H, H-4), 3.55 (td, $J_{5-4}$=9.7 Hz, $J_{5-6a}$=4.9 Hz, 1H, H-5), 2.35 (s, 3H, CH3s-rol); $^{13}$C NMR (150 MHz, CDCl$_3$) δ (ppm) 166.0 (COOR$_{AZMB}$), 138.9 (C$_{Ar}$), 137.3 (C$_{Ar}$), 136.9 (C$_{Ar}$), 133.7 (20, 2×CH$_{STol}$), 133.1 (CH$_{Ar}$), 131.3 (CH$_{AZMB}$), 130.0-126.4 (110, 2×C$_{Ar}$, 9×CH$_{Ar}$), 102.1 (C-7), 86.7 (C-1), 80.6 (C-4), 73.7 (C-3), 73.4 (C-2), 70.6 (C-5), 68.6 (C-6), 53.3 (CH$_{2AZMB}$), 21.3 (CH$_{3STol}$); HRMS (ESI-TOF) m/z [M+Na]$^+$ calcd for C$_{28}$H$_{27}$N$_3$NaO$_6$S 556.15128; found 556.15109; m/z [M+NH$_4$]$^+$ calcd for C$_{28}$H$_{31}$N$_4$O$_6$S 551.19588; found 551.19581.

Allyl 2-O-acetyl-3-tert-butyldimethylsilyl-4-O-levulinoyl-α-L-rhamnopyranoside (20)

TBSCl (1989 mg, 13.23 mmol, 4.0 equiv), imidazole (674 mg, 9.92 mmol, 3.0 equiv), and DMAP (81 mg, 0.7 mmol, 0.2 equiv) were successively added to a solution of diol 19$^{26}$ (1000 mg, 3.307 mmol, 1.0 equiv) in anhydrous THF (80 mL). The mixture was refluxed for 16 h under Ar. The suspension was filtered over Celite, rinsed, and concentrated under reduced pressure. The residue was purified by silica gel flash chromatography (Hex/EtOAc) to give allyl 3-tert-butyldimethylsilyl-4-O-levulinoyl-α-L-rhamnopyranoside (1375 mg, quantitative) as a yellow oil: $R_f$ 0.4 (Hex/EtOAc 7:3); $[\alpha]_D^{20}$−40 (c 1.1, CHCl$_3$); $^1$H NMR (700 MHz, CDCl$_3$) δ (ppm) 5.91 (dddd, $J_{2-3A}$=17.2 Hz, $J_{2-3B}$=10.4 Hz, $J_{2-1A}$=6.1 Hz, $J_{2-1B}$=5.1 Hz, 1H, H-2$_{Allyl}$), 5.29 (ddd, J=17.2 Hz, 5.4 Hz, 1.6 Hz, 1H, H-3a$_{Allyl}$), 5.21 (ddd, J=10.4 Hz, 4.8 Hz, 1.3 Hz, 1H, H-3b$_{Allyl}$), 4.97 (t, J=9.6 Hz, 1H, H-4), 4.87 (d, J=1.4 Hz, 1H, H-1), 4.17 (ddt, J=13.1 Hz, 5.1 Hz, 1.5 Hz, 1H, H-1a$_{Allyl}$), 4.04-3.97 (m, 2H, H-3, H-1b$_{Allyl}$), 3.83 (dd, $J_{2-3}$=3.6 Hz, $J_{2-1}$=1.5 Hz, 1H, H-2), 3.76 (dd, $J_{5-4}$=9.8 Hz, J5-6=6.3 Hz, 1H, H-5), 2.89-2.81 (m, 1H, CHHLev), 2.74-2.66 (m, 1H, CHH$_{Lev}$), 2.64 (m, 1H, CHH$_{Lev}$), 2.54-2.47 (m, 1H, CHH$_{Lev}$), 2.20 (s, 3H, CH$_{3Lev}$), 1.19 (d, J=6.3 Hz, 3H, H-6), 0.88 (s, 9H, C(CH$_3$)$_{3TBS}$), 0.11 (s, 3H, CH$_{3TBS}$), 0.08 (s, 3H, CH$_{3TBS}$); $^{13}$C NMR (176 MHz, CDCl3) δ (ppm) 206.5 (CO$_{Lev}$), 172.1 (COOR$_{Lev}$), 133.9 (C-2$_{Allyl}$), 117.6 (C-3$_{Allyl}$), 98.0 (C-1), 74.3 (C-4), 71.8 (C-2), 70.6 (C-3), 68.2 (C-1$_{Allyl}$), 66.3 (C-5), 38.0 (CH$_{2Lev}$), 30.0 (CH$_{3Lev}$), 28.2 (CH$_{2Lev}$), 25.7 (3C, C(CH$_3$)$_{3TBS}$), 18.0 (C(CH$_3$)$_{3TBS}$), 17.5 (C-6), 4.5 (CH$_{3TBS}$), 4.6 (CH$_{3TBS}$); HRMS (ESI-TOF) m/z [M+Na]$^+$ calcd for C$_{20}$H$_{36}$NaO$_7$Si 439.21225; found 439.21102. The latter alcohol (1000 mg, 2.400 mmol, 1.0 equiv) was dissolved in anhydrous pyridine (40 mL), and Ac$_2$O (40 mL) and DMAP (59 mg, 0.48 mmol, 0.2 equiv) were added. The mixture was stirred at rt for 16 h under Ar. The solution was diluted in toluene and concentrated under reduced pressure. The residue was purified by silica gel flash chromatography (Hex/EtOAc) to give glycoside 20 (1013 mg, 92%) as a colorless oil: $R_f$ 0.6 (Hex/EtOAc 7:3); $[\alpha]_D^{20}$−23 (c 1.0, CHCl$_3$); $^1$H NMR (600 MHz, CDCl3) δ (ppm) 5.93-5.87 (m, 1H, H-2$_{Allyl}$), 5.29 (ddd, J=17.1 Hz, 3.6 Hz, 1.5 Hz, 1H, H-3a$_{Allyl}$), 5.22 (ddd, J=10.4 Hz, 3.2 Hz, 1.3 Hz, 1H, H-3b$_{Allyl}$), 5.10 (dd, $J_{2-3}$=3.6 Hz, $J_{2-1}$=1.8 Hz, 1H, H-2), 4.98 (t, J=9.7 Hz, 1H, H-4), 4.73 (d, J=1.6 Hz, 1H, H-1), 4.16 (ddt, J=13.0 Hz, 5.2 Hz, 1.4 Hz, 1H, H-1a$_{Allyl}$), 4.08 (dd, $J_{3-4}$=9.5 Hz, $J_{3-2}$=3.6 Hz, 1H, H-3), 3.99 (ddt, J=13.0 Hz, 6.1 Hz, 1.3 Hz, 1H, H-1b$_{Allyl}$), 3.78 (dq, $J_{5-4}$=9.9 Hz, $J_{5-6}$=6.4 Hz, 1H, H-5), 2.88-2.82 (m, 1H, CHH$_{Lev}$), 2.70-2.62 (m, 2H, CHH$_{Lev}$, CHH$_{Lev}$), 2.52-2.47 (m, 1H, CHH$_{Lev}$), 2.20 (s, 3H, CH$_{3Levl}$), 2.11 (s, 3H, CH$_{3AC}$), 1.20 (d, J=6.3 Hz, 3H, H-6), 0.82 (s, 9H, C(CH$_3$)$_{3TBS}$), 0.07 (s, 3H, CH$_{3TBS}$), 0.05 (s, 3H, CH$_{3TBS}$); $^{13}$C NMR (150 MHz, CDCl$_3$) δ (ppm) 206.5 (CO$_{Lev}$), 172.0 (COOR$_{Lev}$), 170.5 (COOR$_{Ac}$), 133.7 (C-2$_{Allyl}$), 117.8 (C-3$_{Allyl}$), 96.9 (C-1), 74.5 (C-4), 72.3 (C-2), 68.4, 68.3 (2C, C-1$_{Allyl}$, C-3), 66.7

(C-5), 38.0 (CH$_{2Lev}$), 30.0 (CH$_{3Lev}$) 28.2 (CH$_{2Lev}$), 25.6 (3C, C(CH$_3$)$_{3TBS}$), 21.1 (CH$_{3Ac}$), 17.9, 17.6 (2C, C-6, C(CH$_3$)$_{3TBS}$), 4.7 (CH$_{3TBS}$), 4.9 (CH$_{3TBS}$); HRMS (ESI-TOF) m/z [M+NH$_4$]$^+$ calcd for C$_{22}$H$_{42}$NO$_8$Si 476.26742; found 476.26647; m/z [M+Na]$^+$ calcd for C$_{22}$H$_{38}$NaO$_8$Si 481.22282; found 481.22179.

2-O-Acetyl-3-tert-butyldimethylsilyl-4-O-levulinoyl-α-L-rhamnopyranoside (21)

1,5-Cyclooctadiene-bis(methyldiphenylphosphine)-iridium(I) hexafluorophosphate (132 mg, 0.156 mmol, 0.05 equiv) was dissolved in anhydrous THF (15 mL) and the red solution was degassed under Ar. Hydrogen was bubbled through the solution for 5 min and the resulting yellow solution was once again degassed under argon. A solution of rhamnoside 20 (1435 mg, 3.129 mmol, 1.0 equiv) in anhydrous THF (15 mL) was added and the reaction mixture was stirred for 2 h at rt under Ar. Then, a solution of iodine (1588 mg, 6.258 mmol, 2.0 equiv) in THF/H$_2$O (4:1, 18 mL) was added to the mixture, which was stirred for 1 h at rt. The excess of iodine was quenched by adding a freshly prepared 10% Na$_2$S$_2$O$_3$(aq) solution and stirred until the color turned bright yellow. THF was evaporated under reduced pressure and the resulting aqueous phase was extracted using EtOAc (3×25 mL). The combined organic layers were washed with saturated NaHCO$_3$(aq) (50 mL) and brine (50 mL). The organic phase was dried over anhydrous MgSO$_4$ and concentrated under reduced pressure. The residue was purified by silica gel flash chromatography (Hex/EtOAc) to give hemiacetal 21 (1100 mg, 84%, ratio α/β~85:15) as a brown oil: R$_f$ 0.6 (Tol/EtOAc 1:1); [α]$_D^{20}$ −14 (c 1.1, CHCl$_3$); $^1$H NMR (600 MHz, CDCl$_3$) δ (ppm) 5.11 (2×s, 2H, H-1, H-2), 4.98 (t, J=9.6 Hz, 1H, H-4), 4.14 (dd, J$_{3-4}$=9.4 Hz, J$_{3-2}$=3.0 Hz, 1H, H-3), 4.01 (dq, J$_{5-4}$=9.7 Hz, J$_{5-6}$=6.3 Hz, 1H, H-5), 3.14 (s, 1H, OH), 2.88-2.82 (m, 1H, CHH$_{Lev}$), 2.69-2.64 (m, 2H, CHH$_{Le3v}$, CHH$_{Lev}$), 2.54-2.49 (m, 1H, CHH$_{Lev}$), 2.20 (s, 3H, CH$_{3Lev}$), 2.12 (s, 3H, CH$_{3Ac}$), 1.20 (d, J=6.3 Hz, 3H, H-6), 0.83 (s, 9H, (C(CH$_3$)$_{3TBS}$), 0.08 (s, 3H, CH$_{3TBS}$), 0.06 (s, 3H, CH$_{3TBS}$); $^{13}$C NMR (150 MHz, CDCl$_3$) δ (ppm) 206.7 (CO$_{Lev}$), 172.1 (COOR$_{Lev}$), 170.7 (COOR$_{Ac}$), 92.4 (C-1), 74.5 (C-4), 72.6 (C-2), 67.9 (C-3), 66.9 (C-5), 38.0 (CH$_{2Lev}$), 30.0 (CH$_{3Lev}$), 28.2 (CH$_{2Lev}$), 25.6 (3C, C(CH$_3$)$_{3TBS}$), 21.1 (CH$_{3Ac}$), 17.9, 17.7 (2C, C-6, C(CH$_3$)$_{3TBS}$), −4.7 (CH$_{3TBS}$), −4.9 (CH$_{3TBS}$); HRMS (ESI-TOF) m/z [M+NH$_4$]$^+$ calcd for C$_{19}$H$_{38}$NO$_8$Si 436.23612; found 436.2351; m/z [M+Na]$^+$ calcd for C$_{15}$H$_{34}$NaO$_8$Si 441.19152; found 441.19063.

2-O-Acetyl-3-tert-butyldimethylsilyl-4-O-levulinoyl-α-L-rhamnopyranosyl 2,2,2-trichloroacetimidate (13)

To a cool solution of hemiacetal 21 (383 mg, 0.915 mmol, 1.0 equiv) in acetone (2.3 mL) and DCM (11.5 mL) were added Cs$_2$CO$_3$ (59 mg, 0.18 mmol, 0.2 equiv) and CCl$_3$CN (0.46 mL, 4.6 mmol, 5.0 equiv). The mixture was stirred for 1 h at rt, then the suspension was filtered over Celite and rinsed with DCM. The solvents were concentrated under reduced pressure. The residue was purified by silica gel flash chromatography (Tol/EtOAc+1% Et$_3$N 95:5 to 9:1) to give trichloroacetimidate 13 (504 mg, 98%, α/β~9:1) as a yellow oil: R$_f$ 0.3 (Tol/EtOAc 9:1+1% Et$_3$N); R$_f$ 0.5 (Tol/AcOEt 8:2+1% Et$_3$N); $^1$H NMR (600 MHz, py-d$_5$) δ (ppm) 6.71 (s, 1H, H-1), 5.75 (s, 1H, H-2), 5.58 (t, J=9.7 Hz, 1H, H-4), 4.60 (dd, J$_{3-4}$=9.6 Hz, J$_{3-2}$=3.5 Hz, 1H, H-3), 4.40 (dq, J$_{5-4}$=12.2 Hz, J$_{5-6}$=6.0 Hz, 1H, H-5), 2.96-2.73 (m, 4H, 2×CH$_{2Lev}$), 2.08 (s, 3H, CH$_{3Lev}$), 2.03 (s, 3H, CH$_{3Ac}$), 1.48 (d, J=6.2 Hz, 3H, H-6), 0.96 (s, 9H, C(CH$_3$)$_{3TBS}$), 0.26 (s, 3H, CH$_{3TBS}$), 0.24 (s, 3H, CH$_{3TBS}$); $^{13}$C NMR (150 MHz, py-d$_5$) δ (ppm) 206.7 (CO$_{Lev}$), 172.9 (COOR$_{Lev}$), 170.4 (COOR$_{Ac}$), 159.3 (C$_{imine}$), 95.8 (C-1), 91.8 (CCl$_3$), 74.3 (C-4), 71.5 (C-2), 70.7 (C-5), 69.5 (C-3), 38.4 (CH$_2$Lev), 30.0 (CH$_{3Lev}$), 29.1 (CH$_{2Lev}$), 26.2 (3C, C(CH$_3$)$_{3TBS}$), 21.0 (CH$_3$Ac), 18.6, 18.4 (C-6, C(CH$_3$)$_{3TBS}$), −4.3 (CH$_{3TBS}$), −4.4 (CH$_{3TBS}$); HRMS (ESI-TOF) m/z [M+Na]$^+$ calcd for C$_{21}$H$_{34}$NaO$_8$Si 584.10115; found 584.10006.

(5-Azido-1-pentyl) 2-O-acetyl-3-tert-butyldimethylsilyl-4-O-levulinoyl-α-L-rhamnopyranosyl-(1→3)-2-O-benzyl-4,6-O-benzylidene-β-D-glucopyranoside (22)

To solution of trichloroacetimidate 13 (449 mg, 0.798 mmol, 1.5 equiv) in anhydrous Et$_2$O (7 mL) cooled at −10° C. were successively added glucoside 16 (250 mg, 0.532 mmol, 1.0 equiv) and TMSOTf (1.9 μL, 11 μmol, 0.02 equiv). The mixture was stirred under Ar at −10° C. for 15 min after which the solution was quenched with Et$_3$N (0.07 mL, 0.5 mmol, 1.0 equiv). The solvents were concentrated under reduced pressure and co-evaporated with toluene. The residue was purified by silica gel flash chromatography (Tol/EtOAc 95:5 to 80:20) to give disaccharide 22 (421 mg, 91%) as a white amorphous solid: R$_f$ 0.7 (Tol/EtOAc 7:3); [α]$_D^{30}$ −51 (c 0.6, CHCl$_3$); $^1$H NMR (600 MHz, CDCl$_3$) δ (ppm) 7.48-7.46 (m, 2H, 2×CH$_{Ar}$), 7.38-7.34 (m, 3H, 3×CH$_{Ar}$), 7.32-7.30 (m, 4H, 4×CH$_{Ar}$), 7.28-7.27 (m, 1H, CH$_{Ar}$), 5.56 (s, 1H, H-7A), 5.20 (dd, J$_{2-3}$=3.6 Hz, J$_{2-1}$=1.6 Hz, 1H, H-2B), 5.13 (d, J=1.3 Hz, 1H, H-1B), 4.87-4.84 (m, 2H, CHH$_{Bn}$, H-4B), 4.72 (d, J=10.8 Hz, 1H, CHH$_{Bn}$), 4.49 (d, J=7.8 Hz, 1H, H-1A), 4.36 (dd, J$_{6a-6b}$=10.5 Hz, J$_{6a-5}$=5.0 Hz, 1H, H6aA), 4.04 (dq, J$_{5-4}$=12.5 Hz, J$_{5-6}$=6.2 Hz, 1H, H-5B), 3.99 (dd, J$_{3-4}$=9.5 Hz, J$_{3-2}$=3.6 Hz, 1H, H-3B), 3.94-3.89 (m, 2H, H-1alinker, H-3A), 3.78 (t, J=10.3 Hz, 1H, H-6bA), 3.59-3.54 (m, 2H, H-1b$_{linker}$, H-4A), 3.46 (dd, J=8.7 Hz, J=7.9 Hz, 1H, H-2A), 3.42 (dt, J=9.8 Hz, J=5.0 Hz, 1H, H-5A), 3.22 (t, J=6.9 Hz, 2H, H-5$_{linker}$), 2.78-2.73 (m, 1H, CHH$_{Lev}$), 2.64-2.59 (m, 1H, CHH$_{Lev}$), 2.54-2.49 (m, 1H, CHH$_{Lev}$), 2.47-2.42 (m, 1H, CHH$_{Lev}$), 2.18 (s, 3H, CH$_{3Lev}$), 2.04 (s, 3H, CH$_{3Ac}$), 1.69-1.63 (m, 2H, H-2$_{linker}$), 1.62-1.59 (m, 2H, H-4$_{linker}$), 1.50-1.41 (m, 2H, H-3) 0.81 (s, 9H, C(CH$_3$)$_{3TBS}$), 0.78 (d, J=6.3 Hz, 3H, H-6B), 0.08 (s, 3H, CH$_{3TBS}$), 0.04 (s, 3H, CH$_{3TBS}$); $^{13}$C NMR (150 MHz, CDCl$_3$) δ (ppm) 206.3 (CO$_{Lev}$), 171.9 (COOR$_{Lev}$), 170.1 (COOR$_{Ac}$), 138.0 (C$_{Ar}$), 137.3 (C$_{Ar}$), 129.3-126.3 (10C, 10×CH$_{Ar}$), 104.3 (C-1A), 101.8 (C-7A), 98.2 (C-1B), 82.6 (C-2A), 79.3 (C-4A), 76.2 (C-3A), 74.9 (CH2Bn), 74.5 (C-4B), 72.0 (C-2B), 70.2 (C-1$_{linker}$), 69.0 (C-6A), 68.3 (C-3B), 66.43, 66.37 (2C, C-5A, C-5B), 51.4 (C-5$_{linker}$), 37.9 (CH$_{2Lev}$), 30.1 (CH$_{3Lev}$), 29.5 (C-2$_{linker}$), 28.8 (C-4$_{linker}$), 28.2 (CH$_{2Lev}$), 25.6 (3C, C(CH$_3$)$_{3TBS}$), 23.5 (C-3$_{linker}$), 21.0 (CH$_{3Ac}$), 17.9 (C(CH$_3$)$_{3TBS}$), 17.0 (C-6B), 4.6 (CH$_{3TBS}$), 4.9 (CH$_{3TBS}$); HRMS (ESI-TOF) m/z [M+NH$_4$]$^+$ calcd for C$_{44}$H$_{67}$N$_4$O$_{13}$Si 887.44684; found 887.44683; m/z [M+Na]$^+$ calcd for C$_{44}$H$_{63}$NaO$_{13}$Si 892.40224; found 892.4035.

para-Methylphenyl 4-O-levulinoyl-1-thio-α-L-rhamnopyranoside (24)

Levulinic acid (1.0 mL, 9.5 mmol, 1.15 equiv), DCC (1952 mg, 9.462 mmol, 1.15 equiv), and DMAP (101 mg, 0.823 mmol, 0.1 equiv) were added in a solution of alcohol 23$^{38}$ (2554 mg, 8.228 mmol, 1 equiv) in anhydrous DCM (100 mL). The mixture was stirred under Ar at 50° C. for 2 h. The suspension was cooled to 0° C., filtered over Celite, and rinsed with cold DCM. The solvents were concentrated under reduced pressure and co-evaporated with toluene. The residue was purified by silica gel flash chromatography (Tol/EtOAc 8:2) to give para-methylphenyl 4-O-levulinoyl-2,3-O-isopropylidene-1-thio-α-L-rhamnopyranoside (3254 mg, 97%) as a white amorphous solid: $R_f$ 0.5 (Tol/EtOAc 7:3); $[\alpha]_D^{30}$ –158 (c 0.6, CHCl$_3$); $^1$H NMR (600 MHz, CDCl$_3$) δ (ppm) 7.37-7.35 (m, 2H, 2×CH$_{STol}$), 7.14-7.12 (m, 2H, 2×CH$_{STol}$), 5.68 (s, 1H, H-1), 4.92 (dd, J=9.9 Hz, J=7.9 Hz, 1H, H-4), 4.35 (d, J=5.3 Hz, 1H, H-2), 4.24-4.18 (m, 2H, H-3, H-5), 2.90-2.85 (m, 1H, CHH$_{Lev}$), 2.72-2.69 (m, 1H, CHH$_{Lev}$), 2.68-2.66 (m, 1H, CHH$_{Lev}$), 2.61-2.56 (m, 1H, CHH$_{Lev}$), 2.33 (s, 3H, CH$_{3STol}$), 2.19 (s, 3H, CH$_{3Lev}$), 1.55 (s, 3H, CH$_{3iso}$), 1.35 (s, 3H, CH$_{3iso}$) 1.15 (d, J=6.3 Hz, 3H, H-6); $^{13}$C NMR (150 MHz, CDCl$_3$) δ (ppm) 206.5 (CO$_{Lev}$), 172.1 (COOR$_{Lev}$), 138.2 (C$_{STol}$), 132.6 (2C, 2×CH$_{STol}$), 130.0 (2C, 2×CH$_{STol}$), 129.4 (C$_{STol}$), 110.1 (C$_{iso}$), 84.1 (C-1), 76.6 (C-2), 75.6 (C-3), 75.1 (C-4), 65.6 (C-5), 38.0 (CH$_{2Lev}$), 29.9 (CH$_{3Lev}$), 28.1 (CH$_{2Lev}$), 27.8 (CH$_{3iso}$), 26.7 (CH$_{3iso}$), 21.3 (CH$_{3STol}$), 16.9 (C-6); HRMS (ESI-TOF) m/z [M+NH$_4$]$^+$ calcd for C$_{21}$H$_{32}$NO$_6$S 426.1945; found 426.1957; m/z [M+Na]$^+$ calcd for C$_{21}$H$_{28}$NaO$_6$S 431.1499; found 431.1512. The latter thiorhamnoside (3239 mg, 7.930 mmol, 1.0 equiv) was dissolved in 80% AcOH(aq) (99 mL) and the solution was stirred at 60° C. for 2 h. The solvents were concentrated under reduced pressure and co-evaporated with toluene. The residue was purified by silica gel flash chromatography (Hex/EtOAc 1:1 to 2:8) to give diol 24 (2615 mg, 90%) as a white amorphous solid: $R_f$ 0.5 (DCM/MeOH 95:5); $[\alpha]_D^{20}$ –230 (c 0.7, CHCl$_3$); $^1$H NMR (600 MHz, CDCl$_3$) δ (ppm) 7.36-7.34 (m, 2H, 2×CH$_{STol}$), 7.13-7.11 (m, 2H, 2×CH$_{STol}$), 5.46 (d, J=0.6 Hz, 1H, H-1), 4.95 (t, J=9.6 Hz, 1H, H-4), 4.29 (dq, J$_{5-4}$=9.8 Hz, J$_{5-6}$=6.2 Hz, 1H, H-5), 4.22 (br s, 1H, H-2), 3.98-3.91 (m, 1H, H-3), 3.48 (d, J=4.4 Hz, 1H, OH$_{C-3}$), 3.06 (br s, 1H, OH$_{C-2}$), 2.88-2.79 (m, 2H, CH$_{2Lev}$), 2.65-2.55 (m, 2H, CH$_{2Lev}$), 2.33 (s, 3H, CH$_{3STol}$), 2.20 (s, 3H, CH$_{3Lev}$), 1.22 (d, J=6.3 Hz, 3H, H-6); $^{13}$C NMR (150 MHz, CDCl$_3$) δ (ppm) 207.7 (CO$_{Lev}$), 175.6 (COOR$_{Lev}$), 137.9 (C$_{STol}$), 132.1 (2C, 2×CH$_{STol}$), 130.2 (C$_{STol}$), 130.0 (2C, 2×CH$_{STol}$), 87.8 (C-1), 75.8 (C-4), 72.4 (C-2), 70.7 (C-3), 67.0 (C-5), 38.5 (CH$_{2Lev}$), 29.9 (CH$_{3Lev}$), 28.4 (CH$_{2Lev}$), 21.3 (CH$_{3STol}$), 17.4 (C-6); HRMS (ESI-TOF) m/z [M+NH$_4$]$^+$ calcd for C$_{18}$H$_{28}$NO$_6$S 386.1632; found 386.1641; m/z [M+Na]$^+$ calcd for C$_{18}$H$_{24}$NaO$_6$S 391.1186; found 391.1197.

para-Methylphenyl 2-O-acetyl-4-O-levulinoyl-3-O-para-methoxybenzyl-1-thio-α-L-rhamnopyranoside (25)

Bu$_2$SnO (1257 mg, 5.052 mmo, 1.1 equiv) was added to a solution of compound 24 (1692 mg, 4.592 mmol, 1.0 equiv) in toluene (55 mL) and the mixture was refluxed with a Dean-Stark trap for 2 h. The solution was cooled to rt and CsF (732 mg, 4.82 mmol, 1.05 equiv), TBAI (1781 mg, 4.822 mmol, 1.05 equiv), and PMBCl (0.74 mL, 5.5 mmol, 1.2 equiv) were successively added. The mixture was stirred under Ar at 40° C. for 16 h. The suspension was cooled at 0° C., filtered over Celite, and rinsed with DCM. The solvents were concentrated under reduced pressure. The residue was purified by silica gel flash chromatography (Hex/EtOAc 9:1 to 1:1) to give para-methylphenyl 4-O-levulinoyl-3-O-para-methoxybenzyl-1-thio-α-L-rhamnopyranoside (1891 mg, 84%) as a yellow oil: $R_f$ 0.6 (Hex/EtOAc 4:6); $[\alpha]_D^{20}$ –140 (c 1.2, CHCl$_3$); $^1$H NMR (600 MHz, CDCl$_3$) δ (ppm) 7.33-7.32 (m, 2H, 2×CH$_{STol}$), 7.27-7.26 (m, 2H, 2×CH$_{PMB}$), 7.12-7.10 (m, 2H, 2×CH$_{STol}$), 6.91-6.89 (m, 2H, 2×CH$_{PMB}$), 5.46 (d, J=1.2 Hz, 1H, H-1), 5.08 (t, J=9.6 Hz, 1H, H-4), 4.59 (d, J=11.7 Hz, 1H, CHH$_{PMB}$), 4.53 (d, J=11.8 Hz, 1H, CHH$_{PMB}$), 4.22 (dq, J$_{5-4}$=9.9 Hz, J$_{5-6}$=6.2 Hz, 1H, H-5), 4.18 (dd, J$_{2-3}$=3.0 Hz, J$_{2-4}$=1.5 Hz, 1H, H-2), 3.81 (s, 3H, CH$_{3PMB}$), 3.75 (dd, J$_{3-4}$=9.4 Hz, J$_{3-2}$=3.3 Hz, 1H, H-3), 2.77-2.71 (m, 2H, CH$_{2Lev}$), 2.59-2.49 (m, 2H, CH$_{2Lev}$), 2.32 (s, 3H, CH$_{3STol}$), 2.19 (s, 3H, CH$_{3Lev}$), 1.18 (d, J=6.3 Hz, 3H, H-6); $^{13}$C NMR (150 MHz, CDCl$_3$) δ (ppm) 206.5 (CO$_{Lev}$), 172.1 (COOR$_{Lev}$), 159.6 (C$_{Ar}$), 137.8 (C$_{Ar}$), 132.1 (2C, 2×CH$_{STol}$), 130.0, 129.7 (5C, C$_{Ar}$, 2×CH$_{STol}$, 2×CH$_{PMB}$), 129.6 (C$_{Ar}$), 114.1 (2C, 2×CH$_{PMB}$), 87.3 (C-1), 76.7 (C-3), 73.0 (C-4), 71.7 (CH$_{2PMB}$), 69.9 (C-2), 67.6 (C-5), 55.4 (CH$_{3PMB}$), 37.9 (CH$_{2Lev}$), 30.0 (CH$_{3Lev}$), 28.1 (CH$_{2Lev}$), 21.2 (CH$_{3STol}$), 17.4 (C-6); HRMS (ESI-TOF) m/z [M+NH$_4$]$^+$ calcd for C$_{26}$H$_{36}$NO$_7$S 506.2207; found 506.22041; m/z [M+Na]$^+$ calcd for C$_{26}$H$_{32}$NaO$_7$S 511.1761; found 511.17561. The latter alcohol (1891 mg, 3.870 mmol, 1.0 equiv) was dissolved in anhydrous pyridine (19 mL) and Ac$_2$O (19 mL), and DMAP (5 mg, 0.04 mmol, 0.01 equiv) was added. The solution was stirred under Ar at rt for 16 h, then the solvents were concentrated under reduced pressure and co-evaporated with toluene. The residue was purified by silica gel flash chromatography (Hex/EtOAc 9:1 to 7:3) to give compound 25 (1877 mg, 91%) as a white amorphous solid: $R_f$ 0.6 (Hex/EtOAc 1:1); $[\alpha]_D^{20}$ –37 (c 1.1, CHCl$_3$); $^1$H NMR (600 MHz, CDCl$_3$) δ (ppm) 7.33-7.32 (m, 2H, 2×CH$_{STol}$), 7.24-7.23 (m, 2H, 2×CH$_{PMB}$), 7.12-7.11 (m, 2H, 2×CH$_{STol}$), 6.90-6.88 (m, 2H, 2×CH$_{PMB}$), 5.56 (dd, J$_{2-3}$=3.2 Hz, J$_{2-1}$=1.6 Hz, 1H, H-2), 5.34 (d, J=1.4 Hz, 1H, H-1), 5.05 (t, J=9.8 Hz, 1H, H-4), 4.58 (d, J=11.9 Hz, 1H, CHH$_{PMB}$), 4.38 (d, J=11.9 Hz, 1H, CHH$_{PMB}$), 4.24 (dq, J$_{5-4}$=9.9 Hz, J$_{5-6}$=6.2 Hz, 1H, H-5), 3.81 (s, 3H, CH$_{3PMB}$), 3.77 (dd, J$_{3-4}$=9.7 Hz, J$_{3-2}$=3.2 Hz, 1H, H-3), 2.80-2.75 (m, 1H, CHH$_{Lev}$), 2.70-2.65 (m, 1H, CHH$_{Lev}$), 2.60-2.55 (m, 1H, CHH$_{Lev}$), 2.52-2.47 (m, 1H, CHH$_{Lev}$), 2.33 (s, 3H, CH$_{3STol}$), 2.18 (s, 3H, CH$_{3Lev}$), 2.12 (s, 3H, CH$_{3Ac}$), 1.21 (d, J=6.3 Hz, 1H, H-6); $^{13}$C NMR (150 MHz, CDCl3) δ (ppm) 206.5 (CO$_{Lev}$), 172.1 (COOR$_{Lev}$), 170.4 (COOR$_{Ac}$), 159.5 (C$_{Ar}$), 138.2 (C$_{Ar}$), 132.4 (2C, 2×CH$_{STol}$), 130.1, 129.8 (5C, C$_{Ar}$, 2×CH$_{STd}$, 2×CH$_{PMB}$), 129.7 (C$_{Ar}$), 113.9 (2C, 2×CH$_{PMB}$), 86.6 (C-1), 74.2 (C-3), 72.9 (C-4), 71.1 (CH$_{2PMB}$), 70.2 (C-2), 68.0 (C-5), 55.4 (CH$_{3PMB}$), 38.0 (CH$_{2Lev}$), 30.0 (CH$_{3Lev}$), 28.1 (CH$_{2Lev}$), 21.3 (CH$_3$), 21.2 (CH$_3$), 17.5 (C-6); HRMS (ESI-TOF) m/z [M+NH$_4$]$^+$ calcd for C$_{28}$H$_{38}$NO$_8$S 548.23216; found 548.23176; m/z [M+Na]$^+$ calcd for C$_{28}$H$_{34}$NaO$_8$S 553.18666; found 553.1874.

(5-Azido-1-pentyl) 2-O-acetyl-4-O-levulinoyl-3-para-methoxybenzyl-α-L-rhamnopyranosyl-(1→3)-2-O-benzyl-4,6-O-benzylidene-β-D-glucopyranoside (26)

Alcohol 16 (702 mg, 1.50 mmol, 1.0 equiv), donor 25 (952 mg, 1.79 mmol, 1.2 equiv), and NIS (505 mg, 2.24 mmol, 1.5 equiv) were dried together under high vacuum for 1 h. 4 Å activated ground molecular sieves (2808 mg) and anhydrous DCM (30 mL) were successively added and the mixture was stirred under Ar for 1 h. The reaction flask was cooled at –10° C. and protected from light using aluminum foil. AgOTf (38 mg, 0.15 mmol, 0.1 equiv) was added and the mixture was stirred under Ar for 1 h while being gradually warmed to 0° C. Et$_3$N (0.21 mL, 1.5 mmol, 1.0 equiv) was added, the yellow suspension was filtered over Celite, and the solvents were evaporated under reduced pressure. The residue was purified by silica gel flash chromatography (Hex/EtOAc 8:2 to 6:4) to give disaccharide 26 (1177 mg, 90%) as a white amorphous solid: $R_f$ 0.6 (Hex/EtOAc 1:1); $[\alpha]_D^{20}$ −31 (c 0.6, CHCl$_3$); $^1$H NMR (600 MHz, CDCl3) δ (ppm) 7.45-7.43 (m, 2H, 2×CH$_{Ar}$), 7.35-7.28 (m, 8H, 8×CH$_{Ar}$), 7.19 (m, 2H, 2×CH$_{PMB}$), 6.84 (m, 2H, 2×CH$_{PMB}$), 5.52 (s, 1H, H-7A), 5.43 (dd, J$_{2-3}$=3.2 Hz, J$_{2-1}$=1.6 Hz, 1H, H-2B), 5.17 (d, J=1.0 Hz, 1H, H-1B), 4.90-4.85 (m, 2H, H-4B, CHH$_{Ph}$), 4.69 (d, J=10.8 Hz, 1H, CHH$_{Ph}$), 4.58 (d, J=11.5 Hz, 1H, CHH$_{Ph}$), 4.50 (d, J=7.8 Hz, 1H, H-1A), 4.35 (dd, J$_{6a-6b}$=10.5 Hz, J$_{6a-5}$=5.0 Hz, 1H, H-6aA), 4.33 (d, J=11.6 Hz, 1H, CHH$_{Ph}$), 4.06 (m, 1H, H-5B), 3.96-3.92 (m, 1H, H-1a$_{linker}$), 3.90 (t, J=9.2 Hz, 1H, H-3A), 3.79-3.75 (m, 5H, H-3B, H-6bA, CH$_{3PMB}$), 3.59-3.56 (m, 1H, H-1b$_{linker}$), 3.53 (t, J=9.5 Hz, 1H, H-4A), 3.46 (t, J=8.1 Hz, 1H, H-2A), 3.44-3.39 (m, 1H, H-5A), 3.23 (t, J=6.9 Hz, 2H, H-5$_{linker}$), 2.71-2.66 (m, 1H, CHH$_{Lev}$), 2.62-2.57 (m, 1H, CHH$_{Lev}$), 2.48-2.43 (m, 1H, CHH$_{Lev}$), 2.42-2.38 (m, 1H, CHH$_{Lev}$), 2.15 (s, 3H, CH$_{3Lev}$), 2.05 (s, 3H, CH$_{3Ac}$), 1.70-1.65 (m, 2H, H-2$_{linker}$), 1.64-1.59 (m, 2H, H-4$_{linker}$), 1.50-1.44 (m, 2H, H-3) 0.78 (d, J=6.2 Hz, 3H, H-6B); $^{13}$C NMR (150 MHz, CDCl3) δ (ppm) 206.4 (CO$_{Lev}$), 172.0 (COOR$_{Lev}$), 170.2 (COOR$_{Ac}$), 159.3 (C$_{Ar}$), 137.9 (C$_{Ar}$), 137.2 (C$_{Ar}$), 130.4 (C$_{Ar}$), 129.5-126.3 (12C, 12×CH$_{Ar}$), 113.8 (2C, 2×CH$_{PMB}$), 104.3 (C-1A), 101.8 (C-7A), 98.4 (C-1B), 82.8 (C-2A), 79.3 (C-4A), 76.3 (C-3A), 75.0 (C-3B), 74.6 (CH$_{2Ph}$), 72.9 (C4B), 71.1 (CH$_{2Ph}$), 70.2 (C-1$_{linker}$), 68.9 (C-6A), 68.5 (C-2B), 66.5 (2C, C-5A, C-5B), 55.4 (CH$_{3PMB}$), 51.4 (C-5$_{linker}$), 37.9 (CH$_{2Lev}$), 30.0 (CH$_{3Lev}$), 29.5 (C-2$_{linker}$), 28.8 (C-4$_{linker}$), 28.1 (CH$_{2Lev}$), 23.5 (C-3) 21.1 (CH$_{3Ac}$), 17.0 (C-3$_{Lev}$, 6B); HRMS (ESI-TOF) m/z [M+Na]$^+$ calcd for C$_{46}$H$_{57}$N$_3$NaO$_{14}$ 898.3733; found 898.3756; m/z [M+NH$_4$]$^+$ calcd for C$_{46}$H$_{61}$N$_4$O$_{14}$ 893.4179; found 893.4196.

(5-Azido-1-pentyl) 2-O-acetyl-4-O-levulinoyl-α-L-rhamnopyranosyl-(1→3)-2-O-benzyl-4,6-O-benzylidene-β-D-glucopyranoside (12)

DDQ (609 mg, 2.68 mmol, 2.0 equiv) was added to a solution of disaccharide 26 (1175 mg, 1.342 mmol, 1.0 equiv) in DCM (27 mL) and H$_2$O (2.7 mL), and the mixture was stirred at rt for 2 h. Saturated NaHCO$_3$(aq) (40 mL) was added to quench the solution, which was then diluted in EtOAc (30 mL) and transferred in a separatory funnel. The organic layer was washed with saturated NaHCO$_3$(aq) (40 mL) and brine (40 mL), dried over anhydrous MgSO$_4$, and concentrated under reduced pressure. The residue was purified by silica gel flash chromatography (Hex/EtOAc 9:1 to 1:1) to give alcohol 12 (878 mg, 87%) as a white amorphous solid: $R_f$ 0.3 (Hex/EtOAc 4:6); $[\alpha]_D^{20}$ −43 (c 0.7, CHCl$_3$); $^1$H NMR (600 MHz, CDCl$_3$) δ (ppm) 7.47-7.46 (m, 2H, 2×CH$_{Ar}$), 7.35-7.34 (m, 3H, 3×CH$_{Ar}$), 7.32-7.31 (m, 4H, 4'CH$_{Ar}$), 7.28-7.27 (m, 1H, CH$_{Ar}$), 5.52 (s, 1H, H-7A), 5.22-5.19 (m, 1H, H-1B, H-2B), 4.87 (d, J=10.8 Hz, 1H, CHH$_{Bn}$), 4.79-4.73 (m, 1H, H-4B, CHH$_{Bn}$), 4.49 (d, J=7.8 Hz, 1H, H-1A), 4.35 (dd, J$_{6a-6b}$=10.5 Hz, J$_{6a-5}$=5.0 Hz, 1H, H-6aA), 4.13 (dq, J$_{5-4}$=10.1 Hz, J$_{5-6}$=6.2 Hz, 1H, H-5B), 4.04 (dd, J$_{3-4}$=9.8 Hz, J$_{3-2}$=3.2 Hz, 1H, H-3B), 3.95-3.90 (m, 2H, H-3A, H-1$_{linker}$) 3.77 (t J$_{6a-6b}$=10.3 Hz, 1H, H-6bA), 3.57-3.53 (m, 2H, H-4A, H-1b$_{linker}$), 3.47-3.40 (m, 2H, H-2A, H-5A), 3.22 (t, J=6.9 Hz, 2H, H-5$_{linker}$), 2.77-2.69 (m, 2H, CH$_{2Lev}$), 2.51-2.49 (m, 2H, CH$_{2Lev}$), 2.16 (s, 3H, CH$_{3Lev}$), 2.07 (s, 3H, CH$_{3Ac}$), 1.68-1.63 (m, 2H, H-2$_{linker}$), 1.62-1.58 (m, 2H, H-4$_{linker}$), 1.48-1.41 (m, 2H, H-3) 0.82 (d, J=6.2 Hz, 3H, H-6B); $^{13}$C NMR (150 MHz, CDCl$_3$) δ (ppm) 207.0 (CO$_{Lev}$), 173.2 (COOR$_{Lev}$), 170.5 (COOR$_{Ac}$), 138.1 (C$_{Ar}$), 137.3 (C$_{Ar}$), 129.2 (CH$_{Ar}$), 128.4 (2C, 2×CH$_{Ar}$), 128.3 (2C, 2×CH$_{Ar}$), 128.3 (2C, 2×CH$_{Ar}$), 127.9 (CH$_{Ar}$), 126.4 (2C, 2×CH$_{Ar}$), 104.3 (C-1A), 101.8 (C-7A), 97.8 (C-1B), 82.9 (C-2A), 79.3 (C-4A), 76.1 (C-3A), 75.2, 75.0 (2C, C-4B, CH$_{2Bn}$), 72.3 (C-2B), 70.2 (C-1$_{linker}$), 68.9 (C-6A), 68.6 (C-3B), 66.4 (C-5A), 65.8 (C-5B), 51.4 (C-5 linker), 38.2 (CH$_{2Lev}$), 29.9 (CH$_{3Lev}$), 29.4 (C-2$_{linker}$), 28.7 (C-4$_{linker}$), 28.2 (CH$_{2Lev}$), 23.5 (C-3$_{linker}$), 21.1 (CH$_{3Ac}$), 16.9 (C-6B); HRMS (ESI-TOF) m/z [M+Na]$^+$ calcd for C$_{38}$H$_{43}$N$_3$NaO$_{13}$ 778.3158; found 778.3159; m/z [M+K]$^+$ calcd for C$_{38}$H$_{43}$KN$_3$O$_{13}$ 794.2897; found 794.292.

(5-Azido-1-pentyl) 2-O-ortho-(azidomethyl)benzoyl-4,6-O-benzylidene-3-O-para-methoxybenzyl-β-D-glucopyranosyl-(1→3)-2-O-acetyl-4-O-levulinoyl-α-L-rhamnopyranosyl-(1→3)-2-O-benzyl-4,6-O-benzylidene-β-D-glucopyranoside (27)

Disaccharide 12 (583 mg, 0.772 mmol, 1.0 equiv), thioglucoside 18 (757 mg, 1.16 mmol, 1.5 equiv), and NIS (260 mg, 1.16 mmol, 1.5 equiv) were dried together under high vacuum for 1 h. 4 Å activated ground molecular sieves (2333 mg) and anhydrous DCM (15 mL) were successively added and the mixture was stirred under Ar for 1 h. The reaction flask was cooled at −10° C. and protected from light using aluminum foil. AgOTf (20 mg, 0.077 mmol, 0.1 equiv) was added and the mixture was stirred under Ar for 2 h while being gradually warmed to 0° C. Et$_3$N (0.11 mL, 0.77 mmol, 1.0 equiv) was added, the yellow suspension was filtered over Celite, and the solvents were evaporated under reduced pressure. The residue was purified by silica gel flash chromatography (Hex/EtOAc 8:2 to 7:3) to give trisaccharide 27 (872 mg, 88%) as a white solid foam: $R_f$ 0.7 (Hex/EtOAc 6:4); $[\alpha]_D^{20}$ −28 (c 0.6, CHCl$_3$); $^1$H NMR (600 MHz, CDCl$_3$) δ (ppm) 7.70 (m, 1H, CH$_{AZMB}$), 7.56 (m, 1H, CH$_{Ar}$), 7.51 (m, 2H, 2×CH$_{Ar}$), 7.41-7.25 (m, 15H, 15×CH$_{Ar}$), 7.07 (m, 2H, 2×CH$_{PMB}$), 6.62 (m, 2H, 2×CH$_{PMB}$), 5.60 (s, 1H, H-7C), 5.51 (s, 1H, H-7A), 5.35 (dd, J$_{2-3}$=3.4 Hz, J$_{2-1}$=1.5 Hz, 1H, H-2B), 5.19 (s, 1H, H-1B), 5.15-5.11 (m, 1H, H-2C), 4.89 (t, J=10.0 Hz, 1H, H-4B), 4.86 (d, J=10.7 Hz, 1H, CHH$_{Bn}$), 4.78-4.75 (m, 2H, CHH$_{Bn}$, CHH$_{PMB}$), 4.73-4.70 (m, 2H, CHH$_{AZMB}$, H-1C), 4.63 (d, J=15.1 Hz, 1H, CHH$_{AZMB}$), 4.59 (d, J=11.7 Hz, 1H, CHH$_{PMB}$), 4.49 (d, J=7.8 Hz, 1H, H-1A), 4.37 (dd, J$_{6a-6b}$10.5 Hz, J$_{6a-5}$=5.0 Hz, 1H, H-6aC), 4.34 (dd, J$_{6b-6a}$=10.5 Hz, J$_{6b-5}$=4.9 Hz, 1H, H-6aA), 4.06 (m, 1H, H-5B), 4.02 (dd, J$_{3-4}$=9.8 Hz, J$_{3-2}$=3.5 Hz, 1H, H-3B), 3.93-3.90 (m, 2H, H-3A, H-1a$_{linker}$) 3.83-3.81 (m, 2H, H-3C, H-4C), 3.80-3.75 (m, 2H, H-6bA, H-6bC), 3.70 (s, 3H, CH$_{3PMB}$), 3.58-3.53 (m, 2H, H-1$_{linker}$, H-4A), 3.51-3.46 (m, 2H, H-2A, H-5C), 3.42-3.38 (m, 1H, H-5A), 3.21 (t, J=6.9 Hz, 2H, H-5) 2.27 (m, 1H, CHH$_{Lev}$), 2.13-2.09 (m, 1H, CHH$_{Lev}$), 2.07 (s, 3H, CH$_{3Ac}$), 2.04-2.02 (m, 1H, CHH$_{Lev}$), 2.01 (s, 3H, CH3Lev), 1.80 (m, 1H, CHH$_{Lev}$), 1.67-1.63 (m, 2H, H-21inker), 1.66-1.57 (m, 2H, H-4$_{linker}$), 1.49-1.41 (m, 2H, H-3$_{linker}$), 0.75 (d, J=6.2 Hz, 3H, H-6B); $^{13}$C NMR (150 MHz, CDCl$_3$) δ (ppm) 206.1 (CO$_{Lev}$), 171.4 (COOR$_{Lev}$), 170.0 (COOR$_{Ac}$), 164.7 (COOR$_{AZMB}$), 159.2 (C$_{Ar}$), 138.2 (C$_{Ar}$), 138.0 (C$_{Ar}$), 137.3 (C$_{Ar}$), 137.1 (C$_{Ar}$), 132.7 (CH$_{AZMB}$), 130.7 (CH$_{Ar}$), 130.1 (C$_{Ar}$), 129.7 (2C, 2×CH$_{PMB}$), 129.2 (CH$_{Ar}$), 129.1-126.1 (17C, C$_{Ar}$, 16×CH$_{Ar}$), 113.6 (2C, 2×CH$_{PMB}$), 104.2 (C-1A), 101.7 (C-7A), 101.3 (C-7C), 101.1 (C-1C), 97.8 (C-1B), 82.7 (C-2A), 81.6 (C-4C), 79.2 (C-4A), 77.6 (C-3C), 76.0 (C-3A), 74.9 (2C, C-3B, CH$_{2Bn}$), 73.6, 73.5 (2C, C-2C, CH$_{2PMB}$), 72.5 (C-4B), 71.0 (C-2B), 70.2 (C-1$_{linker}$) 68.9, 68.7 (2C, C-6A, C-6C), 66.3, 66.17, 66.15 (3C, C-5A, C-5B, C-5C), 55.2 (CH$_{3PMB}$), 52.9 (CH$_{2AZMB}$), 51.3 (C-5$_{linker}$), 37.5 (CH$_{2Lev}$), 29.7 (CH$_{3Lev}$), 29.4 (C-2$_{linker}$), 28.7

(C-4$_{linker}$), 27.4 (CH$_{2Lev}$), 23.5 (C-3$_{linker}$), 21.0 (CH$_{3Ac}$), 16.7 (C-6B); HRMS (ESI-TOF) m/z [M+NH$_4$]$^+$ calcd for C$_{67}$H$_{80}$N$_7$O$_{20}$ 1302.5453; found 1302.5453; m/z [M+Na]$^+$ calcd for C$_{67}$H$_{76}$N$_6$NaO$_{20}$ 1307.5007; found 1307.5003.

(5-Azido-1-pentyl) 2-O-ortho-(azidomethyl)benzoyl-4,6-O-benzylidene-β-D-glucopyranosyl-(1→3)-2-O-acetyl-4-O-levulinoyl-α-L-rhamnopyranosyl-(1→3)-2-O-benzyl-4,6-O-benzylidene-β-D-glucopyranoside (28)

Trisaccharide 27 (99 mg, 0.077 mmol, 1.0 equiv) was dissolved in DCM (1.6 mL) and H$_2$O (0.2 mL) and DDQ (35 mg, 0.16 mmol, 2.0 equiv) was added. The mixture was stirred at rt for 2 h, then quenched with saturated NaHCO$_3$ (aq) (2 mL). The solution was transferred into a separatory funnel, DCM (10 mL) was added, and the organic and aqueous layers were separated. The aqueous phase was extracted with DCM (2×10 mL). The combined organic phases were washed with saturated NaHCO$_3$(aq) (20 mL) and brine (20 mL), dried over anhydrous MgSO$_4$, and concentrated under reduced pressure. The residue was purified by silica gel flash chromatography (Hex/EtOAc 8:2 to 4:6) to give alcohol 28 (68 mg, 75%) as a white solid foam: R$_f$ 0.6 (Hex/EtOAc 1:1); [α]$_D^{20}$ −62 (c 0.6, CHCl$_3$); $^1$H NMR (600 MHz, CDCl$_3$) δ (ppm) 7.89 (m, 1H, CH$_{AZMB}$), 7.55 (m, 1H, CH$_{Ar}$), 7.51-7.49 (m, 3H, 3×CH$_{Ar}$), 7.44 (m, 2H, 2×CH$_{Ar}$), 7.39-7.28 (m, 12H, 12×CH$_{Ar}$), 5.54 (s, 1H, H-7C), 5.53 (s, 1H, H-7A), 5.36 (d, J=1.9 Hz, 1H, H-2B), 5.20 (s, 1H, H-1B), 5.10-5.07 (m, 1H, H-2C), 4.92 (t, J=9.9 Hz, 1H, H-4B), 4.86 (d, J=10.7 Hz, 1H, CHH$_{Bn}$), 4.78-4.73 (m, 3H, H-1C, CHH$_{Bn}$, CHH$_{AZMB}$), 4.69 (d, J=14.7 Hz, 1H, CHH$_{AZMB}$), 4.48 (d, J=7.7 Hz, 1H, H-1A), 4.37-4.33 (m, 2H, H-6aA, H-6aC), 4.11-4.07 (m, 1H, H-5B), 4.05 (dd, J$_{3-4}$=9.8 Hz, J$_{3-2}$=3.5 Hz, 1H, H-3B), 3.99 (t, J=9.0 Hz, 1H, H-3C), 3.94-3.89 (m, 2H, H-1a$_{linker}$, $_H$3A), 3.78-3.75 (m, 2H, H-6bA, H-6bC), 3.62 (t, J=9.3 Hz, 1H, H-4C), 3.58-3.53 (m, 2H, H-1b$_{linker}$, H-4A), 3.51-3.46 (m, 2H, H-2A, H-5C), 3.40 (td, J$_{5-4}$=9.7 Hz, J$_{5-6}$=5.0 Hz, 1H, H-5A), 3.21 (t, J=6.9 Hz, 2H, H-5) 2.87 (br s, 1H, OH), 2.28-2.22 (m, 1H, CHH$_{Lev}$), 2.17-2.12 (m, 1H, CHH$_{Lev}$), 2.09 (s, 3H, CH$_{3Ac}$), 2.07-2.03 (m, 1H, CHH$_{Lev}$), 2.01 (s, 3H, CH$_{3Lev}$), 1.86 (m, 1H, CHH$_{Lev}$), 1.67-1.62 (m, 2H, H-2$_{linker}$), 1.62-1.57 (m, 2H, H-4$_{linker}$), 1.48-1.41 (m, 2H, H-3$_{linker}$), 0.78 (d, J=6.2 Hz, 3H, H-6B); $^{13}$C NMR (150 MHz, CDCl$_3$) δ (ppm) 206.2 (CO$_{Lev}$), 171.5 (COOR$_{Lev}$), 170.0 (COOR$_{Ac}$), 165.6 (COOR$_{AZMB}$), 138.0 (C$_{Ar}$), 137.5 (C$_{Ar}$), 137.1 (C$_{Ar}$), 137.0 (C$_{Ar}$), 132.7-126.2 (20C, C$_{Ar}$, 19×CH$_{Ar}$), 104.2 (C-1A), 101.9, 101.7 (2C, C-7A, C-7C), 101.0 (C-1C), 97.7 (C-1B), 82.6 (C-2A), 80.7 (C-4C), 79.2 (C-4A), 76.1 (C-3A), 75.0, 74.9, 74.8 (3C, CH$_{2Bn}$, C-3B, C-2C), 72.7 (C-4B), 72.2 (C-3C), 71.1 (C-2B), 70.2 (C-1$_{linker}$), 68.9, 68.6 (2C, C-6A, C-6C), 66.3, 66.2 (3C, C-5A, C-5B, C-5C), 53.0 (CH$_{2AZMB}$), 51.3 (C-5$_{linker}$), 37.4 (CH$_{2Lev}$), 29.7 (CH$_{3Lev}$), 29.4 (C-2$_{linker}$), 28.7 (C-4$_{linker}$), 27.5 (CH$_{2Lev}$), 23.4 (C-3$_{linker}$), 21.0 (CH$_{3Ac}$), 16.8 (C-6B); HRMS (ESI-TOF) m/z [M+Na]$^+$ calcd for C$_{59}$H$_{68}$N$_6$NaO$_{19}$ 1187.4431; found 1187.4412.

para-Methylphenyl 2-O-acetyl-4-O-levulinoyl-3-O-methyl-1-thio-α-L-rhamnopyranoside (29)

Bu$_2$SnO (1557 mg, 6.254 mmol, 1.1 equiv) was added to a solution of diol 24 (2095 mg, 5.686 mmol, 1.0 equiv) in toluene (23 mL) and the mixture was refluxed with a Dean-Stark trap for 5 h. The solution was cooled to rt, and CsF (881 mg, 5.80 mmol, 1.02 equiv) and MeI (17.7 mL, 284 mmol, 50.0 equiv) were successively added. The mixture was stirred under Ar at 80° C. for 16 h. The suspension was cooled at 0° C., filtered over Celite, and rinsed with DCM. The solvents were concentrated under reduced pressure. The residue was purified by silica gel flash chromatography (Hex/EtOAc 1:1) to give para-methylphenyl 4-O-levulinoyl-3-O-methyl-1-thio-α-L-rhamnopyranoside (2019 mg, 93%, ~83:17 mixture with its inseparable 2-O-methyl anomer) as a colorless oil: R$_f$ 0.3 (Hex/EtOAc 4:6); $^1$H NMR (600 MHz, CDCl$_3$) δ (ppm) 7.36-7.35 (m, 2H, 2×CH$_{STol}$), 7.13-7.11 (m, 2H, 2×CH$_{STol}$), 5.49 (d, J=1.4 Hz, 1H, H-1), 5.05 (t, J=9.5 Hz, 1H, H-4), 4.31 (dd, J$_{2-3}$=3.2 Hz, J$_{2-4}$=1.6 Hz, 1H, H-2), 4.29-4.24 (m, 1H, H-5), 3.53 (dd, J$_{3-4}$=9.4 Hz, J$_{3-2}$=3.3 Hz, 1H, H-3), 3.45 (s, 3H, CH$_{3OMe}$), 2.82-2.76 (m, 2H, CH$_{2Lev}$), 2.63-2.59 (m, 2H, CH$_{2Lev}$), 2.33 (s, 3H, CH$_{3STol}$), 2.20 (s, 3H, CH$_{3Lev}$), 1.20 (d, J=6.3 Hz, 3H, H-6); $^{13}$C NMR (150 MHz, CDCl$_3$) δ (ppm) 206.6 (CO$_{Lev}$), 172.2 (COOR$_{Lev}$), 137.8 (C$_{STol}$), 132.1 (2C, 2×CH$_{STol}$), 130.02 (C$_{STol}$), 129.97 (2C, 2×CH$_{STol}$), 87.4 (C-1), 79.2 (C-3), 73.0 (C-4), 69.2 (C-2), 67.4 (C-5), 57.8 (CH$_{3OMe}$), 38.0 (CH$_{2Lev}$), 29.9 (CH$_{3Lev}$), 28.1 (CH$_{2Lev}$), 21.2 (CH$_{3STol}$); HRMS (ESI-TOF) m/z [M+NH$_4$]$^+$ calcd for C$_{19}$H$_{30}$NO$_6$S 400.1788; found 400.1806; m/z [M+Na]$^+$ calcd for C$_{19}$H$_{26}$NaO$_6$S 405.1342; found 405.1362. The latter alcohol (1678 mg, 4.387 mmol, 1.0 equiv) was dissolved in anhydrous pyridine (22 mL) and Ac$_2$O (22 mL), and DMAP (5 mg, 0.04 mmol, 0.01 equiv) was added. The reaction mixture was stirred at rt for 16 h under Ar. The solution was concentrated under reduced pressure and co-evaporated with toluene (3×). The residue was purified by silica gel flash chromatography (Hex/EtOAc 5:5 to 4:6) to give thiorhamnoside 29 (1786 mg, 96%, 9:1 mixture with its inseparable 3-O-acetyl-2-O-methyl isomer) as a white amorphous solid: R$_f$ 0.6 (Hex/EtOAc 4:6); $^1$H NMR (600 MHz, CDCl$_3$) δ (ppm) 7.36-7.35 (m, 2H, 2×CH$_{STol}$), 7.13-7.12 (m, 2H, 2×CH$_{STol}$), 5.57 (dd, J$_{2-3}$=3.2 Hz, J$_{2-1}$=1.6 Hz, 1H, H-2), 5.36 (d, J$_{1-2}$=1.3 Hz, 1H, H-1), 5.04 (t, J=9.8 Hz, 1H, H-4), 4.30 (m, 1H, H-5), 3.59 (dd, J$_{3-4}$=9.8 Hz, J$_{3-2}$=3.3 Hz, 1H, H-3), 3.37 (s, 3H, CH$_{3OMe}$), 2.84-2.84 (m, 1H, CHH$_{Lev}$), 2.76-2.71 (m, 1H, CHH$_{Lev}$), 2.69-2.63 (m, 1H, CHH$_{Lev}$), 2.61-2.57 (m, 1H, CHH$_{Lev}$), 2.33 (s, 3H, CH$_{3STol}$), 2.20 (s, 3H, CH$_{3Lev}$), 2.11 (s, 3H, CH$_{3Ac}$), 1.23 (d, J=6.3 Hz, 3H, H-6); $^{13}$C NMR (150 MHz, CDCl$_3$) δ (ppm) 206.5 (CO$_{Lev}$), 172.2 (COOR$_{Lev}$), 170.4 (COOR$_{Ac}$), 138.2 (C$_{Stol}$), 132.4 (2C, 2×CH$_{STol}$), 130.1 (2C, 2×CH$_{STol}$), 129.9 (C$_{STol}$), 86.6 (C-1), 77.6 (C-3), 73.0 (C-4), 69.7 (C-2), 67.8 (C-5), 57.9 (CH$_{3OMe}$), 38.0 (CH$_{2Lev}$), 30.0 (CH$_{3Lev}$), 28.1 (CH$_{2Lev}$), 21.2 (CH$_3$), 21.1 (CH$_3$), 17.4 (C-6); HRMS (ESI-TOF) m/z [M+NH$_4$]$^+$ calcd for C$_{21}$H$_{32}$NO$_7$S 442.1894; found 442.19005; m/z [M+Na]$^+$ calcd for C$_{21}$H$_{28}$NaO$_7$S 447.1448; found 447.1453.

(5-Azido-1-pentyl) 2-O-acetyl-4-O-levulinoyl-3-O-methyl-α-L-rhamnopyranosyl-(1→3)-2-O-ortho-(azidomethyl)benzoyl-4,6-O-benzylidene-3-D-glucopyranosyl-(1→3)-2-O-acetyl-4-O-levulinoyl-α-L-rhamnopyranosyl-(1→3)-2-O-benzyl-4,6-O-benzylidene-3-D-glucopyranoside (10)

Trisaccharide 28 (300 mg, 0.257 mmol, 1.0 equiv), thiorhamnoside 29 (164 mg, 0.386 mmol, 1.5 equiv) and NIS (87 mg, 0.39 mmol, 1.5 equiv) were dried together under high vacuum for 1 h. 4 Å activated ground molecular sieves (1200 mg) and anhydrous DCM (5 mL) were successively added and the mixture was stirred under Ar for 1 h. The reaction flask was cooled at 10° C. and protected from light using aluminum foil. AgOTf (7 mg, 0.03 mmol, 0.1 equiv) was added and the mixture was stirred under Ar for 2 h while being gradually warmed to 0° C. Et$_3$N (0.04 mL, 0.3 mmol, 1.0 equiv) was added, the yellow suspension was filtered over Celite, and the solvents were evaporated under reduced pressure. The residue was purified by silica gel flash chromatography (Hex/EtOAc 6:4 to 5:5) to give tetrasaccharide 10 (291 mg, 77%) as a white amorphous solid: $R_f$ 0.5 (Hex/EtOAc 4:6); $[\alpha]_D^{20}$ 62 (c 0.4, CHCl$_3$); $^1$H NMR (600 MHz, CDCl$_3$) δ (ppm) 7.86 (m, 1H, CH$_{AZMB}$), 7.59-7.55 (m, 2H, 2×CH$_{Ar}$), 7.48 (m, 2H, 2×CH$_{Ar}$), 7.43-7.42 (m, 2H, 2×CH$_{Ar}$), 7.38-7.29 (m, 12H, 12×CH$_{Ar}$), 5.57 (s, 1H, H-7C), 5.53 (s, 1H, H-7A), 5.36 (d, J=1.7 Hz, 1H, H-2B), 5.21-5.19 (m, 2H, H-1B, H-2C), 5.07 (d, J=1.1 Hz, 1H, H-2D), 4.91-4.87 (m, 2H, CHH$_{Bn}$, H-4B), 4.86-4.76 (m, 6H, CHH$_{Bn}$, H-1C, H-1D, CH$_{2AZMB}$, H-4D), 4.49 (d, J=7.7 Hz, 1H, H-1A), 4.39 (dd, J$_{6a-6b}$=10.5 Hz, J$_{6a-6}$=4.9 Hz, 1H, H-6aC), 4.35 (dd, J$_{6a-6b}$=10.2 Hz, J$_{6a-5}$=4.9 Hz, 1H, H-6aA), 4.10-4.03 (m, 3H, H-3B, H-30, H-5B), 4.03-4.00 (m, 1H, H-5D), 3.94-3.90 (m, 2H, H-1a$_{linker}$, H-3A), 3.82-3.75 (m, 2H, H-6bA, H-6bC), 3.72 (t, J=9.4 Hz, 1H, H-4C), 3.59-3.52 (m, 3H, H-1b$_{linker}$, H-4A, H-5C), 3.50-3.47 (m, 2H, H-2A, H-3D), 3.41 (td, J=9.6 Hz, J=4.9 Hz, 1H, H-5A), 3.24 (t, J=14.2 Hz, 2H, H-5$_{linker}$), 3.21 (s, 3H, CH$_{3OMe}$), 2.78-2.73 (m, 1H, CHH$_{Lev}$), 2.67-2.62 (m, 1H, CHH$_{Lev}$), 2.56-2.47 (m, 2H, CH$_{2Lev}$), 2.32-2.29 (m, 1H, CHH$_{Lev}$), 2.16 (s, 3H, CH$_{3Lev}$), 2.13-2.11 (m, 2H, CH$_{2Lev}$), 2.08 (s, 3H, CH$_{3Ac}$), 2.04 (s, 3H, CH$_{3Lev}$), 1.87-1.80 (m, 4H, CH$_{3Ac}$, CHH$_{Lev}$), 1.68-1.63 (m, 2H, H-2$_{linker}$), 1.62-1.58 (m, 2H, H-4$_{linker}$), 1.48-1.42 (m, 2H, H3$_{linker}$), 0.77-0.76 (m, 6H, H-6B, H-6D); $^{13}$C NMR (150 MHz, CDCl$_3$) δ (ppm) 206.4 (CO$_{Lev}$), 206.1 (CO$_{Lev}$), 171.0 (COOR$_{Lev}$), 171.4 (COOR$_{Lev}$), 170.0 (COOR$_{Ac}$), 169.5 (COOR$_{Ac}$), 164.4 (COOR$_{AZMB}$), 139.2 (C$_{Ar}$), 138.0 (C$_{Ar}$), 137.1 (C$_{Ar}$), 137.0 (C$_{Ar}$), 133.1-126.2 (20C, C$_{Ar}$, 19×CH$_{Ar}$), 104.2 (C-1A), 101.8, 101.7 (2C, C-7A, C-7C), 100.9 (C-1C), 98.2 (C-1D), 97.7 (C-1B), 82.7 (C-2A), 79.2 (C-4A), 79.0 (C-4C), 76.7 (C-3D), 76.6 (C-3C), 76.1 (C-3A) 74.9, 74.7, 74.5 (3C, C-3B, CH$_{2Bn}$, C-2C), 72.6 (2C, C-4B, C-4D), 71.0 (C-2B), 70.2 (C-1$_{linker}$), 68.9, 68.7 (2C, C-6A, C-6C), 67.74 (C-2D), 66.71, 66.4, 66.3, 66.1 (4C, C-5A, C-5B, C-5C, C-5D), 57.6 (CH$_{3OMe}$), 53.0 (CH$_{2AZMB}$), 51.3 (C-5$_{linker}$), 37.9 (CH$_{2Lev}$), 37.4 (CH$_{2Lev}$), 29.9 (CH$_{3Lev}$), (CH$_{3Lev}$), 29.7 (CH$_{3Lev}$), 29.4 (C-2$_{linker}$), 28.7 (C-4$_{linker}$), 28.0 (CH$_{2Lev}$), 27.4 (CH$_{2Lev}$), 23.4 (C-3$_{linker}$), 21.0, 20.6 (2C, 2×CH$_{3Ac}$), 16.8, 16.7 (2C, C-6B, C-6D); HRMS (ESI-TOF) m/z [M+NH$_4$]$^+$ calcd for C$_{73}$H$_{92}$N$_7$O$_{26}$ 1482.6087; found 1482.6047; m/z [M+Na]$^+$ calcd for C$_{73}$H$_{88}$N$_6$NaO$_{26}$ 1487.564; found 1487.5617.

(5-Azido-1-pentyl) 2-O-acetyl-3-O-methyl-α-L-rhamnopyranosyl-(1→3)-2-O-ortho-(azidomethyl)benzoyl-4,6-O-benzylidene-β-D-glucopyranosyl-(1→3)-2-O-acetyl-α-L-rhamnopyranosyl-(1→3)-2-O-benzyl-4,6-O-benzylidene-β-D-glucopyranoside (30)

A solution of tetrasaccharide 10 (214 mg, 0.146 mmol, 1.0 equiv) in anhydrous pyridine (1 mL) was cooled at 0° C. Acetic acid (0.6 mL) and hydrazine monohydrate (0.07 mL, 1 mmol, 10.0 equiv) were successively slowly added. The mixture was stirred for 16 h under Ar while gradually being warmed to rt. The solution was concentrated under reduced pressure and co-evaporated with toluene (3×). The residue was purified by silica gel flash chromatography (Tol/EtOAc 9:1 to 7:3) to give diol 30 (160 mg, 86%) as a white amorphous solid: $R_f$ 0.5 (Tol/EtOAc 1:1); $[\alpha]_D^{20}$ −40 (c 1.0, AcOEt); $^1$H NMR (600 MHz, CDCl$_3$) δ (ppm) 7.97-7.95 (m, 1H, CH$_{AZMB}$), 7.55-7.52 (m, 1H, 3×CH$_{Ar}$), 7.50-7.47 (m, 3H, 3×CH$_{Ar}$), 7.40-7.39 (m, 2H, 2×CH$_{Ar}$), 7.36-7.31 (m, 8H, 8×CH$_{Ar}$), 7.29-7.27 (m, 2H, 2×CH$_{Ar}$), 7.25-7.23 (m, 2H, 2×CH$_{Ar}$), 5.55 (s, 1H, H-7A), 5.49 (s, 1H, H-7C), 5.32 (dd, J$_{2-3}$=3.5 Hz, J$_{2-1}$=1.6 Hz, 1H, H-2B), 5.30-5.27 (m, 1H, H-2C), 5.14 (d, J=1.2 Hz, 1H, H-1B), 5.08 (dd, J$_{2-3}$=3.2 Hz, J$_{2-1}$=1.7 Hz, 1H, H-2D), 4.92-4.74 (m, 6H, CH$_{2AZMB}$, CH$_{2Bn}$, H-1D, H-1C), 4.48 (d, J=7.8 Hz, 1H, H-1A), 4.37 (dd, J$_{6a-6b}$=10.6 Hz, J$_{6a-5}$=4.9 Hz, 1H, H-6aC), 4.33 (dd, J$_{6a-6b}$=10.4 Hz, J$_{6a-5}$=4.9 Hz, 1H, H-6aA), 4.07 (t, J=9.0 Hz, 1H, H-3C), 3.97-3.89 (m, 4H, H-1a$_{linker}$, H-5B, H-5D, H-3A), 3.87 (dd, J$_{3-4}$=9.4 Hz, J$_{3-2}$=3.6 Hz, 1H, H-3B), 3.77-3.69 (m, 3H, H-6bA, H-6bC, H-4C), 3.57-3.51 (m, 3H, H-1b$_{linker}$, H-5C, H-4A), 3.48-3.44 (m, 2H, H-2A, H-4B), 3.40-3.38 (m, 2H, H-3D, H-5A), 3.35-3.31 (m, 1H, H-4D), 3.29 (s, 3H, CH$_{3OMe}$), 3.20 (t, J=6.9 Hz, 2H, H-5) 2.41 (s, 1H, OH), 2.25 (s, 1H, OH), 2.04 (s, 3H, CH$_{3Ac}$), 1.80 (s, 3H, CH$_{3Ac}$), 1.66-1.61 (m, 2H, H-2$_{linker}$), 1.61-1.56 (m, 2H, H-4$_{linker}$), 1.47-1.40 (m, 2H, H-3$_{linker}$), 0.90 (d, J=6.2 Hz, 3H, H-6B*), 0.86 (d, J=6.2 Hz, 3H, H-6D*); $^{13}$C NMR (150 MHz, CDCl$_3$) δ (ppm) 169.9 (COOR$_{Ac}$), 169.6 (COOR$_{Ac}$), 165.2 (COOR$_{AZMB}$), 138.6 (C$_{Ar}$), 138.2 (C$_{Ar}$), 137.1 (C$_{Ar}$), 137.0 (C$_{Ar}$), 133.3-126.2 (20C, CA, 19×CH$_{Ar}$), 104.2 (C-1A), 101.8, 101.5 (2C, C-7A, C-7C), 101.4 (C-1C), 98.5 (C-1D), 98.1 (C-B), 82.8 (C-2A), 79.3, 79.2 (2C, C-4A, C-3D), 78.2 (2C, C-3B, C-4C), 76.6, 76.5 (2C, C-3A, C-3C), 75.1, 74.9 (2C, CH$_{2Bn}$, C-2C), 71.7, 71.5 (2C, C-4B, C-4D), 70.7 (C-2B), 70.2 (C-1$_{linker}$), 68.8, 68.6 (2C, C-6A, C-6C), 68.5, 67.8 (2C, C-5B, C-5D), 67.3 (C-2D), 66.5 (C-5C), 66.3 (C-5A), 57.3 (CH$_{3OMe}$), 53.3 (CH$_{2AZMB}$), 51.3 (C-1$_{linker}$), 29.4 (C-2$_{linker}$), 28.7 (C-4$_{linker}$), 23.4 (C-3) 21.0 (CH$_{3Ac}$), 20.6 (CH$_{3Ac}$), 17.14, 17.07 (2C, C-6B, C-6D); HRMS (ESI-TOF) m/z [M+NH$_4$]$^+$ calcd for C$_{63}$H$_{80}$N$_7$O$_{22}$ 1286.5351; found 1286.5342; m/z [M+Na]$^+$ calcd for C$_{63}$H$_{76}$N$_6$NaO$_{22}$ 1291.4905; found 1291.4892.

para-Methylphenyl 2-O-acetyl-3-O-methyl-1-thio-α-L-rhamnopyranoside (32)

A solution of thiorhamnoside 29 (876 mg, 2.06 mmol, 1.0 equiv) in anhydrous pyridine (13 mL) was cooled at 0° C. Acetic acid (8.5 mL) and hydrazine monohydrate (0.5 mL, 10 mmol, 5.0 equiv) were successively slowly added. The mixture was stirred for 16 h under Ar while gradually being warmed to rt. The solution was concentrated under reduced pressure and co-evaporated with toluene (3×). The residue was purified by silical gel flash chromatography (Hex/EtOAc 7:3 to 6:4) to give alcohol 32 (616 mg, 91%, 83:17 mixture with its inseparable 3-O-acetyl-2-O-methyl isomer) as a colorless oil: $R_f$ 0.5 (Hex/EtOAc 4:6); $^1$H NMR (600 MHz, CDCl$_3$) δ (ppm) 7.36-7.35 (m, 2H, 2×CH$_{STol}$), 7.13-7.12 (m, 2H, 2×CH$_{STol}$), 5.56 (dd, J$_{2-3}$=3.1 Hz, J$_{2-1}$=1.5 Hz, 1H, H-2), 5.35 (d, J=1.2 Hz, 1H, H-1), 4.23-4.18 (m, 1H, H-5), 3.58 (td, J$_{4-3,4-5}$=9.4 Hz, J$_{4-CH}$=2.0 Hz, 1H, H-4), 3.47 (dd, J$_{3-4}$=9.4 Hz, J$_{3-2}$=3.1 Hz, 1H, H-3), 3.43 (s, 3H, CH$_{3OMe}$), 2.50 (d, J=2.2 Hz, 1H, OH), 2.33 (s, 3H, CH$_{3STol}$), 2.11 (s, 3H, CH$_{3Ac}$), 1.36 (d, J=6.2 Hz, 3H, H-6); $^{13}$C NMR (150 MHz, CDCl$_3$) δ (ppm) 170.3 (COOR$_{Ac}$), 138.1 (C$_{STol}$), 132.4 (2C, 2×CH$_{STol}$), 130.1 (C$_{STol}$), 130.0 (2C, 2×CH$_{STol}$), 86.8 (C-1), 80.1 (C-3), 72.1 (C-4), 69.4, 69.3 (2C, C-2, C-5), 57.5 (CH$_{3STol}$), 21.3 (CH$_3$), 21.2 (CH$_3$), 17.7 (C-6); HRMS (ESI-TOF) m/z [M+Na]$^+$ calcd for C$_{16}$H$_{22}$NaO$_5$S 349.10802; found 349.1078.

para-Methylphenyl 2-O-acetyl-6-deoxy-3-O-methyl-1-thio-α-L-talopyranoside (33)

A solution of anhydrous DMSO (0.57 mL, 8.0 mmol, 5.0 equiv) in anhydrous DCM (16 mL) was cooled at −10° C. and PDCP (0.72 mL, 4.8 mmol, 3.0 equiv) and Et$_3$N (1.11 mL, 7.98 mmol, 5.0 equiv) were successively added. A solution of alcohol 32 (521 mg, 1.60 mmol, 1.0 equiv) in anhydrous DCM (8 mL) was added dropwise during 1 h. The mixture was stirred at −10° C. for 10 min under Ar, and for an additional 30 min while gradually being warmed to rt. ater (50 mL) was added to the solution, which was then transferred to a separatory funnel. The organic and aqueous layers were separated, and the aqueous phase was extracted with DCM (3×30 mL). The combined organic layers were washed with brine (50 mL), then dried over anhydrous MgSO$_4$, and concentrated under reduced pressure. The resulting ketone was solubilized in MeOH (16 mL) and cooled at −10° C. NaBH$_4$ (109 mg, 2.87 mmol, 1.8 equiv) was slowly added and the mixture was stirred for 1 h while gradually being warmed to 0° C. The solution was diluted with DCM (50 mL), transferred in a separatory funnel, and washed with water (30 mL). The aqueous phase was extracted with DCM (3×30 mL), the combined organic phases were washed with brine (60 mL) and dried over anhydrous MgSO$_4$. The solution was concentrated under reduced pressure and the residue was purified by silica gel flash chromatography (Tol/EtOAc 95:5 to 85:15) to give taloside 33 (371 mg, 71%, 2 steps) as a colorless oil: R$_f$ 0.4 (Tol/EtOAc 1:1); $[\alpha]_D^{20}$+268 (c 0.4, CHCl$_3$); $^1$H NMR (600 MHz, CDCl3) δ (ppm) 7.37-7.35 (m, 2H, 2×CH$_{STol}$), 7.14-7.12 (m, 2H, 2×CH$_{STol}$), 5.46 (m, 1H, H-2), 5.41 (brs, 1H, H-1), 4.42-4.38 (m, 1H, H-5), 3.83 (dd, J$_{4-OH}$=9.1 Hz, J$_{4-5,4-3}$=3.2 Hz, 1H, H-4), 3.55 (t, J=3.5 Hz, 1H, H-3), 3.46 (s, 3H, CH$_{3OMe}$), 2.46 (d, J=9.3 Hz, 1H, OH), 2.33 (s, 3H, CH$_{3STol}$), 2.14 (s, 3H, CH$_{3Ac}$), 1.36 (d, J=6.5 Hz, 3H, H-6); $^{13}$C NMR (150 MHz, CDCl3) δ (ppm) 169.6 (COOR$_{Ac}$), 138.3 (C$_{STol}$), 132.5 (2C, 2×CH$_{STol}$), 130.1 (2C, 2×CH$_{STol}$), 129.8 (C$_{STol}$), 86.9 (C-1), 75.0 (C-3), 70.2 (C-2), 69.7 (C-4), 68.4 (C-5), 56.5 (CH$_{3OMe}$), 21.2 (2C, 2×CH$_3$), 16.5 (C-6); HRMS (ESI-TOF) m/z [M+Na]$^+$ calcd for C$_{16}$H$_{22}$NaO$_5$S 349.10802; found 349.10839.

para-Methylphenyl 2,4-O-di-acetyl-6-deoxy-3-O-methyl-1-thio-α-L-talopyranoside (34)

Alcohol 33 (197 mg, 0.613 mmol, 1.0 equiv) was solubilized in EtOAc (6 mL) and Ac$_2$O (0.58 mL, 6.1 mmol, 10.0 equiv) and DMAP (8 mg, 0.06 mmol, 0.1 equiv) were added. The mixture was refluxed for 3 h under Ar. The solvents were concentrated under reduced pressure and co-evaporated with toluene (3×). The residue was purified by silica gel flash chromatography (Hex/EtOAc 9:1 to 7:3) to give compound 34 (200 mg, 90%) as a white amorphous solid: R$_f$ 0.6 (Hex/EtOAc 1:1); $[\pi]_D^{20}$−137 (c 0.7, CHCL$_3$); $^1$H NMR (600 MHz, CDCl$_3$) δ (ppm) 7.35-7.34 (m, 2H, 2×CH$_{STol}$), 7.13-7.11 (m, 2H, 2×CH$_{STol}$), 5.48 (s, 1H, H-1), 5.40 (d, J=3.7 Hz, 1H, H-2), 5.31 (d, J=3.4 Hz, 1H, H- 4), 4.52 (dq, J$_{5-6}$=6.3 Hz, J$_{5-4}$=0.8 Hz, 1H, H-5), 3.59 (t, J=3.6 Hz, 1H, H-3), 3.40 (s, 3H, CH$_{3OMe}$), 2.33 (s, 3H, CH$_{3STol}$), 2.16 (s, 3H, CH$_{3Ac}$), 2.13 (s, 3H, CH$_{3Ac}$), 1.21 (d, J=6.5 Hz, 3H, H-6); $^{13}$C NMR (150 MHz, CDCl$_3$) δ (ppm) 170.8 (COOR$_{Ac}$), 170.4 (COOR$_{Ac}$), 138.0 (C$_{STol}$), 132.0 (2C, 2×CH$_{STol}$), 130.0 (2C, 2×CH$_{STol}$), 129.8 (C$_{STol}$), 86.9 (C-1), 74.51 (C-3), 68.6, 68.5 (2C, C-2, C-4), 66.5 (C-5), 57.4 (CH$_{3OMe}$), 21.3, 21.2 (2C, 2×CH$_3$), 21.0 (CH$_3$), 16.4 (C-6); HRMS (ESI-TOF) m/z [M+Na]$^+$ calcd for C$_{18}$H$_{24}$NaO$_6$S 391.11858; found 391.11991.

para-Methylphenyl 2-O-acetyl-4-O-chloroacetyl-6-deoxy-3-O-methyl-1-thio-α-L-talopyranoside (35)

Chloroacetic anhydride (268 mg, 1.57 mmol, 5.0 equiv) and DMAP (4 mg, 0.03 mmol, 0.1 equiv) were added to a solution of alcohol 33 (102 mg, 0.313 mmol, 1.0 equiv) in EtOAc (3 mL). The mixture was refluxed for 1 h under Ar, then diluted with EtOAc (3 mL). The solution was poured into a separatory funnel, washed with saturated NaHCO$_3$ (aq) (3×5 mL) and brine (5 mL), and dried over anhydrous MgSO$_4$. The solvents were concentrated under reduced pressure. The residue was purified by silica gel flash chromatography (Hex/EtOAc 8:2 to 7:3) to give compound 35 (120 mg, 95%) as a yellow oil: R$_f$ 0.4 (Hex/EtOAc 7:3); $[\alpha]_D^{20}$−107 (c 1.0, CHCl$_3$); $^1$H NMR (600 MHz, CDCl$_3$) δ (ppm) 7.35-7.33 (m, 2H, 2×CH$_{STol}$), 7.13-7.12 (m, 2H, 2×CH$_{STol}$), 5.48 (d, J=1.0 Hz, 1H, H-1), 5.41-5.38 (m, 1H, H-2), 5.37 (d, J=3.5 Hz, 1H, H-4), 4.56 (dq, J$_{5-6}$=6.5 Hz, J$_{5-4}$=1.1 Hz, 1H, H-5), 4.19 (d, J=14.9 Hz, 1H, CHH$_{AcCl}$) 4.14 (d, J=14.9 Hz, 1H, CHH$_{AcCl}$), 3.62 (t, J=3.6 Hz, 1H, H-3), 3.40 (s, 3H, CH$_{3OMe}$), 2.33 (s, 3H, CH$_{3STol}$), 2.13 (s, 3H, CH$_{3Ac}$), 1.23 (d, J=6.5 Hz, 3H, H-6); $^{13}$C NMR (150 MHz, CDCl$_3$) δ (ppm) 170.4 (COOR$_{Ac}$), 167.3 (COOR$_{AcCl}$), 138.2 (C$_{Ar}$), 132.2 (2C, 2×CH$_{STol}$), 130.1 (2C, 2×CH$_{STol}$), 129.6 (C$_{Ar}$), 86.8 (C-1), 74.2 (C-3), 70.5 (C-4), 68.3 (C-2), 66.2 (C-5), 57.4 (CH$_{3OMe}$), 40.9 (CH$_{2AcCl}$), 21.3, 21.2 (2C, 2×CH$_3$), 16.3 (C-6); HRMS (ESI-TOF) m/z [M+Na]$^+$ calcd for C$_{18}$H$_{23}$ClNaO$_6$S 425.07961; found 425.07992.

(5-Azido-1-pentyl) 2,4-O-di-acetyl-6-deoxy-3-O-methyl-α-L-talopyranosyl-(1→3)-2-O-ortho-(azidomethyl)benzoyl-4,6-O-benzylidene-β-D-glucopyranosyl-(1→3)-2-O-acetyl-4-O-levulinoyl-α-L-rhamnopyranosyl-(1→3)-2-O-benzyl-4,6-O-benzylidene-β-D-glucopyranoside (36)

Trisaccharide 29 (101 mg, 0.0867 mmol, 1.0 equiv), thiotaloside 34 (47 mg, 0.13 mmol, 1.5 equiv) and NIS (29 mg, 0.13 mmol, 1.5 equiv) were dried together under high vacuum for 1 h. 4 Å activated ground molecular sieves (400 mg) and anhydrous DCM (1.7 mL) were successively added and the mixture was stirred under Ar for 1 h. The reaction flask was cooled to −10° C. and protected from light using aluminum foil. AgOTf (2 mg, 0.009 mmol, 0.1 equiv) was added and the mixture was stirred under Ar for 2 h while being gradually warmed to 0° C. Et$_3$N (0.01 mL, 0.09 mmol, 1.0 equiv) was added, the yellow suspension was filtered over Celite, and the solvents were evaporated under reduced pressure. The residue was purified by silica gel flash chromatography (Hex/EtOAc 8:2 to 5:5) to give tetrasaccharide 36 (106 mg, 87%) as a white amorphous solid: R$_f$0.5 (Hex/EtOAc 4:6); $[\alpha]_D^{20}$−54 (c 0.6, CHCl$_3$); $^1$H NMR (600 MHz, CDCl$_3$) δ (ppm) 7.86-7.85 (m, 1H, CH$_{Ar}$), 7.61-7.59 (m, 1H, CH$_{Ar}$), 7.57-7.54 (m, 1H, CH$_{Ar}$), 7.45-7.41 (m, 4H, 4×CH$_{Ar}$), 7.36-7.33 (m, 7H, 7×CH$_{Ar}$), 7.32-7.27 (m, 5H, 5×CH$_{Ar}$), 5.53 (s, 1H, H-7C), 5.52 (s, 1H, H-7A), 5.35 (dd, J$_{2-3}$=3.5 Hz, J$_{2-4}$=1.6 Hz, 1H, H-2B), 5.21-5.19 (m, 2H, H-1B, H-2C), 5.02 (d, J=3.1 Hz, 1H, H-2D), 4.96 (d, J=3.9 Hz, 1H, H-4D), 4.91-4.82 (m, 5H, CH$_{2AZMB}$, CHH$_{Bn}$, H-4B, H-1D), 4.78-4.76 (m, 2H, CHH$_{Bn}$, H-1C), 4.49 (d, J=7.7 Hz, 1H, H-1A), 4.38 (dd, J$_{6a-6b}$=10.7 Hz, J$_{6a-6}$=5.0 Hz, 1H, H-6aC), 4.35 (dd, J$_{6a-6b}$=11.1 Hz, J$_{6a-5}$=5.6 Hz, 1H, H-6aA), 4.17 (q, J=6.5 Hz, 1H, H-5D), 4.10-4.04 (m, 3H, H-3B, H-3C, H-5B), 3.94-3.90 (m, 2H, H-1a$_{linker}$, H-3A), 3.79-3.75 (m, 2H, H-6bA, H-6bC), 3.67 (t, J=9.4 Hz, 1H, H-4C), 3.59-3.52 (m, 3H, H-1b$_{linker}$, H-5C, H-4A), 3.50-3.45 (m, 2H, H-2A, H-3D), 3.41 (td, J$_{5-4}$=9.7 Hz, J$_{5-6}$=5.0 Hz, H-5A), 3.24 (s, 3H, CH$_{3OMe}$), 3.22 (t, J=6.9 Hz, 2H, H-5$_{linker}$), 2.36-2.30 (m, 1H, CHH$_{Lev}$), 2.17-2.10 (m, 2H, CHH$_{Lev}$, CHH$_{Lev}$), 2.08 (s, 3H, CH$_{3Ac}$), 2.05 (s, 3H, CH$_{3 Lev}$), 2.04 (s, 3H, CH$_{3Ac}$), 1.81-1.77 (m, 1H, CHH$_{Lev}$), 1.77 (s, 3H, CH$_{3Ac}$), 1.67-1.64 (m, 2H, H-2$_{linker}$) 1.60-1.59 (m, 2H, H-4$_{linker}$), 1.49-1.41 (m, 2H, H-3$_{linker}$), 0.76 (d, J=6.2 Hz, 3H, H-6B), 0.70 (d, J=6.5 Hz, 3H, H-6D); $^{13}$C NMR (150 MHz, CDCl3) δ (ppm) 206.2 (CO$_{Lev}$), 171.4 (COOR$_{Lev}$), 170.8 (COOR$_{Ac}$), 170.0 (COOR$_{Ac}$), 169.5 (COOR$_{Ac}$), 164.2 (COOR$_{AZMB}$), 138.7 (C$_{Ar}$), 138.0 (C$_{Ar}$), 137.14 (C$_{Ar}$), 137.07 (C$_{Ar}$), 133.1-126.2 (20C, C$_{Ar}$, 19×CH$_{Ar}$), 104.2 (C-1A), 102.1, 101.7 (2C, C-7A, C-7C), 100.9 (C-1C), 99.1 (C-1D), 97.8 (C-1B), 82.7 (C-2A), 79.3 (C-4A), 79.0 (C-4C), 76.2, 76.1 (2C, C-3A, C-3C), 75.0, 74.9 (2C, C-3B, CH$_{2Bn}$), 74.6 (C-2C), 73.4 (C-3D), 72.6 (C-4B), 70.9 (C-2B), 70.3 (C-1$_{linker}$), 68.9, 68.7, 68.5 (3C, C-6A, C-6C, C-2D), 66.5, 66.3, 66.2 (4C, C-5A, C-5B, C-5C, C-4D), 65.5 (C-5D), 57.2 (CH$_{3OMe}$), 53.1 (CH$_{2AZMB}$), 51.4 (C-5$_{linker}$), 37.5 (CH$_{2Lev}$), 29.8 (CH$_{3Lev}$), 29.4 (C-2$_{linker}$), 28.8 (C-4$_{linker}$), 27.5 (CH$_{2Lev}$), 23.5 (C-3$_{linker}$), 21.1 (CH$_{3Ac}$), 21.0 (CH$_{3Ac}$), 20.8 (CH$_{3Ac}$), 16.8 (C-6B), 15.8 (C-6D); HRMS (ESI-TOF) m/z [M+NH$_4$]$^+$ calcd for C$_{70}$H$_{88}$N$_7$O$_{25}$ 1426.58244; found 1426.58819; m/z [M+Na]$^+$ calcd for C$_{70}$H$_{84}$N$_6$NaO$_{25}$ 1431.53873; found 1431.54367.

(5-Azido-1-pentyl) 2-O-acetyl-4-O-chloroacetyl-6-deoxy-3-O-methyl-α-L-talopyranosyl-(1→3)-2-O-ortho-(azidomethyl)benzoyl-4,6-O-benzylidene-β-D-glucopyranosyl-(1→3)-2-O-acetyl-4-O-levulinoyl-α-L-rhamnopyranosyl-(1→3)-2-O-benzyl-4,6-O-benzylidene-β-D-glucopyranoside (37)

Trisaccharide 29 (109 mg, 0.0933 mmol, 1.0 equiv), thiotaloside 35 (56 mg, 0.14 mmol, 1.5 equiv), and NIS (32 mg, 0.14 mmol, 1.5 equiv) were dried together under high vacuum for 1 h. 4 Å activated ground molecular sieves (435 mg) and anhydrous DCM (1.9 mL) were successively added and the mixture was stirred under Ar for 1 h. The reaction flask was cooled to −10° C. and protected from light using aluminum foil. AgOTf (2 mg, 0.009 mmol, 0.1 equiv) was added and the mixture was stirred under Ar for 2 h while being gradually warmed to 0° C. Et$_3$N (0.01 mL, 0.09 mmol, 1.0 equiv) was added, the yellow suspension was filtered over Celite, and the solvents were evaporated under reduced pressure. The residue was purified by silica gel flash chromatography (Hex/EtOAc 8:2 to 5:5) to give tetrasaccharide 37 (110 mg, 82%) as a white amorphous solid: R$_f$ 0.4 (Tol/EtOAc 7:3); [α]$_D^{20}$ −68 (c 0.6, CHCl$_3$); $^1$H NMR (600 MHz, CDCl$_3$) δ (ppm) 7.86 (m, 1H, CH$_{AZMB}$), 7.61-7.59 (m, 1H, CH$_{Ar}$), 7.57-7.55 (m, 1H, CH$_{Ar}$), 7.45-7.44 (m, 2H, 2×CH$_{Ar}$), 7.42-7.41 (m, 2H, 2×CH$_{Ar}$), 7.37-7.33 (m, 7H, 7×CH$_{Ar}$), 7.31-7.28 (m, 5H, 5×CH$_{Ar}$), 5.53 (s, 1H, H-7C), 5.52 (s, 1H, H-7A), 5.35 (dd, J$_{2-3}$=3.5 Hz, J$_{2-1}$=1.7 Hz, 1H, H-2B), 5.21-5.18 (m, 2H, H-1B, H-2C), 5.07 (d, J=3.3 Hz, 1H, H-2D), 4.94 (d, J=3.9 Hz, 1H, H-4D), 4.90-4.81 (m, 5H, CH$_{2AZMB}$, CHH$_{Bn}$, H-1D, H-4B), 4.78-4.76 (m, 2H, CHH$_{Bn}$, H-1C), 4.49 (d, J=7.7 Hz, 1H, H-1A), 4.38 (dd, J$_{6a-6b}$=10.6 Hz, J$_{6a-5}$=4.9 Hz, 1H, H-6aC), 4.35 (dd, J$_{6a-6b}$=10.4 Hz, J$_{6a-5}$=4.9 Hz, 1H, H-6aA), 4.22-4.18 (m, 1H, H-5D), 4.10-4.00 (m, 5H, CH$_{2AcCl}$, H-3B, H-5B, H-3C), 3.94-3.90 (m, 2H, H-1a$_{linker}$, H-3A), 3.77 (td, J=10.3 Hz, J=4.9 Hz, 2H, H-6bA, H-6bC), 3.67 (t, J=9.4 Hz, 1H, H-4C), 3.59-3.52 (m, 3H, H-1b$_{linker}$, H-5C, H-4A), 3.49-3.47 (m, 2H, H-2A, H-3D), 3.41 (td, J$_{5-4}$=9.8 Hz, J$_{5-6}$=5.0 Hz, 1H, H-5A), 3.24 (s, 3H, CH$_{3OMe}$), 3.22 (t, J=6.9 Hz, 2H, H-5) 2.36-2.30 (m, 1H, CHH$_{Lev}$), 2.14-2.07 (m, 2H, CHH$_{Lev}$, CHH$_{Lev}$), 2.07 (s, 3H, CH$_{3Ac}$), 2.05 (s, 3H, CH$_{3Lev}$), 1.82-1.80 (m, 1H, CHH$_{Lev}$), 1.77 (s, 3H, CH$_{3Ac}$), 1.69-1.63 (m, 2H, H-2$_{linker}$), 1.61-1.60 (m, 2H, H-4$_{linker}$), 1.48-1.42 (m, 2H, H3$_{linker}$), 0.76 (d, J=6.2 Hz, 3H, H-6B), 0.70 (d, J=6.5 Hz, 3H, H-6D); $^{13}$C NMR (150 MHz, CDCl$_3$) δ (ppm) 206.2 (CO$_{Lev}$), 171.4 (COOR$_{Lev}$), 170.0 (COOR$_{Ac}$), 169.4 (COOR$_{Ac}$), 167.3 (COOR$_{AcCl}$), 164.2 (COOR$_{AZMB}$), 139.7 (C$_{Ar}$), 138.0 (C$_{Ar}$), 137.2 (2C, 2×C$_{Ar}$), 137.1-126.2 (20C, C$_{Ar}$, 19×CH$_{Ar}$), 104.3 (C-1A), 102.2, 101.7 (2C, C-7A, C-7C), 100.9 (C-1C), 99.0 (C-1D), 97.8 (C-1B), 82.7 (C-2A), 79.3 (C-4A), 79.0 (C-4C), 76.4, 76.1 (2C, C-3A, C-3C), 75.0, 74.9 (2C, C-3B, CH$_{2Bn}$), 74.6 (C-2C), 73.1 (C-3D), 72.6 (C-4B), 71.0 (C-2B), 70.6 (C-2D), 70.3 (C-1$_{linker}$), 68.9, 68.7 (2C, C-6A, C-6C), 66.5, 66.3, 66.2, 66.1 (4C, C-5A, C-5B, C-5C, C-4D), 65.2 (C-5D), 57.3 (CH$_{3OMe}$), 53.1 (CH$_{2AZMB}$), 51.4 (C-5$_{linker}$), 40.9 (CH$_{2AcCl}$), 37.5 (CH$_{2Lev}$), 29.8 (CH$_{3Lev}$), 29.5 (C-2$_{linker}$), 28.8 (C-4$_{linker}$), 27.5 (CH$_{2Lev}$), 23.5 (C-3$_{linker}$), 21.0 (CH$_{3Ac}$), 20.8 (CH$_{3Ac}$), 16.8 (C-6B), 15.7 (C-6D); HRMS (ESI-TOF) m/z [M+NH$_4$]$^+$ calcd for C$_{70}$H$_{87}$ClN$_7$O$_{25}$ 1460.54347; found 146054641.

(5-Azido-1-pentyl) 2,4-O-di-acetyl-6-deoxy-3-O-methyl-α-L-talopyranosyl-(1→3)-2-O-ortho-(azidomethyl)benzoyl-4,6-O-benzylidene-β-D-glucopyranosyl-(1→3)-2-O-acetyl-α-L-rhamnopyranosyl-(1→3)-2-O-benzyl-4,6-O-benzylidene-β-D-glucopyranoside (38)

A solution of tetrasaccharide 36 (98 mg, 0.070 mmol, 1.0 equiv) in anhydrous pyridine (0.45 mL) was cooled at 0° C. Acetic acid (0.3 mL) and hydrazine monohydrate (0.02 mL, 0.4 mmol, 5.0 equiv) were successively slowly added. The mixture was stirred for 16 h under Ar while gradually being warmed to rt. The solution was concentrated under reduced pressure and co-evaporated with toluene (3×). The residue was purified by silica gel flash chromatography (Tol/EtOAc 9:1 to 7:3) to give alcohol 38 (78 mg, 85%) as a white amorphous solid: R$_f$ 0.5 (Tol/EtOAc 6:4); [α]$_D^{20}$ −59 (c 0.8, CHCl$_3$); $^1$H NMR (600 MHz, CDCl$_3$) α (ppm) 7.95 (m, 1H, CH$_{AZMB}$), 7.55-7.50 (m, 2H, 2×CH$_{Ar}$), 7.45-7.43 (m, 2H, 2×CH$_{Ar}$), 7.39-7.27 (m, 12H, 12×CH$_{Ar}$), 7.24-7.22 (m, 2H, 2×CH$_{Ar}$), 5.52 (s, 1H, H-7C), 5.48 (s, 1H, H-7A), 5.31-5.27 (m, 2H, H-2B, H-2C), 5.14 (s, 1H, H-1B), 5.03 (d, J=3.1 Hz, 1H, H-2D), 4.98 (d, J=3.9 Hz, 1H, H-4D), 4.94 (d, J=14.9 Hz, 1H, CHH$_{AZMB}$), 4.91 (s, 1H, H-1D), 4.87-4.82 (m, 2H, CHH$_{Bn}$, H-1C), 4.79-4.77 (m, 2H, CHH$_{Bn}$, CHH$_{AZMB}$), 4.48 (d, J=7.7 Hz, 1H, H-1A), 4.36 (dd, J$_{6a-6b}$=10.6 Hz, J$_{6a-5}$=4.9 Hz, 1H, H-6aC), 4.34 (dd, J$_{6a-6b}$=10.4 Hz, J$_{6a-5}$=4.9 Hz, 1H, H-6aA), 4.18 (q, J=6.5 Hz, 1H, H-5D), 4.08 (t, J=9.2 Hz, 1H, H-3C), 3.96-3.89 (m, 3H, H-1a$_{linker}$, H-5B, H-3A), 3.85 (dd, J$_{3-4}$=9.4 Hz, J$_{3-2}$=3.6 Hz, 1H, H-3B), 3.77-3.72 (m, 2H, H-6bA, H-6bC), 3.66 (t, J=9.4 Hz, 1H, H-4C), 3.56-3.52 (m, 2H, H-1b$_{linker}$, H-4A), 3.52-3.50 (m, 1H, H-5C), 3.48-3.44 (m, 3H, H-3D, H-2A, H-4B), 3.41-3.37 (m, 1H, H-5A), 3.26 (s, 3H, CH$_{3OMe}$), 3.20 (t, J=6.9 Hz, 2H, H-5$_{linker}$), 2.05 (s, 3H, CH$_{3Ac}$), 2.04 (s, 3H, CH$_{3Ac}$), 1.76 (s, 3H, CH$_{3Ac}$), 1.66-1.63 (m, 2H, H-2$_{linker}$), 1.60-1.56 (m, 2H, H-4$_{linker}$), 1.46-1.40 (m, 2H, H-3) 0.85 (d, J=6.2 Hz, 3H, H-6B), 0.72 (d, J=6.5 Hz, 3H, H-6D); $^{13}$C NMR (150 MHz, CDCl$_3$) δ (ppm) 170.8 (COOR$_{Ac}$), 169.9 (COOR$_{Ac}$), 169.6 (COOR$_{Ac}$), 165.0 (COOR$_{AZMB}$), 139.0 (C$_{Ar}$), 138.2 (C$_{Ar}$), 137.1 (2C, 2×C$_{Ar}$), 133.4-126.2 (20C, C$_{Ar}$, 19×CH$_{Ar}$), 104.2 (C-1A), 102.1 (C-7C), 101.5 (2C, C-7A, C-1C), 99.0 (C-1D), 98.1 (C-1B), 82.8 (C-2A), 79.3, 79.1, 78.9 (3C, C-4A, C-4C, C-3B), 76.5 (C-3A), 75.9 (C-3C), 75.1, 75.0 (2C, C-2C, CH$_{2Bn}$), 73.4 (C-3D), 71.7 (C-4), 70.5 (C-2B), 70.2 (C-1$_{linker}$), 68.9 (3C, C-6A, C-6C, C-2D), 67.8 (C-5B), 66.6, 66.4 (3C, C-4D, C-5A, C-5C), 65.5 (C-5D), 57.2 (CH$_{3OMe}$), 53.4 (CH$_{2AZMB}$), 51.4 (C-5$_{linker}$), 29.4 (C-2$_{linker}$), 28.7 (C-4$_{linker}$), 23.5 (C-3$_{linker}$), 21.1 (CH$_{3Ac}$), 21.0 (CH$_{3Ac}$), 20.8 (CH$_{3Ac}$), 17.1 (C-6B), 15.8 (C-6D); HRMS (ESI-TOF) m/z [M+NH$_4$]$^+$ calcd for C$_{65}$H$_{82}$N$_7$O$_{23}$ 1328.54566; found 1328.5449; m/z [M+Na]$^+$ calcd for C$_{65}$H$_{78}$N$_6$NaO$_{23}$ 1333.50105; found 1333.50103.

(5-Azido-1-pentyl) 2-O-acetyl-4-O-chloroacetyl-6-deoxy-3-O-methyl-α-L-talopyranosyl-(1→3)-2-O-ortho-(azidomethyl)benzoyl-4,6-O-benzylidene-β-D-glucopyranosyl-(1→3)-2-O-acetyl-α-L-rhamnopyranosyl-(1→3)-2-O-benzyl-4,6-O-benzylidene-β-D-glucopyranoside (39)

A solution of tetrasaccharide 37 (476 mg, 0.330 mmol, 1.0 equiv) in anhydrous pyridine (2 mL) was cooled at 0° C. Acetic acid (1.4 mL) and hydrazine monohydrate (0.08 mL, 2 mmol, 5.0 equiv) were successively slowly added. The mixture was stirred for 3 h under Ar while gradually being warmed to rt. The solution was concentrated under reduced pressure and co-evaporated with toluene (3×). The residue was purified by silica gel flash chromatography (Tol/EtOAc 9:1 to 7:3) to give alcohol 39 (290 mg, 65%) as a white amorphous solid: R$_f$ 0.7 (Tol/EtOAc 7:3); [α]$_D^{20}$−52 (c 0.6, CHCl$_3$); $^1$H NMR (600 MHz, CDCl$_3$) α (ppm) 7.95-7.93 (m, 1H, CH$_{AZMB}$), 7.55-7.51 (m, 2H, 2×CH$_{Ar}$), 7.45-7.43 (m, 2H, 2×CH$_{Ar}$), 7.39-7.27 (m, 12H, 12×CH$_{Ar}$), 7.24-7.22 (m, 2H, 2'CH$_{Ar}$), 5.52 (s, 1H, H-7C), 5.49 (s, 1H, H-7A), 5.31 (dd, J$_{2-3}$=3.5 Hz, J$_{2-1}$=1.6 Hz, 1H, H-2B), 5.28 (dd, J=8.8 Hz, J=7.8 Hz, 1H, H-2C), 5.14 (d, J=1.2 Hz, 1H, H-1B), 5.08 (s, 1H, H-2D), 4.97 (d, J=3.9 Hz, 1H, H-4D), 4.94 (d, J=14.9 Hz, 1H, CHH$_{AZMB}$), 4.90 (s, 1H, H-1D), 4.86 (d, J=10.7 Hz, 1H, CHH$_{Bn}$), 4.83 (d, J=7.7 Hz, 1H, H-1C), 4.79-4.76 (m, 2H, CHH$_{AZMB}$, CHH$_{Bn}$), 4.48 (d, J=7.7 Hz, 1H, H-1A), 4.36 (dd, J$_{6a-6b}$=10.8 Hz, J$_{6a-5}$=5.1 Hz, 1H, H-6aC), 4.34 (dd, H$_{6a-6b}$=10.6 Hz, J$_{6a-5}$=5.1 Hz, 1H, H-6aA), 4.20 (q, J=6.6 Hz, 1H, H-5D), 4.08-4.00 (m, 3H, CH$_{2AcCl}$, H-3C), 3.95-3.84 (m, 3H, H-1a$_{linker}$, H-5B, H-3A), 3.85 (dd, J=9.4 Hz, 42=3.6 Hz, 1H, H-3B), 3.76 (d, J=10.4 Hz, 1H, H-6bA) 3.73 (d, J=10.5 Hz, 1H, H-6bC), 3.67 (t, J=9.4 Hz, 1H, H-4C), 3.56-3.50 (m, 4H, H-1b$_{linker}$, H-3D, H-4A, H-5C), 3.48-3.41 (m, 2H, H-2A, H-4B), 3.39 (td, J=9.7 Hz, J=5.0 Hz, 1H, H-5A), 3.26 (s, 3H, CH$_{3OMe}$), 3.20 (t, J=6.9 Hz, 2H, H-2$_{linker}$), 2.08 (s, 1H, OH), 2.03 (s, 3H, CH$_{3Ac}$), 1.76 (s, 3H, CH$_{3Ac}$), 1.66-1.62 (m, 2H, H-2$_{linker}$), 1.61-1.56 (m, 2H, H-4$_{linker}$), 1.47-1.40 (m, 2H, H-3$_{linker}$), 0.85 (d, J=6.2 Hz, 3H, H-6B), 0.72 (d, J=6.2 Hz, 3H, H-6D); $^{13}$C NMR (150 MHz, CDCl$_3$) δ (ppm) 169.9 (COOR$_{Ac}$), 169.5 (COOR$_{Ac}$), 167.3 (COOR$_{AcCl}$), 165.0 (COOR$_{AZMB}$), 139.0 (C$_{Ar}$), 138.2 (C$_{Ar}$), 137.1 (C$_{Ar}$), 137.0 (C$_{Ar}$), 133.4-126.2 (20C, C$_{Ar}$, 19×CH$_{Ar}$), 104.2 (C-1A), 102.2, 101.59. 101.56 (3C, C-1C, C-7A, C-7C), 98.9 (C-1D), 98.1 (C-1B), 82.8 (C-2A), 79.4, 79.1, 78.9 (3C, C-4A, C-4C, C-3B), 76.5 (C-3A), 76.1 (C-3C), 75.1, 75.0 (2C, CH$_{2Bn}$, C-2C), 73.1 (C-3D), 71.8 (C-4B), 70.6, 70.5 (2C, C-2B, C-2D), 70.2 (C-1$_{linker}$), 68.9, 68.7 (2C, C-6A, C-6C), 67.8 (C-5B), 66.5 (C-5A), 66.4 (C-5C), 66.2 (C-4D), 65.2 (C-5D), 57.3 (CH$_{3OMe}$), 53.4 (CH$_{2AZMB}$), 51.4 (C-5$_{linker}$), 40.9 (CH$_{2AcCl}$), 29.4 (C-2$_{linker}$), 28.8 (C-4$_{linker}$), 23.5 (C-3$_{linker}$), 21.1 (CH$_{3Ac}$), 20.8 (CH$_{3Ac}$), 17.1 (C-6B), 15.8 (C-6D); HRMS (ESI-TOF) m/z [M+NH$_4$]$^+$ calcd for C$_{65}$H$_{81}$N$_7$O$_{23}$ 1362.50669; found 1362.51071; m/z [M+Na]$^+$ calcd for C$_{65}$H$_{77}$ClN$_6$NaO$_{23}$ 1367.46208; found 1367.46835.

(5-Azido-1-pentyl) 2,4-O-di-acetyl-6-deoxy-3-O-methyl-α-L-talopyranosyl-(1→3)-2-O-ortho-(azidomethyl)benzoyl-4,6-O-benzylidene-β-D-glucopyranosyl-(1→3)-2-O-acetyl-6-deoxy-α-L-talopyranosyl-(1→3)-2-O-benzyl-4,6-O-benzylidene-β-D-glucopyranoside (40)

Dess-Martin periodinane (10 mg, 0.023 mmol, 2.2 equiv) was added to a solution of alcohol 38 (14 mg, 0.011 mmol, 1.0 equiv) in anhydrous DCE (0.16 mL). The mixture was refluxed under Ar for 1 h, then cooled to rt. The solution was diluted with DCM (1 mL) and quenched with 10% Na$_2$S$_2$O$_3$ (aq) (1 mL). The solution was transferred into a separatory funnel and the organic and aqueous layers were separated. The organic phase was washed with brine (1 mL), dried over anhydrous MgSO$_4$, and concentrated under reduced pressure. The residue was purified by silica gel flash chromatography (Hex/EtOAc 9:1 to 6:4) to give the corresponding ketone as a white solid. The latter was dissolved in anhydrous DCM/MeOH (0.2 mL, 1:3) and the solution was cooled at 10° C. NaBH$_4$ (2 mg, 0.04 mmol, 4.0 equiv) was slowly added and the mixture was stirred under Ar for 1 h while gradually being warmed to 0° C. The solution was diluted with DCM (1 mL) and washed with water (1 mL). The aqueous layer was extracted with DCM (3×1 mL). The combined organic layers were washed with brine (4 mL), dried over anhydrous MgSO$_4$, and concentrated under reduced pressure. The residue was purified by silica gel flash chromatography (Tol/EtOAc 9:1 to 7:3) to give alcohol 40 (7 mg, 52%) as a white amorphous solid: R$_f$ 0.3 (Tol/EtOAc 7:3); [α]$_D^{20}$−96 (c 0.1, CHCl$_3$); $^1$H NMR (600 MHz, CDCl$_3$) δ (ppm) 8.02-8.01 (m, 1H, CH$_{AZMB}$), 7.58-7.54 (m, 2H, 2×CH$_{Ar}$), 7.47-7.44 (m, 4H, 4×CH$_{Ar}$), 7.39-7.36 (m, 6H, 6×CH$_{Ar}$), 7.33-7.30 (m, 5H, 5×CH$_{Ar}$), 7.28-7.26 (m, 1H, CH$_{Ar}$), 5.56 (s, 1H, H-7C), 5.52 (s, 1H, H-7A), 5.33 (dd, J$_{2-3}$=8.9 Hz, J$_{2-1}$=7.9 Hz, 1H, H-2C), 5.26-5.23 (m, 1H, H-2B), 5.22 (s, 1H, H-1B), 5.05 (d, J=3.1 Hz, 1H, H-2D), 5.01 (d, J=3.9 Hz, 1H, H-4D), 4.95 (d, J=7.7 Hz, 1H, H-1C), 4.91-4.87 (m, 4H, CH$_{2AZMB}$, CHH$_{Bn}$, H-1D), 4.73 (d, J=10.8 Hz, 1H, CHH$_{Bn}$), 4.51 (d, J=7.8 Hz, 1H, H-1A), 4.38 (dd, J$_{6a-6b}$=10.8 Hz, J$_{6a-5}$=5.1 Hz, 1H, H-6aC), 4.35 (dd, J$_{6a-6b}$=11.0 Hz, J$_{6a-5}$=5.4 Hz, 1H, H-6aA), 4.20 (q, J=5.4 Hz, 1H, H-5D), 4.14-4.11 (m, 2H, H-5B, H-3C), 4.10 (t, J=3.6 Hz, 1H, H-3B), 3.96 (t, J=8.2 Hz, 1H, H-3A), 3.94-3.91 (m, 1H, H-1a$_{linker}$), 3.82-3.77 (m, 2H, H-6bA, H-6bC), 3.71 (t, J=9.4 Hz, 1H, H-4C), 3.60-3.54 (m, 4H, H-1b$_{linker}$, H-4A, H-4B, H-5C), 3.51 (t, J=3.7 Hz, 1H, H-3D), 3.47-3.41 (m, 2H, H-2A, H-5A), 3.30 (s, 3H, CH$_{3OMe}$), 3.22 (t, J=6.9 Hz, 2H, H-5$_{linker}$), 2.26 (d, J=9.7 Hz, 1H, OH), 2.07 (s, 3H, CH$_{3Ac}$), 1.79 (s, 3H, CH$_{3Ac}$), 1.68-1.63 (m, 2H, H-2$_{linker}$), 1.63 (s, 3H, CH$_{3Ac}$), 1.62-1.60 (m, 2H, H-4$_{linker}$), 1.48-1.42 (m, 2H, H-3$_{linker}$), 0.95 (d, J=6.5 Hz, 3H, H-6B), 0.74 (d, J=6.5 Hz, 3H, H-6D); $^{13}$C NMR (150 MHz, CDCl$_3$) δ (ppm) 170.9 (COOR$_{Ac}$), 169.6 (COOR$_{Ac}$), 168.8 (COOR$_{Ac}$), 164.5 (COOR$_{AZMB}$), 139.4 (C$_{Ar}$), 138.2 (C$_{Ar}$), 137.4 (C$_{Ar}$), 137.0 (C$_{Ar}$), 133.2-126.28 (20C, C$_{Ar}$, 19×CH$_{Ar}$), 104.3 (C-1A), 102.2, 101.8 (2C, C-7A, C-7C), 99.0 (C-1D), 98.4 (C-1B), 97.2 (C-1C), 83.1 (C-2A), 79.23, 79.16 (2C, C-4A, C-4C), 76.1 (C-3A), 75.7 (C-3C), 74.9 (CH$_{2Bn}$), 74.5 (C-2C), 73.4 (C-3D), 70.4 (C-3B), 70.3 (C-1$_{linker}$), 69.4, 69.0, 68.8, 68.5, 68.0 (5C, C-2B, C-2D, C-6A, C-6C, C-4B), 66.9, 66.41, 66.39, 66.37 (4C, C-5A, C-5B, C-5C, C-4D), 65.4 (C-5D), 57.2 (CH$_{3OMe}$), 53.1 (CH$_{2AZMB}$), 51.4 (C-5) 29.4 (C-2$_{linker}$), 28.7 (C-4$_{linker}$), 23.5 (C-3$_{linker}$), 21.0 (CH$_{3Ac}$), 20.8 (CH$_{3Ac}$), 20.3 (CH$_{3Ac}$), 16.1 (C-6B), 15.9 (C-6D); HRMS (ESI-TOF) m/z [M+NH$_4$]$^+$ calcd for C$_{65}$H$_{82}$N$_7$O$_{23}$ 1328.54566; found 1328.54556; m/z [M+Na]$^+$ calcd for C$_{65}$H$_{78}$N$_6$NaO$_{23}$ 1333.50105; found 1333.50256.

(5-Azido-1-pentyl) 2-O-acetyl-6-deoxy-3-O-methyl-α-L-talopyranosyl-(1→3)-2-O-ortho-(azidomethyl)benzoyl-4,6-O-benzylidene-β-D-glucopyranosyl-(1→3)-2-O-acetyl-6-deoxy-α-L-talopyranosyl-(1→3)-2-O-benzyl-4,6-O-benzylidene-β-D-glucopyranoside (31)

A solution of anhydrous DMSO (0.06 mL, 0.8 mmol, 10.0 equiv) in anhydrous DCM (1.4 mL) was cooled at −10° C.

and PDCP (0.07 mL, 0.5 mmol, 6.0 equiv) and Et$_3$N (0.11 mL, 0.80 mmol, 10.0 equiv) were successively added. A solution of alcohol 39 (108 mg, 0.0803 mmol, 1.0 equiv) in anhydrous DCM (0.4 mL) was added dropwise for 30 min. The mixture was stirred at −10° C. for 10 min under Ar, and for an additional 30 min while gradually being warmed to rt. Water (5 mL) was added to the solution, which was then transferred into a separatory funnel. The organic and aqueous layers were separated, and the aqueous phase was extracted with DCM (3×5 mL). The combined organic layers were washed with brine (10 mL), then dried over anhydrous MgSO$_4$, and concentrated under reduced pressure. The residue was purified by silica gel flash chromatography (Tol/EtOAc 9:1 to 8:2) to give the ketone as a white amorphous solid. The latter was solubilized in MeOH (1.1 mL) and DCM (0.4 mL) and cooled to −10° C. NaBH$_4$ (12 mg, 0.32 mmol, 4.0 equiv) was slowly added and the mixture was stirred 1 h while gradually being warmed to 0° C. The solution was diluted with DCM (5 mL), transferred in a separatory funnel, and washed with water (5 mL). The aqueous phase was extracted with DCM (3×5 mL), the combined organic phases were washed with brine (10 mL) and dried over anhydrous MgSO$_4$. The solution was concentrated under reduced pressure. The resulting crude alcohol (80.8 mg) was dissolved in anhydrous MeOH (2.3 mL) and anhydrous pyridine (2.3 mL). Thiourea (183 mg, 2.40 mmol) was added and the solution was stirred under Ar for 3 h at 60° C. The solvents were concentrated under reduced pressure and co-evaporated with toluene. The resulting white solid was dissolved in a 2:1 mixture of DCM/MeOH (10 mL) and washed with HCl 1N (10 mL). The aqueous phase was extracted with DCM (3×10 mL) and the combined organic layers were washed with saturated NaHCO$_3$ (aq) (30 mL) and brine (30 mL). The organic phase was dried over anhydrous MgSO$_4$ and concentrated under reduced pressure. The residue was purified by silica gel flash chromatography (Tol/EtOAc 9:1 to 7:3) to give alcohol 31 (58.9 mg, 58% over 3 steps) as a white amorphous solid: R$_f$ 0.5 (Tol/EtOAc 1:1); [α]$_D^{20}$ −79 (c 0.9, CHCl$_3$); $^1$H NMR (600 MHz, CDCl$_3$) δ (ppm) 8.01 (m, 1H, CH$_{AZMB}$), 7.56-7.52 (m, 2H, 2×CH$_{Ar}$), 7.47-7.45 (m, 2H, 2×CH$_{Ar}$), 7.43 (m, 2H, 2×CH$_{Ar}$), 7.37-7.28 (m, 11H, 11×CH$_{Ar}$), 7.25-7.22 (m, 1H, CH$_{Ar}$), 5.54 (s, 1H, H-7C), 5.50 (s, 1H, H-7A), 5.30 (dd, J$_{2-3}$=9.0 Hz, J$_{2-1}$=7.8 Hz, 1H, H-2C), 5.22 (d, J=3.8 Hz, 1H, H-2B), 5.20 (s, 1H, H-1B), 5.02 (d, J=3.7 Hz, 1H, H-2D), 4.92 (d, J=7.8 Hz, 1H, H-1C), 4.88-4.85 (m, 4H, CHH$_{Bn}$, CH$_{2AZMB}$, H-1D), 4.71 (d, J=10.8 Hz, 1H, CHH$_{Bn}$), 4.48 (d, J=7.8 Hz, 1H, H-1A), 4.36 (dd, J$_{6a-6b}$=10.6 Hz, J$_{6a-5}$=4.9 Hz, 1H, H-6aC), 4.33 (dd, J$_{6a-6b}$=10.6 Hz, J$_{6a-5}$=5.0 Hz, 1H, H-6aA), 4.13 (t, J=9.2 Hz, 1H, H-3C), 4.11-4.05 (m, 3H, H-3B, H-5B, H-5D), 3.94 (t, J=9.2 Hz, 1H, H-3A), 3.91-3.89 (m, 1H, H-1a$_{linker}$), 3.80-3.74 (m, 2H, H-6bA, H-6bC), 3.68 (t, J=9.4 Hz, 1H, H-4C), 3.58-3.50 (m, 5H, H-1b$_{linker}$, H-5C, H-4B, H-4D, H-4A), 3.45-3.39 (m, 3H, H-5A, H-2A, H-3D), 3.32 (s, 3H, CH$_{3OMe}$), 3.19 (t, J=6.9 Hz, 2H, H-5$_{linker}$), 2.22 (d, J=9.8 Hz, 1H, OH), 2.20 (d, J=8.5 Hz, 1H, OH), 1.78 (s, 3H, CH$_{3Ac}$), 1.66-1.62 (m, 2H, H-2$_{linker}$), 1.60 (s, 3H, CH$_{3Ac}$), 1.59-1.56 (m, 2H, H-4$_{linker}$), 1.45-1.40 (m, 2H, H-3$_{linker}$), 0.93 (d, J=6.5 Hz, 3H, H-6B*), 0.90 (d, J=6.5 Hz, 3H, H-6D*); $^{13}$C NMR (150 MHz, CDCl$_3$) δ (ppm) 168.9 (COOR$_{Ac}$), 168.8 (COOR$_{Ac}$), 164.6 (COOR$_{AZMB}$), 139.3 (C$_{Ar}$), 138.1 (C$_{Ar}$), 137.3 (C$_{Ar}$), 137.0 (C$_{Ar}$), 133.2-126.3 (20C, C$_{Ar}$, 19×CH$_{Ar}$), 104.2 (C-1A), 102.1, 101.8 (2C, C-7A, C-7C), 98.6, 98.4 (2C, C-1B, C-1D), 97.2 (C-1C), 83.0 (C-2A), 79.2 (C-4A, C-4C), 76.1 (C-3A), 75.8 (C-3C), 74.9 (CH$_{2Bn}$), 74.5 (C-2C), 73.9 (C-3D), 70.4 (C-3B), 70.2 (C-1$_{linker}$), 69.34, 69.29, 68.9, 68.8 (4C, C-6A, C-6C, C-2B, C-4D), 68.0, 67.7, 67.2 (3C, C-4B, C-2D, C-5D), 66.8 (C-5C), 66.4 (2C, C-5A, C-5B), 56.3 (CH$_{3OMe}$), 53.1 (CH$_{2AZMB}$), 51.4 (C-5) 29.4 (C-2$_{linker}$), 28.7 (C-4$_{linker}$), 23.5 (C-3$_{linker}$), 20.7 (CH$_{3Ac}$), 20.3 (CH$_{3Ac}$), 16.1, 16.0 (2C, C-6B, C-6D); HRMS (ESI-TOF) m/z [M+NH$_4$]$^+$ calcd for C$_{63}$H$_{80}$N$_7$O$_{22}$ 1286.53509; found 1286.53314; m/z [M+Na]$^+$ calcd for C$_{63}$H$_{76}$N$_6$NaO$_{22}$ 1291.49049; found 1291; 48805.

(5-Azido-1-pentyl) 2-O-acetyl-4-O-levulinoyl-3-para-methoxybenzyl-α-L-rhamnopyranosyl-(1→3)-2-O-benzyl-4,6-O-benzylidene-β-D-glucopyranoside (41)

PPh$_3$ (3 mg, 0.01 mmol, 2.0 equiv) was added to a solution of disaccharide 26 (5 mg, 0.006 mmol, 1.0 equiv) in anhydrous THF (0.17 mL). The mixture was stirred at 60° C. under argon for 2 h, after which water (0.02 mL) was added. The solution was stirred for an additional 4 h at 60° C. and the solvents were evaporated under reduced pressure. The residue was purified by silica gel flash chromatography (DCM/MeOH 95:5 to 8:2) to give disaccharide 41 (4 mg, 88%) as a white amorphous solid; R$_f$ 0.5 (DCM/MeOH 8:2); [α]$_D^{20}$ −41 (c 0.4, CHCl$_3$); $^1$H NMR (600 MHz, CDCl$_3$) δ (ppm) 7.44-7.43 (m, 2H, 2×CH-Ar), 7.35-7.30 (m, 8H, 8×CH-Ar), 7.19 (m, 2H, 2×CH$_{PMB}$), 6.85 (m, 2H, 2×CH$_{PMB}$), 5.51 (s, 1H, H-7A), 5.43 (dd, J$_{2-3}$=3.2 Hz, J$_{2-4}$=1.7 Hz, 1H, H-2B), 5.17 (s, 1H, H-1B), 4.89-4.83 (m, 2H, H-4B, CHHPh), 4.69 (d, J=10.8 Hz, 1H, CHHPh), 4.58 (d, J=10.6 Hz, 1H, CHHPh), 4.49 (d, J=7.8 Hz, 1H, H-1A), 4.35 (dd, J$_{6a-6b}$=10.6 Hz, J$_{6a-5}$=5.0 Hz, 1H, H-6aA), 4.32 (d, J=11.6 Hz, 1H, CHHPh), 4.06 (dq, J$_{5-4}$=12.5 Hz, J$_{5-6}$=6.2 Hz, 1H, H-5B), 3.94-3.87 (m, 2H, H-1a$_{linker}$, H-3A), 3.80-3.78 (m, 1H, H-3B), 3.77 (s, 3H, CH$_{3PMB}$), 3.75 (m, 1H, H-6bA), 3.58-3.51 (m, 2H, H-1b$_{linker}$, H-4A), 3.45-3.39 (m, 2H, H-2A, H-5A), 2.80 (br s, 2H, H-5$_{linker}$), 2.71-2.66 (m, 1H, CHH$_{Lev}$), 2.62-2.57 (m, 1H, CHH$_{Lev}$), 2.48-2.38 (m, 2H, CH$_{2Lev}$), 2.14 (s, 3H, CH$_{3Lev}$), 2.05 (s, 3H, CH$_{3Ac}$), 1.69-1.64 (m, 4H, H-2$_{linker}$, H-4$_{linker}$), 1.45-1.41 (m, 2H, H-3$_{linker}$), 0.78 (d, J=6.2 Hz, 3H, H-6B). $^{13}$C NMR (600 MHz, CDCl$_3$) δ (ppm) 206.4 (CO$_{Lev}$), 172.0 (COOR$_{Lev}$), 170.2 (COOR$_{Ac}$), 159.3 (C-Ar), 137.9 (C-Ar), 137.2 (C-Ar), 130.4 (C-Ar), 129.5-126.3 (12C, 12×CH-Ar), 113.8 (2C, 2×CH$_{PMB}$), 104.3 (C-1A), 101.8 (C-7A), 98.4 (C-1B), 82.7 (C-2A), 79.3 (C-4A), 76.3 (C-3A), 75.0 (CH$_2$Ph), 74.6 (C-3B), 72.9 (C-4B), 71.1 (CH$_2$Ph), 70.2 (C-1$_{linker}$), 68.9 (C-6A), 68.5 (C-2B), 66.5 (2C, C-5A, C-5B), 55.4 (CH$_{3PMB}$), 40.5 (C-5$_{linker}$), 37.9 (CH$_{2Lev}$), 30.0 (CH$_3$Lev), 29.9 (C-2$_{linker}$), 29.5 (C-4$_{linker}$), 28.1 (CH$_{2Lev}$), 23.4 (C-3 21.1 (CH$_{3Ac}$), 17.0 (C-6B); HRMS (ESI-TOF) m/z [M+H]$^+$ calcd for C$_{46}$H$_{60}$NO$_{14}$ 850.40083; found 850.40044; m/z [M+Na]$^+$ calcd for C$_{46}$H$_{53}$NNaO$_{14}$ 872.38278; found 872.3821.

(5-Amino-1-pentyl) 4,6-O-benzylidene-3-O-para-methoxybenzyl-β-D-glucopyranosyl-(1→3)-2-O-acetyl-4-O-levulinoyl-α-L-rhamnopyranosyl-(1→3)-2-O-benzyl-4,6-O-benzylidene-β-d-glucopyranoside (42)

PPh$_3$ (8 mg, 0.03 mmol, 4.0 equiv) was added to a solution of trisaccharide 27 (10 mg, 0.0078 mmol, 1.0 equiv) in anhydrous THF (0.23 mL). The mixture was stirred at 60° C. under argon for 2 h, after which water (0.02 mL) was added. The solution was stirred for an additional 4 h at 60° C. and the solvents were evaporated under reduced pressure. The residue was purified by silica gel flash chromatography (DCM/MeOH 95:5 to 8:2) to give trisaccharide 42 (7 mg, 76%) as a white amorphous solid: $R_f$ 0.4 (DCM/MeOH 8:2); $[\alpha]_D^{20}$ −42 (c 0.5, CHCl$_3$); $^1$H NMR (600 MHz, CDCl$_3$) δ (ppm) 7.48-7.46 (m, 4H, 4×CH-Ar), 7.37-7.30 (m, 13H, 13×CH-Ar), 6.83-6.81 (m, 2H, 2×CH-Ar), 5.54 (s, 1H, H-7C), 5.52 (s, 1H, H-7A), 5.30 (distorted d, J=4.0 Hz, 1H, H-2B), 5.21 (s, 1H, H-1B), 4.97 (t, J=9.9 Hz, 1H, H-4B), 4.85-4.76 (m, 4H, CH$_{2Bn}$, CH$_{2PMB}$), 4.46 (d, J=7.7 Hz, 1H, H-1A), 4.41 (d, J=7.5 Hz, 1H, H-1C), 4.34 (dd, J$_{6a-6b}$=10.4 Hz, J$_{6a-5}$=4.7 Hz, 1H, H-6aC), 4.31 (dd, J$_{6a-6b}$=10.5 Hz, J$_{6a-5}$=4.9 Hz, 1H, H-6aA), 4.16 (dq, J$_{5-4}$=16.5 Hz, J$_{5-6}$=6.1 Hz, 1H, H-5B), 4.04 (dd, J$_{3-4}$=9.8 Hz, J$_{3-2}$=3.5 Hz, 1H, H-3B), 3.94-3.91 (m, 1H, H-3A), 3.88-3.85 (m, 1H, H-1a$_{linker}$), 3.80-3.75 (m, 4H, CH$_{3PMB}$, H-6bC), 3.70-3.66 (m, 1H, H-6bA), 3.59-3.51 (m, 5H, H-1b$_{linker}$, H-2C, H-3C, H-4C, H-4A), 3.49-3.46 (m, 1H, H-2A), 3.43-3.39 (m, 2H, H-5A, H-5C), 2.85-2.82 (m, 2H, H-5$_{linker}$), 2.81-2.78 (m, 1H, CHH$_{Lev}$), 2.65-2.53 (m, 2H, CHH$_{Lev}$, CHH$_{Lev}$), 2.38-2.34 (m, 1H, CHH$_{Lev}$), 2.18 (s, 3H, CH$_{3Lev}$), 2.04 (s, 3H, CH$_{3Ac}$), 1.70-1.68 (m, 2H, H-2$_{linker}$), 1.62-1.60 (m, 2H, H-4$_{linker}$), 1.40-1.36 (m, 2H, H-3) 0.82 (d, J=6.1 Hz, 3H, H-6B); $^{13}$C NMR (150 MHz, CDCl$_3$) δ (ppm) 207.7 (CO$_{Lev}$), 172.4 (COOR$_{Lev}$), 170.0 (COOR$_{Ac}$), 159.3 (C-Ar), 138.1 (C-Ar), 137.6 (C-Ar), 137.3 (C-Ar), 131.0-126.2 (18C, C-Ar, 17×CH-Ar), 113.8 (2C, 2×CH$_{PMB}$), 104.6, 104.2 (2C, C-1A, C-1C), 101.8, 101.3 (2C, C-7A, C-7C), 97.7 (C-1B), 82.7 (C-2A), 81.0, 79.3 (2C, C-4A, C-4C), 76.5, 76.0 (C-3A, C-301, 74.9 (2C, C-3B, CH$_{2Bn}$), 74.4, 74.3 (2C, CH$_{2PMB}$, C-201, 72.8 (C-4B), 71.4 (C-2B), 70.0 (C-1$_{linker}$), 68.9, 68.8 (2C, C-6A, C-6C), 66.44, 66.35, 65.9 (3C, C-5A, C-5B, C-5C), 55.4 (CH$_{3PMB}$), 39.9 (C-5$_{linker}$), 37.9 (CH$_{2Lev}$), 30.1 (CH$_{3Lev}$), 29.9 (C-2$_{linker}$), 29.2 (C-4$_{linker}$), 27.4 (CH$_{2Lev}$), 23.1 (C-3$_{linker}$), 21.2 (CH$_{3Ac}$), 16.9 (C-6B); HRMS (ESI-TOF) m/z [M+H]$^+$ calcd for C$_{59}$H$_{74}$NO$_{19}$ 1100.48496; found 1100.48469; m/z [M+Na]$^+$ calcd for C$_{53}$H$_{73}$NNaO$_{19}$ 1122.4669; found 1122.46659.

(5-Amino-1-pentyl) 2-O-acetyl-6-deoxy-3-O-methyl-α-L-talopyranosyl-(1→3)-4,6-O-benzylidene-β-D-glucopyranosyl-(1→3)-2-O-acetyl-6-deoxy-α-L-talopyranosyl-(1→3)-2-O-benzyl-4,6-O-benzylidene-β-D-glucopyranoside (43)

PPh$_3$ (4 mg, 0.02 mmol, 4.0 equiv) was added to a solution of tetrasaccharide 31 (5 mg, 0.004 mmol, 1.0 equiv) in anhydrous THF (0.12 mL). The mixture was stirred at 60° C. under argon for 2 h, after which water (0.02 mL) was added. The solution was stirred for an additional 4 h at 60° C., and the solvents were evaporated under reduced pressure. The residue was purified by silica gel flash chromatography (DCM/MeOH 95:5 to 8:2) to give disaccharide 43 (2.8 mg, 70%) as a white amorphous solid: $R_f$ 0.5 (DCM/MeOH 8:2); $[\alpha]_D^{20}$ −75 (c 0.2, CHCl$_3$); $^1$H NMR (600 MHz, CDCl$_3$) δ (ppm) 7.44-7.43 (m, 4H, 4×CH-Ar), 7.37-7.29 (m, 11H, 11×CH-Ar), 5.49 (2×s, 2H, H-7A, H-7C), 5.31 (s, 1H, H-1B*), 5.30 (d, J=2.7 Hz, 1H, H-2D), 5.28 (d, J=3.4 Hz, 1H, H-2B), 5.26 (s, 1H, H-1D*), 4.84 (d, J=10.9 Hz, 1H, CHH$_{Bn}$), 4.76 (d, J=10.9 Hz, 1H, CHH$_{Bn}$), 4.50-4.47 (m, 2H, H-1A, H-1C), 4.33 (td, J=10.2 Hz, J=4.9 Hz, 2H, H-6aA, H-6aC), 4.19-4.14 (m, 2H, H-5B, H-5D), 4.03 (t, J=3.5 Hz, 1H, H-3B), 3.95 (t, J=9.2 Hz, 1H, H-3A), 3.91-3.86 (m, 2H, H-1$_{linker}$, H-3C), 3.75 (t, J=10.2 Hz, 2H, H-6bA, H-6bC), 3.60-3.58 (m, 2H, H-2C, H-4D), 3.54-3.50 (m, 5H, H-3D, H-4A, H-4B, H4C, H-1b$_{linker}$), 3.46-3.42 (m, 3H, H-2A, H-5A, H-5C), 3.40 (s, 3H, CH$_{3Me}$), 2.85 (br s, 2H, H-5$_{linker}$), 2.11 (s, 3H, CH$_{3Ac}$), 2.05 (s, 3H, CH$_{3Ac}$), 1.75-1.67 (m, 2H, H-2$_{linker}$), 1.65-1.58 (m, 2H, H-4$_{linker}$), 1.41-1.38 (m, 2H, H-3$_{linker}$), 1.03 (d, J=6.5 Hz, 3H, H-6B*), 0.92 (d, J=6.4 Hz, 3H, H-6D*); $^{13}$C NMR (150 MHz, CDCl$_3$) δ (ppm) 169.8 (COOR$_{Ac}$), 168.9 (COOR$_{Ac}$), 138.2 (C-Ar), 137.2 (2C, 2×C-Ar), 129.6-126.2 (15C, 15×CH-Ar), 104.2 (C-1A*), 102.0, 101.8 (2C, C-7A, C-7C), 101.4 (C-1C*), 98.4, 98.2 (2C, C-1B, C-1D), 83.0 (C-2A), 79.2, 78.8 (2C, C-4A, C-4C), 76.4, 76.3 (C-3A, C-3C), 75.8 (C-2C), 74.9 (CH$_{2Bn}$), 74.3 (C-3D), 72.2 (C-3B), 70.0 (C-1$_{linker}$), 69.7-66.2 (10C, C-2B, C-2D, C-4B, C-4D, C-5A, C-5B, C-5C, C-5D, C-6A, C-6C), 56.4 (CH$_{3Me}$), 40.0 (C-5$_{linker}$), 29.2 (C-4$_{linker}$), 27.8 (C-2$_{linker}$), 23.2 (C-3$_{linker}$), 21.3 (CH$_{3Ac}$), 21.2 (CH$_{3Ac}$), 16.2, 16.0 (2C, C-6B, C-6D); HRMS (ESI-TOF) m/z [M+H]$^+$ calcd for C$_{55}$H$_{74}$NO$_{21}$ 1084.47478; found 1084.47259; m/z [M+Na]$^+$ calcd for C$_{55}$H$_{73}$NNaO$_{21}$ 1106.45673; found 1106.45461.

(5-Amino-1-pentyl) 2,4-di-O-acetyl-6-deoxy-3-O-methyl-α-L-talopyranosyl-(1→3)-β-D-glucopyranosyl-(1→3)-2-O-acetyl-6-deoxy-α-L-talopyranosyl-(1→3)-β-D-glucopyranoside hydrochloride (8)

Alcohol 40 (37 mg, 0.028 mmol, 1.0 equiv) was dissolved in DCE (0.3 mL) and MeOH (7.2 mL). The solution was degassed with Ar and Pd black (37 mg, 1 mg/mg of alcohol 40) and HCl (2.3 µL of a 12 N aq. solution, 0.028 mmol, 1.0 equiv) were successively added. The suspension was stirred under an atmosphere of H$_2$ at 40° C. for 16 h. The mixture was filtered over Celite to remove the catalyst and the cake was rinsed with MeOH. The solution was concentrated under reduced pressure. The residue was purified by LH-20 resin (MeOH) followed by reverse phase chromatography (100% H$_2$O to 1:1 H$_2$O/MeOH) to give tetrasaccharide 8 (15 mg, 60%) as a white amorphous solid: $R_f$ 0.3 (CHCl$_3$/MeOH/H$_2$O 10:10:3); $[\alpha]_D^{20}$ −34 (c 0.8, MeOH); $^1$H NMR (600 MHz, D$_2$O) δ (ppm) 5.37 (d, J=3.1 Hz, 1H, H-4D), 5.28 (s, 2H, H-1B*, H-2D), 5.22-5.21 (m, 2H, H-1D*, H-2B), 4.63 (d, J=8.0 Hz, 1H, H-1C*), 4.52 (q, J=6.4 Hz, 1H, H-5D), 4.45 (d, J=8.1 Hz, 1H, H-1A), 4.36 (q, J=6.6 Hz, 1H, H-5B), 4.24 (t, J=3.6 Hz, 1H, H-3B), 3.98 (t, J=3.4 Hz, 1H, H-3D), 3.96-3.90 (m, 3H, H-1a$_{linker}$, H-6aA*, H-4B), 3.85 (dd, J=12.3 Hz, J=2.0 Hz, 1H, H-6aC*), 3.75-3.66 (m, 3H, H-1b$_{linker}$, H-6bA, H-6bC), 3.63-3.57 (m, 2H, H-4A, H-4C), 3.52-3.43 (m, 5H, H-2C*, H-3A, H-3C, H-5A, H-5C), 3.40 (s, 3H, CH$_{3Me}$), 3.39-3.36 (m, 1H, H-2A*), 3.00 (t, J=7.2 Hz, 2H, H-5$_{linker}$), 2.21 (s, 3H, CH$_{3Ac}$), 2.17 (s, 3H, CH$_{3Ac}$), 2.16 (s, 3H, CH$_{3Ac}$), 1.71-1.64 (m, 4H, H-2$_{linker}$, H-4$_{linker}$), 1.48-1.43 (m, 2H, H-3$_{linker}$), 1.24 (d, J=6.6 Hz, 3H, H-6B), 1.14 (d, J=6.6 Hz, 3H, H-6D); $^{13}$C NMR (150 MHz, D$_2$O) δ (ppm) 174.4 (COOR$_{Ac}$), 174.1 (COOR$_{Ac}$), 173.7 (COOR$_{Ac}$), 102.6, 102.4 (2C, C-1A, C-1C), 99.4, 99.3 (2C, C-1B, C-1D), 82.8, 82.6 (2C, C-4A, C-4C), 76.5, 76.4 (2C, C-3A, C-3C), 74.2, 74.1 (2C, C-2A, C-2C), 73.9, 73.6 (2C, C-3B, C-3D), 70.8, 70.7 (2C, C-1$_{linker}$, C-2B), 70.1, 69.2, 68.8, 68.3, 68.1, 67.8 (6C, C-2D, C-4B, C-4D, C-5A, C-5B, C-5C), 66.3 (C-5D), 61.4, 61.1 (2C, C-6A, C-6C), 57.3 (CH$_{3Me}$), 40.0 (C-5$_{linker}$), 28.8 (C-4$_{linker}$), 27.1 (C-2$_{linker}$), 22.7 (C-3$_{linker}$), 21.3 (CH$_{3Ac}$), 21.1 (CH$_{3Ac}$), 21.0 (CH$_{3Ac}$), 16.0, 15.8 (2C, C-6B, C-6D); HRMS (ESI-TOF) m/z [M]$^+$ calcd for C$_{36}$H$_{62}$NO$_{22}$ 860.3758; found 860.37759.

(5-Amino-1-pentyl) 2-O-acetyl-6-deoxy-3-O-methyl-α-L-talopyranosyl-(1→3)-β-D-glucopyranosyl-(1→3)-2-O-acetyl-6-deoxy-α-L-talopyranosyl-(1→3)-δ-D-glucopyranoside hydrochloride (9)

Tetrasaccharide 43 (2 mg, 0.002 mmol, 1.0 equiv) was dissolved in DCE (0.02 mL) and MeOH (0.5 mL). The solution was degassed with Ar and Pd black (2 mg, 1 mg/mg of tetrasaccharide 43) and HCl (0.2 µL of a 12 N aq. solution, 0.002 mmol, 1.0 equiv) were successively added. The suspension was stirred under an atmosphere of $H_2$ at 40° C. for 16 h. The mixture was filtered over Celite to remove the catalyst and the cake was rinsed with MeOH. The solution was concentrated under reduced pressure. The residue was purified on reverse phase chromatography (100% $H_2O$ to 1:1 $H_2O$/MeOH) to give tetrasaccharide 9 (1.5 mg, 92%) as a white amorphous solid; $R_f$ 0.2 ($CHCl_3$/MeOH/$H_2O$ 10:10: 3); $[\alpha]_D^{20}$ −25 (c 0.2, MeOH); $^1H$ NMR (600 MHz, $D_2O$) δ (ppm) 5.25 (d, J=3.8 Hz, 1H, H-2D), 5.24 (s, 1H, H-1I31, 5.22-5.21 (m, 2H, H-1D*, H-2B), 4.63 (d, J=8.0 Hz, 1H, H-1C*), 4.45 (d, J=8.1 Hz, 1H, H-1A*), 4.38-4.33 (m, 2H, H-5B, H-5D), 4.24 (t, J=3.6 Hz, 1H, H-3B), 3.96-3.95 (m, 2H, H-4B, H-4D), 3.94-3.90 (m, 2H, H-1a$_{linker}$, H-6aA*), 3.85 (dd, J=12.3 Hz, J=2.0 Hz, 1H, H-6aC*), 3.79 (t, J=3.6 Hz, 1H, H-3D), 3.75-3.66 (m, 3H, H-1b$_{linker}$, H-6bA, H-6bC), 3.61-3.57 (m, 2H, H-4A, H-4C), 3.50-3.43 (m, 5H, H2C*, H-3A, H-3C, H-5A, H-5C), 3.41 (s, 3H, $CH_{3Me}$), 3.39-3.36 (m, 1H, H-2A*), 2.99 (t, J=7.2 Hz, 2H, H-5) 2.16 (s, 3H, $CH_{3Ac}$), 2.14 (s, 3H, $CH_{3Ac}$), 1.71-1.64 (m, 4H, H-2$_{linker}$, H-4$_{linker}$), 1.48-1.43 (m, 2H, H-3$_{linker}$), 1.24 (d, J=6.6 Hz, 6H, H-6B, H-6D); $^{13}C$ NMR (150 MHz, $D_2O$) δ (ppm) 174.1 (COOR$_{Ac}$), 173.9 (COOR$_{Ac}$), 102.6, 102.4 (2C, C-1A, C-1C), 99.4, 99.3 (2C, C-1B, C-1D), 82.8, 82.4 (2C, C-4A, C-4C), 76.5, 76.4 (2C, C-3A, C-3C), 74.3, 74.2 (2C, C-2A, C-2C), 74.1, 73.9 (2C, C-3B, C-3D), 70.8, 70.7 (2C, C-1$_{linker}$, C-2B), 69.2, 68.8, 68.6, 68.3, 68.2, 67.8, 67.7 (7C, C-2D, C-4B, C-4D, C-5A, C-5B, C-5C, C-5D), 61.4, 61.1 (2C, C-6A, C-6C), 56.2 ($CH_{3Me}$), 40.0 (C-5$_{linker}$), 28.8 (C-4$_{linker}$), 27.1 (C-2$_{linker}$), 22.7 (C-3$_{linker}$) 21.3 ($CH_{3Ac}$), 21.2 ($CH_{3Ac}$), 16.04, 15.99 (2C, C-6B, C-6D); HRMS (ESI-TOF) m/z $[M+H]^+$ calcd for $C_{34}H_{60}NO_{21}$ 818.36523; found 818.36495.

Antigenicity Evaluation of Synthetic Tetrasaccharides

Human serum ELISAs: Serum samples from culture-confirmed Thai melioidosis patients (n=42) were assayed for reactivity with Bp OPS and oligosaccharides 1-9 essentially as previously described (Suttisunhakul, V.; Wuthiekanun, V.; Brett, P. J.; Khusmith, S.; Day, N. P.; Burtnick, M. N.; Limmathurotsakul, D.; Chantratita, N. Development of a rapid enzyme-linked immunosorbent assays for detection of antibodies to *Burkholderia pseudomallei*. *J. Clin. Microbiol.* 2016, 54, 1259-1268). Briefly, maleic anhydride 96-well plates (Pierce) were coated overnight at 4° C. with oligosaccharides 1-9 (5 $\mu g \cdot mL^{-1}$) or purified Bp OPS (native LPS from *Burkholderia pseudomallei*) (10 $\mu g \cdot mL^{-1}$) solubilized in carbonate buffer (pH 9.6). The coated plates were blocked at room temperature for 30 min with StartingBlock T20 (TBS) Blocking Buffer (SB; Pierce) and then incubated for 1 h at 37° C. with serum samples at a fixed dilution of 1/2000 in Tris-buffered saline+0.05% Tween 20 (TBS-T)+10% SB. To enable the detection, the plates were incubated for 1 h at 37° C. with 1/2000dilution of goat anti-mouse IgG-horse radish peroxidase (HRP) conjugates (Southern Biotech). The plates were then developed with TMB substrate (KPL) and read at 620 nm. The data were plotted and analyzed using GraphPad Prism 5 (GraphPad Software Inc.).

The results depicted in FIG. 11 show that both tetrasaccharides 8 (MC82 in FIG. 11) and 9 (MC105 in FIG. 11) are able to detect antibodies present in serum samples from melioidosis patients. The ability of the tetrasaccharides to detect the antibodies was better than that of the di and tri-saccharides (Oligos 1-7), and at least equivalent (and possibly slightly better) than native LPS from *Burkholderia pseudomallei* (Bp OPS). Furthermore, tetrasaccharide 9, which mimics the LPS from *Burkholderia mallei*, was as effective as tetrasaccharide 8 (mimicking the LPS from *Burkholderia pseudomallei*) to detect antibodies present in serum samples from melioidosis patients (i.e. infected by *Burkholderia pseudomallei*). These results provide evidence that the tetrasaccharides exhibit cross-reactivity, and thus that either one of the tetrasaccharides could be used to induce the production of antibodies directed against both *Burkholderia pseudomallei* and *Burkholderia mallei*, and prevent melioidosis and glander.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

1 Danzig, R. & Berkowsky, P. B. Why should we be concerned about biological warfare? *J Amer Med Assoc* 278, 431-432 (1997).
2 Pearson, G. S. The threat of deliberate disease in the 21st century. *Biological Weapons Proliferation: Reasons for Concern, Courses of Action,* 31 (1998).
3 Dance, D. Melioidosis: the tip of the iceberg? *Clinical Microbiology Reviews* 4, 52-60 (1991).
4 Cheng, A. C. & Currie, B. J. Melioidosis: epidemiology, pathophysiology, and management. *Clinical microbiology reviews* 18, 383-416 (2005).
5 Program, F. S. A. 2017 Annual Report of the Federal Select Agent Program. (2017).
6 Keluangkhot, V., Pethsouvanh, R. & Strobel, M. Mélioïdose. *Médecine et maladies infectieuses* 35, 469-475 (2005).
7 Currie, B. J. in *Seminars in respiratory and critical care medicine.* 111-125 (Thieme Medical Publishers).
8 Khan, I. et al. Glanders in animals: a review on epidemiology, clinical presentation, diagnosis and countermeasures. *Transboundary and emerging diseases* 60, 204-221 (2013).
9 Diseases, U. A. M. R. I. o. I. *Medical management of biological casualties handbook.* (United States Army Medical Research Institute of Infectious Diseases, 1999).
10 Titball, R. W., Burtnick, M. N., Bancroft, G. J. & Brett, P. *Burkholderia pseudomallei* and *Burkholderia mallei* vaccines: Are we close to clinical trials? *Vaccine* 25, 5981-5989 (2017).
11 Cloutier, M., Muru, K., Ravicoularamin, G. & Gauthier, C. Polysaccharides from *Burkholderia* species as targets for vaccine development, immunomodulation and chemical synthesis. *Natural product reports* 35, 1251-1293 (2018).
12 Chantratita, N. et al. Survey of innate immune responses to *Burkholderia pseudomallei* in human blood identifies a central role for lipopolysaccharide. *PloS one* 8, e81617 (2013).
13 Bryan, L. E., Wong, S., Woods, D. E., Dance, D. A. & Chaowagul, W. Passive protection of diabetic rats with antisera specific for the polysaccharide portion of the lipopolysaccharide isolated from *Pseudomonas pseudomallei*. *Canadian Journal of Infectious Diseases and Medical Microbiology* 5, 170-178 (1994).

14 Ho, M. et al. Specificity and functional activity of anti-*Burkholderia pseudomallei* polysaccharide antibodies. *Infection and immunity* 65, 3648-3653 (1997).

15 Jones, S., Ellis, J., Russell, P., Griffin, K. & Oyston, P. Passive protection against *Burkholderia pseudomallei* infection in mice by monoclonal antibodies against capsular polysaccharide, lipopolysaccharide or proteins. *Journal of medical microbiology* 51, 1055-1062 (2002).

16 Trevino, S. R. et al. Monoclonal antibodies passively protect BALB/c mice against *Burkholderia mallei* aerosol challenge. *Infection and immunity* 74, 1958-1961 (2006).

17 Zhang, S. et al. In vitro and in vivo studies on monoclonal antibodies with prominent bactericidal activity against *Burkholderia pseudomallei* and *Burkholderia mallei*. *Clinical and Vaccine Immunology* (2011).

18 AuCoin, D. P. et al. Polysaccharide specific monoclonal antibodies provide passive protection against intranasal challenge with *Burkholderia pseudomallei*. *PLoS One* 7, e35386 (2012).

19 Nelson, M. et al. Evaluation of lipopolysaccharide and capsular polysaccharide as subunit vaccines against experimental melioidosis. *Journal of medical microbiology* 53, 1177-1182 (2004).

20 Scott, A. E. et al. Protection against experimental melioidosis following immunisation with a lipopolysaccharide-protein conjugate. *Journal of immunology research* 2014 (2014).

21 Knirel, Y. A. et al. Structure of the polysaccharide chains of *Pseudomonas pseudomallei* lipopolysaccharides. *Carbohydrate research* 233, 185-193 (1992).

22 Perry, M. B., MacLean, L. L., Schollaardt, T., Bryan, L. E. & Ho, M. Structural characterization of the lipopolysaccharide O antigens of *Burkholderia pseudomallei*. *Infect Immun* 63, 3348-3352 (1995).

23 Burtnick, M. N., Brett, P. J. & Woods, D. E. Molecular and physical characterization of *Burkholderia mallei* O antigens. *Journal of bacteriology* 184, 849-852 (2002).

24 Brett, P. J., Burtnick, M. N. & Woods, D. E. The wbiA locus is required for the 2-O-acetylation of lipopolysaccharides expressed by *Burkholderia pseudomallei* and *Burkholderia thailandensis*. *FEMS microbiology letters* 218, 323-328 (2003).

25 Heiss, C. et al. Revised structures for the predominant O-polysaccharides expressed by *Burkholderia pseudomallei* and *Burkholderia mallei*. *Carbohydrate research* 381, 6-11 (2013).

26 Heiss, C., Burtnick, M. N., Black, I., Azadi, P. & Brett, P. J. Detailed structural analysis of the O-polysaccharide expressed by *Burkholderia thailandensis* E264. *Carbohydrate research* 363, 23-28 (2012).

27 Tamigney Kenfack, M. et al. Deciphering minimal antigenic epitopes associated with *Burkholderia pseudomallei* and *Burkholderia mallei* lipopolysaccharide O-antigens. *Nature communications* 8, 115, doi:10.1038/s41467-017-00173-8 (2017).

28 Wada, T., Ohkubo, A., Mochizuki, A. & Sekine, M. 2-(Azidomethyl) benzoyl as a new protecting group in nucleosides. *Tetrahedron Letters* 42, 1069-1072 (2001).

29 Arasappan, A. & Fuchs, P. Regiospecific 4, 6-functionalization of pyranosides via dimethylboron bromide-mediated cleavage of phthalide orthoesters. *Journal of the American Chemical Society* 117, 177-183 (1995).

30 Love, K. R., Andrade, R. B. & Seeberger, P. H. Linear synthesis of a protected H-type II pentasaccharide using glycosyl phosphate building blocks. *The Journal of organic chemistry* 66, 8165-8176 (2001).

31 Gauthier, C. et al. Non-stoichiometric O-acetylation of Shigella flexneri 2a O-specific polysaccharide: synthesis and antigenicity. *Organic & biomolecular chemistry* 12, 4218-4232 (2014).

32 Lian, G., Zhang, X. & Yu, B. Thioglycosides in carbohydrate research. *Carbohydrate research* 403, 13-22 (2015).

33 Ellervik, U., Grundberg, H. & Magnusson, G. Synthesis of lactam and acetamido analogues of sialyl Lewis X tetrasaccharide and Lewis X trisaccharide. *The Journal of organic chemistry* 63, 9323-9338 (1998).

34 Wang, C. -C. et al. Regioselective one-pot protection of carbohydrates. *Nature* 446, 896 (2007).

35 Neises, B. & Steglich, W. Simple method for the esterification of carboxylic acids. *Angewandte Chemie International Edition in English* 17, 522-524 (1978).

36 Baudry, D., Ephritikhine, M. & Felkin, H. Isomerisation of allyl ethers catalysed by the cationic iridium complex [Ir (cyclo-octa-1, 5-diene)(PMePh 2) 2] PF 6. A highly stereoselective route to trans-propenyl ethers. *Journal of the Chemical Society, Chemical Communications,* 694-695 (1978).

37 Oltvoort, J., Van Boeckel, C., De Koning, J. & Van Boom, J. Use of the cationic iridium complex 1, 5-cyclooctadiene-bis [methyldiphenylphosphine]-iridium hexafluorophosphate in carbohydrate chemistry: Smooth isomerization of allyl ethers to 1-propenyl ethers. *Synthesis* 1981, 305-308 (1981).

38 Nashed, M. A. & Anderson, L. Iodine as a reagent for the ready hydrolysis of prop-1-enyl glycosides, or their conversion into oxazolines. *Journal of the Chemical Society, Chemical Communications,* 1274-1276 (1982).

39 Mukhopadhyay, B. & Field, R. A. Convergent synthesis of a trisaccharide as its 2-(trimethylsilyl) ethyl glycoside related to the flavonoid triglycoside from Gymnema sylvestre. *Carbohydrate research* 341, 1697-1701 (2006).

40 Cai, X. et al. Efficient synthesis of a 6-deoxytalose tetrasaccharide related to the antigenic O-polysaccharide produced by Aggregatibacter actinomycetemcomitans serotype c. *Carbohydrate research* 345, 1230-1234 (2010).

41 Frihed, T. G., Pedersen, C. M. & Bols, M. Synthesis of All Eight Stereoisomeric 6-Deoxy-L-hexopyranosyl DonorsTrends in Using Stereoselective Reductions or Mitsunobu Epimerizations. *European Journal of Organic Chemistry* 2014, 7924-7939 (2014).

42 Ohara, K. et al. Synthesis and Bioactivity of β-(1→4)-Linked Oligomannoses and Partially Acetylated Derivatives. *The Journal of organic chemistry* 78, 6390-6411 (2013).

43 Love, K. R. & Seeberger, P. H. Solution syntheses of protected type II Lewis blood group oligosaccharides: Study for automated synthesis. *The Journal of organic chemistry* 70, 3168-3177 (2005).

44 Tamigney Kenfack, M., Bleriot, Y. & Gauthier, C. Intramolecular Aglycon Delivery Enables the Synthesis of 6-Deoxy-β-D-manno-heptosides as Fragments of *Burkholderia pseudomallei* and *Burkholderia mallei* Capsular Polysaccharide. *The Journal of organic chemistry* 79, 4615-4634 (2014).

Suttisunhakul, V.; Wuthiekanun, V.; Brett, P. J.; Khusmith, S.; Day, N. P.; Burtnick, M. N.; Limmathurotsakul, D.; Chantratita, N. Development of a rapid enzyme-linked immunosorbent assays for detection of antibodies to *Burkholderia pseudomallei. J. Clin. Microbiol.* 2016, 54, 1259-1268.

The invention claimed is:

1. A conjugate with the formula:

[Chemical structure showing two disaccharide units with substituents R'O, OMe, OAc, OH, HO, and linker O—L—NH—molecule]

wherein:
- Ac represents an acetyl (CH$_3$—C(=O)—) group,
- Me represents a methyl group,
- R$^1$ represents —H or an acetyl group,
- R$^2$ represents —H or an acetyl group,
- L represents a C$_2$-C$_6$ alkylene group, or -L- together with the oxygen atom to which it is attached forms 1 to 3 polyethylene glycol repeat units and
- molecule is a vaccine carrier molecule.

2. The conjugate of claim 1, wherein R$^1$ represents —H.

3. The conjugate of claim 1, wherein R$^1$ represents an acetyl group.

4. The conjugate of claim 1, wherein R$^2$ represents —H.

5. The conjugate of claim 1, wherein -L-represents a C$_2$-C$_6$ alkylene group.

6. The conjugate of claim 1, wherein the vaccine carrier molecule is a protein carrier.

7. The conjugate of claim 1, wherein the vaccine carrier molecule is diphtheria toxoid (DT), a cross-reacting material (CRM) of diphtheria toxin, tetanus toxoid (TT), meningococcal outer membrane protein complex (OMPC), or *H. influenzae* protein D (HiD).

8. The conjugate of claim 7, wherein the vaccine carrier molecule is CRM$_{197}$.

9. A composition comprising the conjugate of claim 1 and a pharmaceutically acceptable excipient.

10. The composition of claim 9, wherein the pharmaceutically acceptable excipient comprises a vaccine adjuvant.

11. A method for inducing the production of anti-*Burkholderia* antibodies in a subject, the method comprising administering to the subject an effective amount of the conjugate of claim 1, wherein the *Burkholderia* is *Burkholderia pseudomallei* (Bp) or *Burkholderia mallei* (Bm).

12. The method of claim 11, wherein the *Burkholderia* is an infection by *Burkholderia pseudomallei* (Bp).

13. The method of claim 11, wherein the *Burkholderia* is an infection by *Burkholderia mallei* (Bm).

14. The method of claim 11, wherein the subject suffers from or is at risks of suffering from melioidosis or glanders.

15. The method of claim 14, wherein the subject suffers from or is at risks of suffering from melioidosis.

16. The method of claim 14, wherein the subject suffers from or is at risks of suffering from glanders.

* * * * *